United States Patent
Simons et al.

(10) Patent No.: US 9,475,880 B2
(45) Date of Patent: Oct. 25, 2016

(54) ANTI-CD134 (OX40) ANTIBODIES AND USES THEREOF

(75) Inventors: Petrus Johannes Simons, Hillegom (NL); Louis Boon, Badhoevedorp (NL)

(73) Assignees: Biocerox Products, B.V., Utrecht (NL); Janssen Pharmaceuticals, Inc., Titusville, NJ (US)

( * ) Notice: Subject to any disclaimer, the term of this patent is extended or adjusted under 35 U.S.C. 154(b) by 0 days.

(21) Appl. No.: 14/345,222

(22) PCT Filed: Sep. 13, 2012

(86) PCT No.: PCT/GB2012/052268
§ 371 (c)(1),
(2), (4) Date: Mar. 14, 2014

(87) PCT Pub. No.: WO2013/038191
PCT Pub. Date: Mar. 21, 2013

(65) Prior Publication Data
US 2015/0132288 A1 May 14, 2015

(30) Foreign Application Priority Data

Sep. 16, 2011 (GB) .................. 1116092.6

(51) Int. Cl.
C07K 16/28 (2006.01)
G01N 33/68 (2006.01)

(52) U.S. Cl.
CPC ....... C07K 16/2878 (2013.01); G01N 33/6854 (2013.01); C07K 2317/24 (2013.01); C07K 2317/34 (2013.01); C07K 2317/54 (2013.01); C07K 2317/55 (2013.01); C07K 2317/56 (2013.01); C07K 2317/565 (2013.01); C07K 2317/74 (2013.01); G01N 2333/705 (2013.01)

(58) Field of Classification Search
CPC ................... C07K 16/2878; C07K 2317/565; C07K 2317/24; C07K 2317/56
USPC ..................... 424/139.1; 530/387.3
See application file for complete search history.

(56) References Cited

U.S. PATENT DOCUMENTS

| | | | |
|---|---|---|---|
| 4,946,778 | A | 8/1990 | Ladner et al. |
| 5,225,539 | A | 7/1993 | Winter |
| 5,463,564 | A | 10/1995 | Agrafiotis et al. |
| 5,534,254 | A | 7/1996 | Huston et al. |
| 5,565,332 | A | 10/1996 | Hoogenboom et al. |
| 5,723,322 | A | 3/1998 | Guettler et al. |
| 5,901,069 | A | 5/1999 | Agrafiotis et al. |
| 5,932,448 | A | 8/1999 | Tso et al. |
| 6,291,158 | B1 | 9/2001 | Winter et al. |
| 6,582,915 | B1 | 6/2003 | Griffiths et al. |
| 6,593,081 | B1 | 7/2003 | Griffiths et al. |
| 6,737,056 | B1 | 5/2004 | Presta |
| 6,765,087 | B1 | 7/2004 | Casterman et al. |
| 6,818,749 | B1 | 11/2004 | Kashmiri et al. |
| 6,833,441 | B2 | 12/2004 | Wang et al. |
| 6,838,254 | B1 | 1/2005 | Hamers et al. |
| 7,550,140 | B2 | 6/2009 | Bakker et al. |
| 7,695,936 | B2 | 4/2010 | Carter et al. |
| 7,709,226 | B2 | 5/2010 | Foote |
| 2001/0044522 | A1 | 11/2001 | Godfrey et al. |
| 2002/0004041 | A1 | 1/2002 | Albert et al. |
| 2006/0153808 | A1 | 7/2006 | Cristofanilli et al. |
| 2007/0117809 | A1 | 5/2007 | Fridman |
| 2007/0287170 | A1 | 12/2007 | Davis et al. |
| 2009/0118127 | A1 | 5/2009 | Raghunathan |
| 2009/0214560 | A1 | 8/2009 | Min et al. |
| 2010/0015133 | A1 | 1/2010 | Igawa et al. |
| 2010/0261620 | A1 | 10/2010 | Almagro et al. |
| 2010/0286374 | A1 | 11/2010 | Kannan et al. |
| 2011/0028688 | A1 | 2/2011 | Hymowitz et al. |
| 2011/0104053 | A1 | 5/2011 | Rodriguez et al. |
| 2011/0123532 | A1 | 5/2011 | Gurney et al. |
| 2011/0123552 | A1 | 5/2011 | Bakker et al. |
| 2012/0149876 | A1 | 6/2012 | Von Kreudenstein et al. |
| 2014/0377284 | A1* | 12/2014 | Simons et al. ............ 424/174.1 |
| 2015/0132288 | A1 | 5/2015 | Simons et al. |

FOREIGN PATENT DOCUMENTS

| | | |
|---|---|---|
| JP | 2009-518005 | 5/2009 |
| WO | WO9007861 A1 | 7/1990 |
| WO | WO9201047 A1 | 1/1992 |
| WO | WO9222653 A1 | 12/1992 |
| WO | WO9942585 A1 | 8/1999 |
| WO | WO03002609 A2 | 1/2003 |
| WO | WO03040170 A2 | 5/2003 |

(Continued)

OTHER PUBLICATIONS

Rudikoff et al (Proc Natl Acad Sci USA 1982 vol. 79 p. 1979).*
MacCallum et al. (J. Mol. Biol. (1996) 262:732-745).*
De Pascalis et al. The Journal of Immunology (2002) 169, 3076-3084.*
Casset et al. ((2003) BBRC 307, 198-205).*
Vajdos et al. ((2002) J. Mol. Biol. 320, 415-428).*
Holm et al ((2007) Mol. Immunol. 44: 1075-1084).*
Chen et al. J. Mol. Bio. (1999) 293, 865-881.*
Wu et al. (J. Mol. Biol. (1999) 294, 151-162).*
Brummell et al. (Biochemistry 32:1180-1187 (1993)).*
Kobayashi et al. (Protein Engineering 12:879-844 (1999)).*
Burks et al. (PNAS 94:412-417 (1997)).*
Jang et al. (Molec. Immunol. 35:1207-1217 (1998)).*
Brorson et al. (J. Immunol. 163:6694-6701 (1999)).*
Coleman (Research in Immunol. 145:33-36 (1994)).*

(Continued)

*Primary Examiner* — Lynn Bristol
(74) *Attorney, Agent, or Firm* — Baker & Hostetler LLP

(57) ABSTRACT

The invention provides antibodies that specifically bind to human CD134. Invention anti-human CD134 antibodies specifically bind to the extracellular domain of human CD134, including non-OX40 ligand (OX40L) binding domains on human CD134, which is expressed on e.g. activated human conventional effector CD4 and/or CD8 T lymphocytes (Teffs) and on activated human suppressive regulatory CD4 T lymphocytes (Tregs). Invention anti-human CD134 antibodies are useful (e.g. to empower Teffs anti-cancer effector function and/or to inhibit Tregs suppressive function) for cancer treatment.

14 Claims, 30 Drawing Sheets

(56) References Cited

FOREIGN PATENT DOCUMENTS

| WO | WO2004003019 A2 | 1/2004 |
| --- | --- | --- |
| WO | WO 2004/003019 * | 6/2004 |
| WO | WO2004111233 A1 | 12/2004 |
| WO | WO 2006/050172 A2 | 5/2006 |
| WO | WO2006079372 A1 | 8/2006 |
| WO | WO2006088639 A1 | 8/2006 |
| WO | WO2006129163 A1 | 12/2006 |
| WO | WO 2007-062245 | 5/2007 |
| WO | WO2007059782 A1 | 5/2007 |
| WO | WO2007062235 A2 | 5/2007 |
| WO | WO 2008-106116 | 9/2008 |
| WO | WO2008119353 A1 | 10/2008 |
| WO | WO 2008/133851 A1 | 11/2008 |
| WO | WO 2009/079335 A1 | 6/2009 |
| WO | WO2009085462 A1 | 7/2009 |
| WO | WO2009134776 A2 | 11/2009 |
| WO | WO2010019702 A2 | 2/2010 |
| WO | WO 2010-096418 | 8/2010 |
| WO | WO2011066501 A1 | 6/2011 |
| WO | WO2011131746 A2 | 10/2011 |
| WO | WO2011143545 A1 | 11/2011 |
| WO | WO 2012-027328 | 3/2012 |
| WO | WO 2013-008171 | 1/2013 |
| WO | WO 2013-068563 | 5/2013 |

OTHER PUBLICATIONS

Ward et al. (Nature 341:544-546 (1989)).*
Smith-Gill et al. (J. Immunol. 139:4135-4144 (1987)).*
Kumar et al. (J. Biol. Chem. 275:35129-35136 (2000)).*
Song et al. (Biochem Biophys Res Comm 268:390-394 (2000)).*
International Search Report for PCT/GB2012/052268, mailed Apr. 31, 2013, 6 pages.
Santa Cruz Biotechnology, Inc., "anti-OX40-receptor antibody (H-10)", Jan. 2001, retrieved from the Internet: http://datasheets.scbt.com/sc-376014.pdf, retrieved on Dec. 5, 2012.
Santa Cruz Biotechnology, Inc., "anti-OX40-receptor antibody (H-133)", Jan. 2011, retrieved from the Internet: http://datasheets.scbt.com/sc-11403.pdf, retrieved on Dec. 5, 2012.
"Harbour Antibodies", www.harbourantibodies.com, accessed May 29, 2015, 1 page.
"Science to Medicine", www.regeneron.com, accessed May 29, 2015, 2 pages.
Ablexis, "Developing a Next Generation Platform for Antibody Drug Discovery", www.ablexis.com, accessed May 29, 2015, 1 page.
Ai-Shamkhani, et al., "OX40 is Differentially Expressed on Activated Rat and Mouse T Cells and is the Sole Receptor for the OX40 Ligand", Eur J Chem., vol. 26, Aug. 1996, 1695-1699.
Angel, et al., "A Single Amino Acid Substitution Abolishes the Heterogeneity of Chimeric Mouse/Human (igG4) Antibody", Mol. Immunol., 1993, vol. 30(1), 105-108.
Attucci et al., "EPI-Hne4, A Proteolysis-Resistant Inhibitor of Human Neutrophil Elastase and Potential Anti-Inflammatory Drug for Treating Cystic Fibrosis", J. Pharmacal. Exp. Ther., vol. 318, Aug. 2006, 803-80.
Bianchi et al. "High Level Expression and Rational Mutagenesis of a Designed Protein, The Minibody. From an Insoluble to a Soluble Molecule", J. Mal. Biol., vol. 236(2), Feb. 18, 1994, 649-59.
Binz et al., "High-Affinity Binders Selected from Designed Ankyrin Repeat Protein Libraries", Nat. Biotechnol., vol. 22, Apr. 18, 2004, 575-582.
Bird et al., "Single-Chain Antigen-Binding Proteins", Science, Oct. 1988, vol. 242(4877), 423-426.
Bodmer et al., "The Molecualr Architecture of the TNF Superfamily", Trends Biochem Sci., Jan. 2002, vol. 27(1), 19-26.
Borghouts et al., "Peptide Aptamers: Recent Developments for Cancer Therapy", Expert Opin. Biol. Ther., Jun. 2005, vol. 5(6), 783-797.

Chothia et al. Conformations of immunoglobulin hypervariable regions, Nature, 1989, 342(6252), 877-83.
Compaan et al., "The Crystal Structure of the Costimulatory OX 40-OX40L Complex", Structure, Aug. 2006, vol. 14 (8), 1321-1330.
Dall' Acqua et al, "Properties of Human IgGls Engineered for Enhanced Binding to the Neonatal Fc Receptor (FcRn)", J. Biol. Chem., May 4, 2006, vol. 281(235), 14-24.
Doppalapudi, et al., "Chemically Programmed Antibodies: Endothelin Receptor Targeting Cov X-Bodies", Jan. 15, 2007, Bioorg. Med. Chem. Lett., vol. 17(2), 501-6.
Evans, et al. "Rapid Expression of an Anti-Human C5 Chimeric Fab Utilizing a Vector that Replicates in COS and 293 Cells", J. Immunot Meth, Jul. 1995, 184(1), 123-138.
Gao et al. "Molecular Cloning of a Proteolytic Antibody Light Chain", J. Biol. Chem. Dec. 23, 1994, vol. 269(51), 32389-93.
Gasset et al., "A peptide mimetic of an anti-CD4 monoclonal antibody by rational design", BBRC, 2003, 307, 98-105.
Gri et al. "Cd4+CD25+Regulatory T Cells Suppress Mast Cell Degranulation and Allergic Responses Through OX40-OX4OL Interaction", Immunity, Nov. 14, 2008, vol. 29(5), 771-81.
Heap et al., "Analysis of a 17-Amino Acid Residue, Virus-Neutralizing Microantibody", J. Gen. Viral., Jun. 2005, vol. 36(Pt 6), 1791-1800.
Hey et al., "Articivial, Non-Antibody Binding Proteins for Pharmaceutical and Industrial Application", Trend. Biotechnol., Oct. 2005, vol. 23(10), 514-522.
Hirschhorn-Cymerman, et al., "OX40 Engagement and Chemotherapy Combination Provides Potent Antitumore Immunity with Concomitant Regulatory T Cells Apoptosis", J. Exp. Med, May 4, 2009, vol. 206(5), 1103-1116.
Holliger, et al., "Diabodies: Small Bivalent and Bispecific Antibody Fragments", Jul. 15, 1993, vol. 90(14), Proc. Natl. Acad. Sci. USA, 6444-6448.
Huston et al., "Protein Engeneering of Antibody Binding Sites: Recovery of Specific Activity in an Anti-Digoxin Single-Chain Fv Analogue Produced in *Escherichia Coli*", Aug. 1988, Proc. Natl. Acad. Sci. USA 85(16), 5879-5883.
Imura, et al., "The Human OX40/gp34 System Directly Mediates Adhesion of Activated T Cells to Vascular Endothelial ells", J. Exp. Med., May 1, 1996, vol. 183(5), 2185-95.
Kashiwakura, et al., T Cell Proliferation by Direct Cross-Talk Between OX40 Ligand on Human Mast Cells and OX40 on Human T Cells: Comparison of Gene Expression Profiles Between Human Tonsillar and Lung-Cultures Mast Cells, J. Immunol., Oct. 1, 2004, vol. 173, 5247-5257.
Kim, et al., "CD4(+)CD3(-) Accessory Cells Costimulate Primed CD4 T Cells Through OX40 and CD30 at Sites Where T Cells Collaborate with B Cells", May 18, 2003, vol. 18(5), 643- 54.
Kipriyanov, et al."Single-Chaim Antibody Streptavidin Fusions: Tetrameric Bifunctional scFv- Complexes with Biotin Binding Acivity and Enhanced Affinity and Antigen", Hum Antibodies Hybridomas, 1995, vol. 6(3), 93-101.
Klein, et al, "Epitope Interactions of Monoclonal Antibodies Targeting CD20 and Their Relationship to Functional roperties", MAbs, Jan. 1, 2013 vol. 5(1), 22-33.
Kohler, et al., "Continuous Cultures of Fused Cells Secreting Antibody of Predefined Specificity", Nature, Aug. 7, 1975, vol. 256(5517),495-497.
Koide et al., "Monobodies: Antibody Mimics Based on the Scaffold of the Fibronectin Type III Domain", Meth. Mal. Biol., 2007, 352, 95-109.
Krause et al., Grafting of Thrombopoietin-Mimetic Peptides into Cystine Knot Miniproteins Yields High-Affinity Thrombopoietin Antagonists and Agonists, FEBS J, Jan. 2007, vol. 274(1), 86-95.
KyMab, "Advanced Therapeutic Antibody Discovery & Development", Vv'WW.kymab.com, May 29, 2015, 3 pages.
Ladner et al., "Antibodies Cut Down to Size", Nature Biotechnology, Aug. 2007, 25(8), 875-7.
Latza et al., "The Humans OX40 Homolog: cDNA Structure, Expression and Chromosomal Assignment of the ACT35 Antigen", Eur. J. Immunol. Mar. 1994; 24(3), 677-683.

(56) References Cited

OTHER PUBLICATIONS

Laune, et al., "Systematic Exploration of the Antigen Binding Activity of Synthetic Peptides Isolated from the Variable Regions of Immunoglobulins", J. Biol. Chem., 1997, 272(49), 30937-44.
Linton, et al., "Costimulation Via OX40L Expressed by B Cells is Sufficient to Determine the Extent of Primary CD4 Cell Expansion and Th2 Cytokine Secretion in Vivi", J. Exp. Med., 875-883.
Maclennan, et al., "Structure-Function Relationships in the Ca(2+)-Binding and Translocation Domain of Serca1: Physiological Correlates in Brody Disease", Act Physiol. Scand. Suppl., Aug. 1998, vol. 643, 55-67.
Mayes et al., "Synthetic Strategies for the Generation of Molecularly Imprinted Organic Polymers", Adv. Drug Deily. Rev., 2005, vol. 57(17), 42-78.
Monnet, et al., "Synthetic Peptides Derived from the Variable Regions of an Anti-CD4 and Inhibit HIV-1 Promoter Activation in Virus Infected Cells", J. Biol. Chem., 1999, 274, 3789-96.
Morris, et al., "Development and Characterization of Recombinant Human Fe: OX40L Fusion Protein Linked Via A boiled-Coil Trimerization Domain", Mal. Immunol., May 2007, 44(12), 3112-3121.
Nakae, et al., "Mast Cells Enhance T Cell Activation: Importance of Mast Cell Costimulatory Molecules and Secreted TNF", J. Immunol., 2006, vol. 176, 2238-2248.
Nicaise, et al., "Affinity Transfer by CDR Grafting om A Nonimmunoglobulin Scaffold", Protein Science, Jul. 2004, vol. 13(7), 1882-91.
Nygren, et al., "Alternative Binding Proteins: Affibody Binding Proteins Developed from a Small Three-Helix Bundle Scaffold", Jun. 2008, FEBS J, vol. 275(11), 2668-2676.
Open Monoclonal Technology, "Naturally Optimized Human Antibodies", www.omtinc.net, accessed May 29, 2015, 2 pages.
Osborn et al., "From Rodent Reagents to Human Therapeutics Using Antibody Guided Selection", Methods, May 2005, vol. 36(1), 61-68.
Padlan, "A Possible Procedure For Reducing The Immunogenicity of Antibody Variable Domains While Preserving Their Ligand-Binding Properties", Mal. Immunol., 1991, vol. 28(415), 489-499.
Pandiyan, et al., "CD4+CD25+Foxp3+Regulatory T Cells Induce Cytokine Deprivation-Mediated Apoptosis of Effector CD4+T Cells", Nat. Immunol., Dec. 2007, 8(12), 1353-62.
De Pascalis et al., "Grafting of "Abbreviated" Complementary-Determining Regions Containing Specificity-Determining Residues Essential for Ligand Contact to Engineer a Less Immunogenic Humanized Monoclonal Antibody", The Journal of Immunology, 2002, 69, 3076-3084.
Pessi, et al., "A Designed Metal-Binding Protein with a Novel Fold", Nature, Mar. 25, 1993, vol. 362(6418), 367-9.
Piconese, et al., "Mast Cells Couteract Regulatory T-Cell Suppression Through Interleukin-6 and OX40/0X40L Axis Toward Th17-Cell Differentiation", Blood, Sep. 24, 2009, vol. 114(13), 2639-48.
Piconese, et al., "OX40 Triggering Blocks Suppression by Regulatory T Cells and Facilitates Tumor Rejection", J. Exp. Med., Apr. 14, 2008, vol. 205(4), 825-839.
Poljak, et al., "Production and Structure of Diabodies", Structure, 1994, vol. 2, 1121-1123.
Qiu, et al., "Small Antibody Mimetics Comprising Two Complementarity-Determining Regions and a Framework Region for Tumor Targeting", Nature Biotechnology, Aug. 5, 2007, vol. 25(8), 921-9.
Quezda, et al., "Shifting the Equilibrium in Cancer Immunoediting: From Tumor Tolerance to Eradication", Immunol. Rev., 2011, vol. 241, 104-118.
Quiocho, "Protein Engineering. Making of the Minibody", Nature, Mar. 25, 1993, vol. 362(6418), 293-4.
Ramstad, et al., "Immunohistochemical Analysis of Primary Breast Tumors and Tumor- Draining Lymph Nodes by Means of the T-Cell Costimulatory Molecule OX-40", Am. J. Surg., May 2000, 179(5), 400-406.

Root-Bemstein, et al., "Small Molecule Complementarity As A Source of Novel Pharmaceutical Agents and combination Therapies", Cur. Pharm. Des., 2008, vol. 14, 55-62.
Sasaki, et al., "Structure-Mutation Analysis of the ATPase Site of Dictyostelium Discoideum Myosin II", Jan. 20, 1998. Adv. Biopsy's., vol. 35,1-24.
Scheffold, et al., "Competition for Cytokines: T reg Cells Take All", Nat Immunol, 2007, vol. 8, 1285-1287.
Schlehuber et al., "Lipocalins in Drug Discovery: From Natural Ligans-Binding Protiens to Anticalins", Drug Discovery Today, 2005, vol. 10(1), 23-33.
Shi, et al, "De Novo Selection of High-Affinity Antibodies from Synthetic Fab Libraties Displayed on Phage as Pix Fusion Proteins", Mar. 26, 2010, J. Mal. Biol., vol. 397(2), 385- 96.
Silverman, et al., "Multivalent Avimer Proteins Evolved by Exon Shuffling of a Family of Human Receptor Domains". Nat. Biotechnol., Nov. 20, 2005, 23, 1556-1561.
Skerra, et al., "Alternative Non-Antibody Scaffolds for Molecular Recognition", Aug. 18, 2007, Curr. Opin. Biotech., vol. 18(4), 295-304.
Soroosh, et al., "OX40-0X40 Ligand Interaction Through T Cell- T Cell Contact Contributes to CD4 T Cell Longevity", J. Immunol., May 15, 2006, vol. 176(10), 5975-87.
Sugamura, et al., "A Therapeutic targeting of the effector T-cell co-stimulatory molecule OX40", Nature Rev. Imm., 2004, vol. 4, 420-431.
Swiss-Prot, "Tumor Necrosis Factor Receptor Supeifamily Member 4, www.uniprot.org/uniproU P43489", accessed Jun. 4, 2015, 9 pages.
Taylor, et al., "Identification of a Soluble OX40 Isoform: Development of a Specific and Quantitative Immunoassay", J. mmunol. Methods, Sep. 1, 2001, vol. 255, 67-72.
Thogersen et al., "A Tetranectin-Based Platform for Protein Engineering", Innovations Pharmac. Technol, 2006, 27-30.
Trianni, "New Tedhnologies to Generate an Advanced Human Monoclonal Antibody Resource", httrrt/www.trianni.com. accessed May 29, 2015, 1 pg.
Vaughan, et al., "Of Minibody, Camel and Bacteriophage", Combinatorial Chemistry & High Throughput Screening, Aug. 2001, vol. 4(5), 417-430.
Vercoulen, et al., "Human Regulatory T Cell Suppressive Function Is Independent of Apoptosis Induction in Activated Effector T Cells", Plos One, Sep. 25, 2009, 4(9) e7183.
Vetto, et al., "Presence of the T-Cell Activation Marker OX-40 on Tumor Infiltrating Lymphocytes and Draining Lymph Node Cells From Patients with Melanoma and Head and Neck Cancers", Am J Surg., Sep. 1997, vol. 174(3), 258-265.
Weinberg, et al., "Anti-OX40 (CD123) Administration to Nonhuman Primates: Immunostimulatory Effects and Toxicokinetic Study", J. Immunother, 2006, 29(6), 575-585.
Worn et al., "Stability Engineering of Antibody Single-Chain Fv Fragments", J. Mal. Biol., Feb. 2, 2001, vol. 305(5), 989-1010.
Xie et al., "Costimulatory molecule OX40/OX40L expression in ductal carcinoma in situ and invasive ductal carcinoma of breast: An Innunohistochemistry-based pilot study", 2010, Pathology-Research and Practice. vol. 206. 735-739
Xu et al., "Diversity in the CDR3 Region of VH Is Sufficient for Most Antibody Specificities", Immunity, 2000, 13, 37-45.
Bashyam, H. And Sedwick, C., "How Alum Works", The Journal of Experimental Medicine, Mar. 24, 2008, 205(4), 742-743.
Dubrot et al, "Delivery Of Immunostimulatory Monoclonal Antibodies by Encapsulated Hybridoma Cells", Cancer Immunology Immunotherapy, Nov. 1, 2010, 59,1621-1631, (Abstract, 1 page).
Gray et al, "Therapeutic Potential Of Immunostimulatory Monoclonal Antibodies", Clinical Science, Jul. 2006, 111, 93-106.
Peggs et al, "Cancer Immunotherapy: Co-Stimulatory Agonists And Co-Inhibitory Antagonists", Clinical & Experimental Immunology, Jul. 2009, 157(1), 9-19.
Singapore Application No. 112014007065: Search Report dated May 23, 2016, 21 pages.

(56) References Cited

OTHER PUBLICATIONS

Ruby, C.E. And Weinberg, A.D., "The Effect of Aging on OX40 Agonist-Mediated Cancer Immunotherapy", Cancer Immunology Immunotherapy, Dec. 2009, 58(12), 1941-1947.

Anti-Mouse CD134 (OX40) PE, Clone: OX-86, e-Biosciences, 2 pages http://www.ebioscience.com/mousecd134 antibody pe ox 66 hlm.

Chile Application No. 631-2014: Office Action dated May 9, 2016, 1 page.

\* cited by examiner

Resting CD4 T cells

PHA-stimulated/activated CD4 T cells

ANTI-CD134 (OX40) ANTIBODIES AND USES THEREOF

CROSS-REFERENCE TO RELATED APPLICATIONS

This application is the national phase of PCT application PCT/GB2012/052268 having an international filing date of 13 Sep. 2012, which claims benefit of United Kingdom patent application No. 1116092.6 filed 16 Sep. 2011. The contents of the above patent applications are incorporated by reference herein in their entirety.

SEQUENCE LISTING

The instant application contains a Sequence Listing which has been submitted electronically in ASCII format and is hereby incorporated by reference in its entirety. Said ASCII copy, created on Dec. 4, 2014, is named 103270.000006-P100138US00_SL.txt and is 54,903 bytes in size.

FIELD OF THE INVENTION

The invention relates to antibodies, the use of such antibodies, and particularly to antibodies that bind to CD134, for the treatment of cancer.

BACKGROUND OF THE INVENTION

Enhancing anti-tumour T-cell function represents a unique approach for treating cancer. There is considerable evidence that tumour cells 'escape' the immune system by induction of an active immune tolerance largely mediated by regulatory T lymphocytes (Tregs; Quezda et al. Immunol Rev 2011; 241:104-118). Therefore, the balance between effector (i.e., direct or indirect eradication of tumour cells) T lymphocytes (Teffs) and tolerogenic (i.e., suppression of Teffs effector function and survival) Tregs appears to be crucial for effective anti-tumour immunotherapy. In other words, an effective anti-tumour immune response can be obtained by enhancing effector function of tumour-specific Teffs and/or by attenuating suppressive function of tumour-specific Tregs. A key receptor that has been shown to mediate these responses is the CD134 (OX40) receptor. (Sugamura, K, Ishii, N, Weinberg, A. Therapeutic targeting of the effector T-cell co-stimulatory molecule OX40. Nature Rev Imm 2004; 4: 420-431).

CD134 (also known as OX40, TNFRSF4, and ACT35) is a member of the tumour necrosis factor receptor superfamily. This CD134 surface co-stimulatory receptor is expressed on activated T lymphocytes, and plays an important role in their survival and function. The presence of CD134 expressing T lymphocytes has been demonstrated in various human malignant tumours and in the draining lymph nodes of cancer patients (Ramstad et al. Am J Surg 2000; 179: 400-406; Vetto et al. Am J Surg 1997; 174: 258-265).

In vivo ligation of the mouse CD134 receptor (by either soluble mouse OX40 ligand (OX40L)-immunoglobulin fusion proteins or mouse OX40L mimetics, such as anti-mouse CD134-specific antibodies) in tumour-bearing mice enhances anti-tumour immunity, leads to tumour-free survival in mouse models of various murine malignant tumour cell lines, e.g., lymphoma, melanoma, sarcoma, colon cancer, breast cancer, and glioma (Sugamura et al. Nature Rev Imm 2004; 4: 420-431).

It has been proposed to enhance the immune response of a mammal to an antigen by engaging the OX40R through the use of an OX40R binding agent (WO 99/42585; Weinberg, 2000). Although the document refers generally to OX40-binding agents, the emphasis is on the use of OX40L or parts thereof; the disclosure of anti-OX40 antibodies is in the context of their being equivalent to OX40L. Indeed, when the Weinberg team translated the research to a study with non-human primates, they again deliberately chose an antibody that binds to the OX40L-binding site and generally mimics OX40L.

Al-Shamkhani et al. (Eur J Chem 1996; 26: 1695-1699) used an anti-OX40 antibody called OX86, which did not block OX40L-binding, in order to explore differential expression of OX40 on activated mouse T-cells; and Hirschhorn-Cymerman et al. (J Exp Med 2009; 206: 1103-1116) used OX86 together with cyclophosphamide in a mouse model as a potential chemoimmunotherapy. However, OX86 would not be expected to bind human OX40 and, when choosing an antibody that would be effective in humans, one would, in the light of the Weinberg work, choose an antibody that did bind at the OX40L-binding site.

In vivo ligation of the human CD134 receptor (by anti-human CD134-specific antibodies which interact with the OX40L binding domain on human CD134; US 2009/0214560 A1) in severe combined immunodeficient (SCID) mice enhances anti-tumour immunity, which leads to tumour growth inhibition of various human malignant tumour cell lines, e.g. lymphoma, prostate cancer, colon cancer, and breast cancer.

The exact mechanism of human CD134 ligation-mediated anti-tumour immune responses in humans is not yet elucidated, but is thought to be mediated via the CD134 transmembrane signalling pathway that is stimulated by the interaction with OX40L. This interaction is mediated by the binding of trimeric OX40L to CD134. In current anti-cancer therapies, the use of trimerized OX40 ligand is proposed as a more effective agent than anti-OX40 antibodies (Morris et al. Mol Immunol 2007; 44: 3112-3121).

SUMMARY OF THE INVENTION

It has now been surprisingly found by the applicants that, in order to induce T-cell mediated anti-tumour activity, the use of isolated binding molecules that bind to human CD134, wherein the binding molecule does not prevent human CD134 (CD134) receptor binding to OX40 ligand (OX40L), results in an enhanced immune response, characterised by enhancing the immunostimulator/effector function of T-effector cells and/or proliferating those cells and/or down-regulation of the immunosuppressor function of T-regulatory cells.

The present invention therefore provides isolated binding molecules that bind to human CD134, wherein the binding molecule does not prevent human CD134 (OX40) receptor binding to OX40 ligand (OX40L).

Such binding molecules include suitable anti-CD134 antibodies, antigen-binding fragments of the anti-CD134 antibodies, and derivatives of the anti-CD134 antibodies. In some embodiments the binding molecule binds to human CD134 with a $K_d$ of $1\times10^{-7}$ M or less. The binding molecule has agonist activity on human CD134 on T-effector cells and/or antagonistic activity on human CD134 on T-regulator cells. In some further embodiments, the binding molecule is a human monoclonal antibody that specifically binds human CD134 with a $K_d$ of 100 nM or less, preferably less than 50 nM, more preferably less than 20 nM.

The present invention also provides a composition that comprises one or more of the binding molecules and a pharmaceutically acceptable carrier. In some embodiments, the binding molecule is a human monoclonal anti-CD134 antibody or an antigen-binding fragment thereof. The composition may further comprise additional pharmaceutical agents, such as immunotherapeutic agents, chemotherapeutic agents, and hormonal therapeutic agents.

The present invention further provides diagnostic and therapeutic methods of using the binding molecules. In some embodiments is provided a method of treating or preventing cancer in a mammal, comprising administering to the mammal a therapeutically effective amount of a binding molecule or a composition comprising a binding molecule as disclosed herein. In some other embodiments, the disclosure provides a method of enhancing an immune response in a mammal, comprising administering to the mammal a therapeutically effective amount of a binding molecule or a composition comprising a binding molecule. In particular embodiments, the binding molecule used in the methods is a human monoclonal anti-CD134 antibody or an antigen-binding fragment thereof, which binds to human CD134, wherein the antibody does not prevent human CD134 (OX40) receptor binding to OX40 ligand (OX40L).

The present invention further provides nucleic acid molecules that encode an amino acid sequence of a binding molecule, vectors comprising such nucleic acids, host cells comprising the vectors, and methods of preparing the binding molecules.

The disclosure also provides other aspects, which will be apparent from the entire disclosure, including the claims.

DESCRIPTION OF THE FIGURES

The invention is described with reference to the accompanying drawings.

DESCRIPTION OF THE INVENTION

Figure 1:
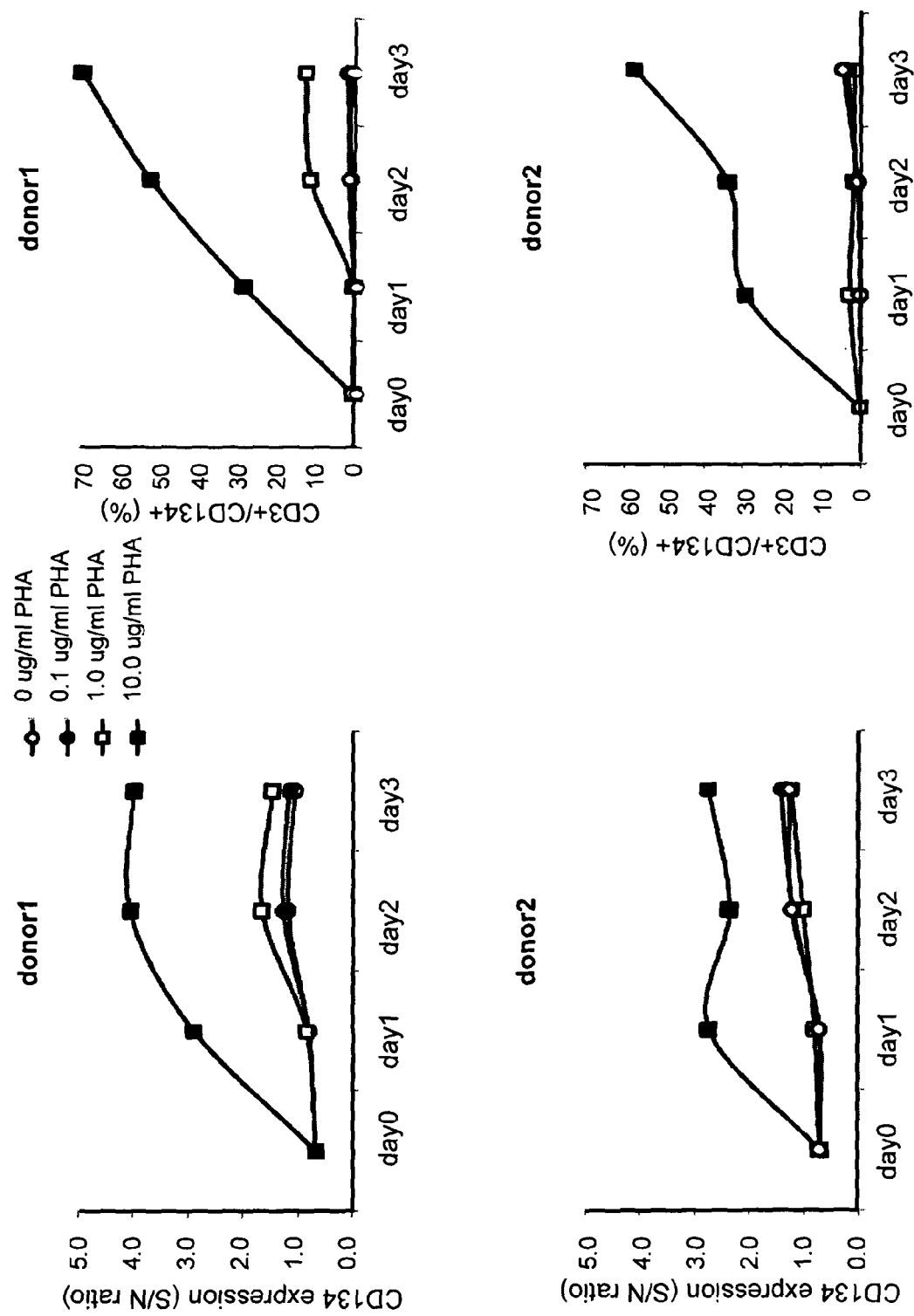
FIG. 1. Time course and dose effect of exposure to PHA-M on surface human CD134 expression of human T lymphocytes.

T-cell activation is mediated not only by antigen stimulation through T-cell receptors but also by co-stimulatory signals via co-stimulatory molecules. Among several co-stimulatory molecules, the tumour necrosis factor (TNF) receptor family member, OX40 (CD134) plays a key role in the survival and homeostasis of effector and memory T-cells. According to the conventional understanding of OX40 co-stimulation, an interaction between OX40 and OX40 ligand (OX40L) occurs when activated T-cells bind to professional antigen-presenting cells (APCs). The T-cell functions, including cytokine production, expansion, and survival, are then enhanced by the OX40 co-stimulatory signals. The interaction between OX40 and OX40L occurs during the T-cell-Dendritic cell (DC) interaction, 2-3 days after antigen recognition. The OX40-expressing T-cell may also interact with an OX40L-expressing cell other than DCs, and receive an OX40 signal from the cell, which may provide essential signals for the generation of memory T-cells, the enhancement of the Th2 response, and the prolongation of inflammatory responses. Thus, the optimal interaction between OX40 and OX40L might be formed in two steps: OX40L expressed on activated CD4 T-cells interacts with OX40 expressed on other responder CD4 T-cell, leading to the optimal generation of memory CD4 T cells (Soroosh et al., 2006) or OX40L expressed on CD4+ accessory cells may promote Th2 cell survival through the interaction with OX40 on Th2 cells (Kim et al. 2003). In addition, OX40L expression on B cells is required for in vivo Th2 development, but not Th1 development (Linton et al. 2003) and OX40L-expressing mast cells directly enhance effector T-cell function through the interaction between OX40 on T-cells and OX40L on mast cells (Kashiwakura et al. J Immunol 2004; 173: 5247-5257; Nakae et al. J Immunol 2006; 176: 2238-2248). In addition, as endothelial cells also express OX40L Omura et al. 1996), OX40 binding to endothelial cells might be involved in vascular inflammation. Excess OX40 signals, to both responder T-cells and T-regulatory cells, suppress Treg-mediated immune suppression. OX40 signals passing into responder T-cells render them resistant to Treg-mediated suppression. On the other hand, OX40 signals passing into Treg cells directly inhibit Treg-suppressive function, although it is controversial whether OX40 signals might control the Foxp3 expression level in Treg cells. In addition, deliberate OX40 stimulation inhibits the TGF-beta-dependent differentiation of iTreg cells (inducible Treg cells). The inhibition may be mediated in part by effector cytokines, such as IL-4 and IFN-gamma produced by effector T-cells stimulated with OX40. Importantly, blocking OX40L markedly promotes iTreg differentiation and induces graft tolerance, which might be mediated by Treg cells. Therefore, OX40 is a possible molecular target for controlling T-cell-mediated autoimmunity. Furthermore, recent studies reported that the interaction between OX40L expressed by mast cells and OX40 expressed by Treg cells may mutually suppress mast-cell function and Treg cell-suppressive function (Gri et al. 2008; Piconese et al. 2009).

Mice are the experimental tool of choice for immunologists, and the study of their immune responses has provided tremendous insight into the workings of the human immune system. The general structure of the mouse and human system seem to be quite similar; however, significant differences also exist. For example, in mice, CD134 is expressed on Teffs upon activation, whereas Tregs constitutively express CD134 (Piconese et al. J Exp Med 2008; 205: 825-839). In humans, CD134 is expressed on both Teffs and Tregs but only upon activation (see below, e.g., Example 2 (g), 'CD134 expression on human effector and regulatory T lymphocytes after stimulation with anti-human CD3/anti-human CD28 antibody stimulator beads'). Furthermore, mouse Tregs induce apoptosis of mouse Teffs to achieve suppression (Pandiyan et al. Nat Immunol 2007; 8: 1353; Scheffold et al. Nat Immunol 2007; 8: 1285-1287), whereas human Tregs do not induce apoptosis in human Teffs to achieve suppression (Vercoulen et al. Plos ONE 2009; 4: e7183). Collectively, these data indicate different roles of CD134 in the Tregs suppressive function between human and mouse immune systems.

The term "binding molecule" encompasses (1) an antibody, (2) an antigen-binding fragment of an antibody, and (3) a derivative of an antibody, each as defined herein. The term "binds to CD134" or "binding to CD134" refers to the binding of a binding molecule, as defined herein, to the CD134 receptor in an in vitro assay, such as a BIAcore assay or by Octet (surface plasmon resonance). The binding molecule preferably has a binding affinity ($K_d$) of $1\times10^{-6}$ M or less, more preferably less than $50\times10^{-7}$ M, still more preferably less than $1\times10^{-7}$ M.

The term "isolated antibody" or "isolated binding molecule" refers to an antibody or a binding molecule that: (1) is not associated with naturally associated components that accompany it in its native state; (2) is free of other proteins from the same species; (3) is expressed by a cell from a different species; or (4) does not occur in nature. Examples of isolated antibodies include an anti-CD134 antibody that has been affinity purified using CD134, an anti-CD134 antibody that has been generated by hybridomas or other cell lines in vitro, and a human anti-CD134 antibody derived from a transgenic animal.

The term "agonist" refers to a binding molecule, as defined herein, which upon binding to CD134, (1) stimulates or activates CD134, (2) enhances, promotes, induces, increases or prolongs the activity, presence or function of CD134, or (3) enhances, promotes, increases or induces the expression of CD134. The term "antagonist" refers to a binding molecule, as defined herein, which upon binding to CD134, (1) inhibits or suppresses CD134, (2) inhibits or suppresses an activity, presence or function of CD134, or (3) inhibits or suppresses the expression of CD134.

The term "antibody" refers to an immunoglobulin molecule that is typically composed of two identical pairs of polypeptide chains, each pair having one "heavy" (H) chain and one "light" (L) chain. Human light chains are classified as kappa (κ) and lambda (λ). Heavy chains are classified as mu, delta, gamma, alpha, or epsilon, and define the antibody's isotype as IgM, IgD, IgG, IgA, and IgE, respectively. Each heavy chain is comprised of a heavy chain variable region (abbreviated herein as HCVR or VH) and a heavy chain constant region. The heavy chain constant regions of IgD, IgG, and IgA are comprised of three domains, CH1, CH2 and CH3, and the heavy chain constant regions of IgM and IgE are comprised of four domains, CH1, CH2, CH3, and CH4. Each light chain is comprised of a light chain variable region (abbreviated herein as LCVR or VL) and a light chain constant region. The light chain constant region is comprised of one domain, CL. The constant regions of the antibodies may mediate the binding of the immunoglobulin to host tissues or factors, including various cells of the immune system (e.g., effector cells). The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from the amino-terminus to carboxy-terminus in the following order: FR1, CDR1, FR2, CDR2, FR3, CDR3, FR4. The variable regions of each heavy/light chain pair (VH and VL), respectively, form the antibody binding site. The assignment of amino acids to each region or domain is in accordance with the definitions of Kabat Sequences of Proteins of Immunological Interest (National Institutes of Health, Bethesda, Md. (1987 and 1991)) or in accordance with the definitions of Chothia et al. Conformations of immunoglobulin hypervariable regions (Nature 1989; 342(6252):877-83). The term "antibody" encompasses an antibody that is a multimeric form of antibodies, such as dimers, trimers, or higher-order multimers of monomeric antibodies. It also encompasses an antibody that is linked or attached to a non-antibody moiety. Further, the term "antibody" is not limited by any particular method of producing the antibody. For example, it includes monoclonal antibodies, recombinant antibodies and polyclonal antibodies.

The term "antibody derivative" or "derivative" of an antibody refers to a molecule that is capable of binding to the same antigen (i.e., human CD134) that the antibody binds to and comprises an amino acid sequence of the antibody linked to an additional molecular entity. The amino acid sequence of the antibody that is contained in the antibody derivative may be the full-length antibody, or may be any portion or portions of a full-length antibody. The additional molecular entity may be a biological or chemical molecule. Examples of additional molecular entities include chemical groups, peptides, proteins (such as enzymes, antibodies), amino acids, and chemical compounds. The additional molecular entity may be for use as a detection agent, marker label, therapeutic or pharmaceutical agent. The amino acid sequence of an antibody may be attached or linked to the additional entity by non-covalent association, chemical coupling, genetic fusion, or otherwise. The term "antibody derivative" also encompasses chimeric antibodies, humanized antibodies, and molecules that are derived from modifications of the amino acid sequences of a CD134 antibody, such as conservation amino acid substitutions, insertions and additions.

The term "antigen-binding fragment" of an antibody refers to one or more portions of a full-length antibody that retain the ability to bind to the same antigen (i.e., human CD134) that the antibody binds to. The term "antigen-binding fragment" also encompasses a portion of an antibody that is part of a larger molecule formed by non-covalent or covalent association or of the antibody portion with one or more additional molecular entities. Examples of additional molecular entities include amino acids, peptides, or proteins, such as the streptavidin core region, which may be used to make a tetrameric scFv molecule (Kipriyanov et al. Hum Antibodies Hybridomas 1995; 6(3): 93-101).

The term "chimeric antibody" refers to an antibody that comprises amino acid sequences derived from two or more different antibodies. The two or more different antibodies may be from the same species or from two or more different species.

The term "epitope" refers to the part of an antigen that is capable of specific binding to an antibody, or T-cell receptor or otherwise interacting with a molecule. "Epitope" is also referred to in the art as the "antigenic determinant". An epitope generally consists of chemically active surface groupings of molecules such as amino acids or carbohydrate or sugar side chains. An epitope may be "linear" or "non-linear/conformational". Once a desired epitope is determined (e.g., by epitope mapping), antibodies to that epitope can be generated. The generation and characterization of antibodies may also provide information about desirable epitopes. From this information, it is then possible to screen antibodies for those which bind to the same epitope e.g. by conducting cross-competition studies to find antibodies that competitively bind with one another, i.e., the antibodies compete for binding to the antigen.

The term "host cell" refers to a cell into which an expression vector has been introduced. The term encompasses not only the particular subject cell but also the progeny of such a cell. Because certain modifications may occur in successive generations due to either environmental influences or mutation, such progeny may not be identical to the parent cell, but are still included within the scope of the term "host cell."

The term "human antibody" refers to an antibody consisting of amino acid sequences of human immunoglobulin sequences only. A human antibody may contain murine carbohydrate chains if produced in a mouse, in a mouse cell or in a hybridoma derived from a mouse cell. Human antibodies may be prepared in a variety of ways known in the art.

The term "humanized antibody" refers to a chimeric antibody that contains amino acid residues derived from human antibody sequences. A humanized antibody may contain some or all of the CDRs from a non-human animal antibody while the framework and constant regions of the antibody contain amino acid residues derived from human antibody sequences.

The term "mammal" refers to any animal species of the Mammalian class. Examples of mammals include: humans; laboratory animals such as rats, mice, simians and guinea pigs; domestic animals such as rabbits, cattle, sheep, goats, cats, dogs, horses, and pigs and the like.

The term "isolated nucleic acid" refers to a nucleic acid molecule of genomic, cDNA, or synthetic origin, or a combination thereof, which is separated from other nucleic acid molecules present in the natural source of the nucleic acid. Preferably, an "isolated" nucleic acid is free of sequences located at the 5' and 3' ends of the nucleic acid of interest in the genomic DNA of the organism from which the nucleic acid is derived.

The term "off-rate" or "$K_d$" refers to the equilibrium dissociation constant of a particular antibody-antigen interaction and is used to describe the binding affinity between a ligand (such as an antibody) and a protein (such as CD134). The smaller the equilibrium dissociation constant, the more tightly bound the ligand is, or the higher the affinity between ligand and protein. A $K_d$ can be measured by surface plasmon resonance, for example using the BIACORE 1 or the Octet system. The term "anti-CD134 antibody" refers to an antibody, as defined herein, capable of binding to the human CD134.

The terms "OX40 receptor" and "CD134 receptor" are used interchangeably in the present application, and include the human CD134, as well as variants, isoforms, and species homologues thereof. Accordingly, human binding molecules disclosed herein may, in certain cases, also bind to the CD134 from species other than human. In other cases, the binding molecules may be completely specific for the human CD134 and may not exhibit species or other types of cross-reactivity. In particular, they will not bind to the mouse or rat CD134.

The term "specifically bind to the human CD134" means that the $K_d$ of a binding molecule for binding to human CD134, is preferably more than 10 fold, 50 fold or, most preferably, more than 100 fold the $K_d$ for its binding to, e.g., the human CD40, as determined using an assay described herein or known to one of skill in the art (e.g. a BIAcore assay). The determination that a particular agent binds specifically to the OX40 receptor may alternatively readily be made by using or adapting routine procedures. One suitable in vitro assay makes use of the Western blotting procedure (described in many standard texts, including "Antibodies, A Laboratory Manual" by Harlow and Lane). To determine that a given OX40 receptor binding agent binds specifically to the human OX40 protein, total cellular protein is extracted from mammalian cells that do not express the OX40 antigen, such as a non-lymphocyte cell (e.g., a COS cell or a CHO cell), transformed with a nucleic acid molecule encoding OX40. As a negative control, total cellular protein is also extracted from corresponding non-transformed cells. These protein preparations are then electrophorezed on a non-denaturing or denaturing polyacrylamide gel (PAGE). Thereafter, the proteins are transferred to a membrane (for example, nitrocellulose) by Western blotting, and the agent to be tested is incubated with the membrane. After washing the membrane to remove non-specifically bound agent, the presence of bound agent is detected by the use of an antibody raised against the test agent conjugated to a detection agent, such as the enzyme alkaline phosphatase; application of the substrate 5-bromo-4-chloro-3-indolyl phosphate/nitro blue tetrazolium results in the production of a dense blue compound by immuno-localized alkaline phosphatase. Agents which bind specifically to human OX40 will, by this technique, be shown to bind to the human OX40 band (which will be localized at a given position on the gel determined by its molecular mass) in the extract from OX40 transformed cells, whereas little or no binding will be observed in the extract from non-transformed cells. Non-specific binding of the agent to other proteins may occur and may be detectable as a weak signal on the Western blots. The nonspecific nature of this binding will be recognized by one skilled in the art by the weak signal obtained on the Western blot relative to the strong primary signal arising from the specific agent/human OX40 protein binding. Ideally, an OX40 receptor binding agent would not bind to the proteins extracted from the non-transformed cells. In addition to binding assays using extracted proteins, putative OX40 receptor binding agents may be tested to confirm their ability to bind substantially only OX40 receptor in vivo by conjugating the agent to a fluorescent tag (such as FITC) and analyzing its binding to antigen activated CD4+ T-cell and non-activated T-cell populations by Fluorescence Activated Cell Sorting (FACS). An agent which binds substantially only the OX40 receptor will stain only activated CD4+ T-cells.

The term "vector" refers to a nucleic acid molecule capable of transporting another nucleic acid molecule in a host cell. Examples of vectors include plasmids, viral vectors, cosmid or phage vectors, and naked DNA or RNA expression vectors. Some vectors are capable of autonomous replication in a host cell into which they are introduced. Some vectors can be integrated into the genome of a host cell upon introduction into the host cell, and thereby are replicated along with the host genome. Certain vectors are capable of directing the expression of genes to which they are operatively linked, and therefore may be referred to as "expression vectors."

As used herein, the twenty conventional amino acids and their abbreviations follow conventional usage.

The present invention provides isolated binding molecules that bind to the human CD134, including anti-CD134 antibodies, antigen-binding fragments of the anti-CD134 antibodies, and derivatives of the anti-CD134 antibodies. The binding molecules are characterized by at least one of the following functional properties: (a) bind to the human CD134 with a $K_d$ of $1\times10^{-6}$ M or less and (b) do not prevent human CD134 (OX40) receptor binding to OX40 ligand (OX40L); (c) have agonist activity on the human CD134 on T-effector cells and/or antagonistic activity on the human CD134 on T-regulatory cells; (d) do not bind to CD40 receptor at concentration up to 500 nM; (e) do not bind to CD137 receptor at concentrations up to 500 nM; (f) do not bind to CD271 receptor at concentrations up to 500 nM; (g) are capable of enhancing IL-2 production by isolated human T cells; (h) are capable of enhancing immune response; (i) are capable of inhibiting tumour cell growth; and (j) have therapeutic effect on a cancer. In some embodiments the binding molecule binds to the human CD134 with a $K_d$ of $1\times10^{-7}$ M or less, or $1\times10^{-8}$ M or less, or $5\times1\times10^{-9}$ M or less.

Antibodies and other binding molecules of the invention may be prepared by conventional techniques and then screened in order to identify and obtain binding molecules that do not prevent binding of OX40L to CD134. For example, binding molecules that bind CD134 even when the CD134 has been exposed to a saturating concentration of OX40L may be selected.

In an embodiment of the present invention is provided a human antibody that binds to the human CD134. In some embodiments, the human antibody is a monoclonal antibody that specifically binds to the human CD134 with a $K_d$ of 100 nM or less, preferably 10 nM or less, and/or has agonist activity on the human CD134 of T-effector cells and/or antagonist activity of human CD134 T-regulatory cells. One example of such human antibodies is the human monoclonal antibody clone 12H3. The amino acid sequence of the whole heavy chain variable region and the amino acid sequences of the three CDRs of the variable region of the heavy chain (VH) of antibody clone 12H3 are shown in SEQ ID NOs: 12 and 14-16, respectively. The amino acid sequence of the whole light chain variable region and the amino acid sequences of the three CDRs of the variable region of the light chain (VL) of antibody clone 12H3 are shown in SEQ ID NOs: 13 and 17-19, respectively. Another illustrative antibody of the disclosure is the human monoclonal antibody clone 20E5. The amino acid sequence of the whole heavy chain variable region and the amino acid sequences of the three CDRs of the variable region of the heavy chain (VH) of antibody clone 20E5 are shown in SEQ ID NOs: 4 and 6-8, respectively. The amino acid sequence of the whole light chain variable region and the amino acid sequences of the three CDRs of the variable region of the light chain (VL) of antibody clone 20E5 are shown in SEQ ID NOs: 5 and 9-11, respectively.

The antibodies of the invention can comprise one or more of these CDRs, or one or more of these CDRS with 1, 2 or 3 amino acid substitutions per CDR. The substitutions are preferably 'conservative' ones. Conservative substitutions providing functionally similar amino acids are well known in the art, and are described for example in Table 1 of WO 2010/019702, which is incorporated herein by reference.

Given that clone 12H3 and clone 20E5 bind to the human CD134, the VH and VL sequences of each of them can be "mixed and matched" with other anti-CD134 antibodies to create additional antibodies. The binding of such "mixed and matched" antibodies to the human CD134 can be tested using the binding assays known in the art, including an assay described in the Examples. In one case, when VH and VL regions are mixed and matched, a VH sequence from a particular VH/VL pairing is replaced with a structurally similar VH sequence. Likewise, in another case a VL sequence from a particular VH/VL pairing is replaced with a structurally similar VL sequence.

Molecules containing only one or two CDR regions (in some cases, even just a single CDR or a part thereof, especially CDR3) are capable of retaining the antigen-binding activity of the antibody from which the CDR(s) are derived. See, for example, Laune et al. JBC 1997; 272: 30937-44; Monnet et al. JBC 1999; 274:3789-96; Qiu et al. Nature Biotechnology 2007; 25: 921-9; Ladner et al. Nature Biotechnology 2007; 25: 875-7; Heap et al. J Gen Virol 2005; 86: 1791-1800; Nicaise et al. Protein Science 2004; 13: 1882-91; Vaughan and Sollazzo Combinatorial Chemistry & High Throughput Screening 2001; 4:417-430; Quiocho Nature 1993; 362: 293-4; Pessi et al. Nature 1993; 362: 367-9; Bianchi et al. J Mol Biol 1994; 236: 649-59; and Gao et al. J Biol Chem 1994; 269: 32389-93.

Accordingly, one embodiment of the present invention is an isolated anti-human CD134 antibody that comprises: (a) a heavy chain variable region comprising the amino acid sequence of SEQ ID NO: 12; (b) a light chain variable region comprising the amino acid sequence of SEQ ID NO: 13.

In a further embodiment according to the invention is provided an isolated CD134 binding molecule that comprises: (a) a heavy chain CDR1 comprising the amino acid sequence of SEQ ID NO: 14; and/or (b) a heavy chain CDR2 comprising the amino acid sequence of SEQ ID NO: 15; and/or (c) heavy chain CDR3 comprising the amino acid sequence of SEQ ID NO: 16.

In a further embodiment according to the invention is provided an isolated CD134 binding molecule that comprises (a) a light chain CDR1 comprising the amino acid sequence of SEQ ID NO: 17; and/or (b) a light chain CDR2 comprising the amino acid sequence of SEQ ID NO: 18; and/or (c) a light chain CDR3 comprising the amino acid sequence of SEQ ID NO: 19.

Accordingly, one embodiment of the present invention is an isolated anti-human CD134 antibody that comprises: (a) a heavy chain variable region comprising the amino acid sequence of SEQ ID NO: 4; (b) a light chain variable region comprising the amino acid sequence of SEQ ID NO: 5.

In a further embodiment according to the invention is provided an isolated CD134 binding molecule that comprises: (a) a heavy chain CDR1 comprising the amino acid sequence of SEQ ID NO: 6; and/or (b) a heavy chain CDR2 comprising the amino acid sequence of SEQ ID NO: 7; and/or (c) heavy chain CDR3 comprising the amino acid sequence of SEQ ID NO: 8.

In a further embodiment according to the invention is provided an isolated CD134 binding molecule that comprises (a) a light chain CDR1 comprising the amino acid sequence of SEQ ID NO: 9; and/or (b) a light chain CDR2 comprising the amino acid sequence of SEQ ID NO: 10; and/or (c) a light chain CDR3 comprising the amino acid sequence of SEQ ID NO: 11.

Given that clone 12H3 and clone 20E5 bind to the human CD134 and that antigen-binding specificity is provided primarily by the CDR1, CDR2, and CDR3 regions, the VH CDR1, CDR2, and CDR3 sequences and VL CDR1, CDR2, and CDR3 sequences can be "mixed and matched" to create additional anti-CD134 antibodies. For example, CDRs from different anti-CD134 antibodies can be mixed and matched, although each antibody will typically contain a VH CDR1, CDR2, and CDR3 and a VL CDR1, CDR2, and CDR3. The binding of such "mixed and matched" antibodies to the CD134 can be tested using the binding assays described above and in the Examples (e.g., ELISAs, Biacore analysis). In one case, when VH CDR sequences are mixed and matched, the CDR1, CDR2 and/or CDR3 sequence from a particular VH sequence is replaced with structurally similar CDR sequence(s). Likewise, when VL CDR sequences are mixed and matched, the CDR1, CDR2 and/or CDR3 sequence from a particular VL sequence typically is replaced with a structurally similar CDR sequence(s). It will be readily apparent to an ordinarily skilled artisan that novel VH and VL sequences can be created by replacing one or more VH and/or VL CDR region sequences with structurally similar sequences from the CDR sequences disclosed herein.

The class (e.g., IgG, IgM, IgE, IgA, or IgD) and subclass (e.g., IgG1, IgG2, IgG3, or IgG4) of the anti-CD134 antibodies may be determined by any suitable method such as by ELISA or Western Blot as well as other techniques. Alternatively, the class and subclass may be determined by sequencing all or a portion of the constant domains of the heavy and/or light chains of the antibodies, comparing their amino acid sequences to the known amino acid sequences of various class and subclasses of immunoglobulins, and determining the class and subclass of the antibodies. The anti-CD134 antibodies can be an IgG, an IgM, an IgE, an IgA, or an IgD molecule. For example, the anti-CD134 antibodies can be an IgG that is an IgG1, IgG2, IgG3, or an IgG4 subclass. Thus, another aspect of the invention provides a method for converting the class or subclass of an anti-CD134 antibody to another class or subclass.

The binding molecules according to an embodiment of the invention include monoclonal antibodies, fragments thereof, peptides and other chemical entities. Monoclonal antibodies can be made by the conventional method of immunization of a mammal, followed by isolation of plasma B cells producing the monoclonal antibodies of interest and fusion with a myeloma cell.

In various embodiments, instead of being an actual antibody, the binding moiety may be an antibody mimic (for example, based upon a non-antibody scaffold), an RNA aptamer, a small molecule or a CovX-body.

It will be appreciated that antibody mimics (for example, non-antibody scaffold structures that have a high degree of stability yet allow variability to be introduced at certain positions) may be used to create molecular libraries from which binding moieties can be derived. Those skilled in the arts of biochemistry will be familiar with many such molecules. Such molecules may be used as a binding moiety in the agent of the present invention.

Exemplary antibody mimics are discussed in Skerra et al. (2007, Curr. Opin. Biotech., 18: 295-304) and include: affibodies (also called Trinectins; Nygren, 2008, FEBS J, 275, 2668-2676); CTLDs (also called Tetranectins; Innovations Pharmac. Technol. (2006), 27-30; adnectins (also called monobodies; Meth. Mol. Biol., 352 (2007), 95-109); anticalins (Drug Discovery Today (2005), 10, 23-33); DARPins (ankyrins; Nat. Biotechnol. (2004), 22, 575-582); avimers (Nat. Biotechnol. (2005), 23, 1556-1561); microbodies (FEBS J, (2007), 274, 86-95); peptide aptamers (Expert. Opin. Biol. Ther. (2005), 5, 783-797); Kunitz domains (J. Pharmacol. Exp. Ther. (2006) 318, 803-809); affilins (Trends. Biotechnol. (2005), 23, 514-522).

Accordingly, it is preferred that the antibody mimic is selected from the group comprising or consisting of affibodies, tetranectins (CTLDs), adnectins (monobodies), anticalins, DARPins (ankyrins), avimers, iMabs, microbodies, peptide aptamers, Kunitz domains, aptamers and affilins.

By "small molecule" we mean a low molecular weight organic compound of 900 Daltons or less. Although large biopolymers such as nucleic acids, proteins, and polysaccharides (such as starch or cellulose) are not included as "small molecules", their constituent monomers (ribo- or deoxyribonucleotides, amino acids, and monosaccharides, respectively) and oligomers (i.e. short polymers such as dinucleotides, peptides such as the antioxidant glutathione, and disaccharides such as sucrose) are included. The production of small molecules is described in Mayes & Whitcombe, 2005, Adv. Drug Deliv. Rev. 57:1742-78 and Root-Bernstein & Dillon, 2008, Curr. Pharm. Des. 14:55-62.

CovX-Bodies are created by covalently joining a pharmacophore via a linker to the binding site of a specially-designed antibody, effectively reprogramming the antibody (Tryder et al., 2007, Bioorg. Med. Chem. Lett., 17:501-6). The result is a new class of chemical entities that is formed where each component contributes desirable traits to the intact CovX-Body—in particular, the entity has the biologic actions of the peptide and the extended half-life of the antibody.

Human antibodies can be made by several different methods, including by use of human immunoglobulin expression libraries (Stratagene Corp., La Jolla, Calif.; Cambridge Antibody Technology Ltd., London, England) to produce fragments of human antibodies (VH, VL, Fv, Fd, Fab, or (Fab')$_2$), and use of these fragments to construct whole human antibodies by fusion of the appropriate portion thereto, using techniques similar to those for producing chimeric antibodies. Human antibodies can also be produced in transgenic mice with a human immunoglobulin genome. Such mice are available from e.g. Abgenix, Inc., Fremont, Calif., and Medarex, Inc., Annandale, N.J. In addition to connecting the heavy and light chain Fv regions to form a single chain peptide, Fab can be constructed and expressed by similar means (M. J. Evans et al. J Immunol Meth 1995; 184: 123-138).

DeImmunized™ antibodies are antibodies in which potentially immunogenic T cell epitopes have been eliminated, as described in International Patent Application PCT/GB98/01473. Therefore, immunogenicity in humans is expected to be eliminated or substantially reduced when they are applied in vivo. The immunoglobulin-based binding molecules of the invention may have their immunogenic T cell epitopes (if present) eliminated by means of such methods.

All of the wholly and partially human antibodies described above are less immunogenic than wholly murine or non-human-derived antibodies, as are the fragments and single chain antibodies. All these molecules (or derivatives thereof) are therefore less likely to evoke an immune or allergic response. Consequently, they are better suited for in vivo administration in humans than wholly non-human antibodies, especially when repeated or long-term administration is necessary.

Bispecific antibodies can be used as cross-linking agents between human CD134 of the same human target cell, or human CD134 on two different human target cells. Such bispecific antibodies have one specificity for each of two different epitopes on human CD134. These antibodies and the method of making them are described in U.S. Pat. No. 5,534,254 (Creative Biomolecules, Inc.). Different embodiments of bispecific antibodies described in the patent include linking single chain Fv with peptide couplers, including Ser-Cys, (Gly)$_4$-Cys (SEQ ID NO: 62), (His)$_6$-(Gly)$_4$-Cys (SEQ ID NO: 63), chelating agents, and chemical or disulfide couplings including bismaleimidohexane and bismaleimidocaproyl.

Non-antibody molecules can be isolated or screened from compound libraries by conventional means. An automated system for generating and screening a compound library is described in U.S. Pat. Nos. 5,901,069 and 5,463,564. A more focused approach involves three-dimensional modelling of the binding site, and then making a family of molecules which fit the model. These are then screened for those with optimal binding characteristics.

Another approach is to generate recombinant peptide libraries, and then screen them for those which bind to the epitope of human CD134 of interest. See, for example, U.S. Pat. No. 5,723,322. This epitope is the same as that bound by the monoclonal antibodies described in the examples below. Molecules can, in fact, be generated or isolated with relative ease in accordance with techniques well known in the art once the epitope is known.

A further embodiment provides derivatives of any of the anti-CD134 antibodies as described above. In one particular aspect, the antibody derivative is derived from modifications of the amino acid sequences of clone 12H3 and/or clone 20E5. Amino acid sequences of any regions of the antibody chains may be modified, such as framework regions, CDR regions, or constant regions. The modifications can be introduced by standard techniques known in the art, such as site-directed mutagenesis and random PCR-mediated mutagenesis, and may comprise natural as well as non-natural amino acids. Types of modifications include insertions, deletions, substitutions, or combinations thereof, of one or more amino acids of an anti-CD134 antibody. In some embodiments, the antibody derivative comprises 1, 2, 3, or 4 amino acid substitutions in the heavy chain CDRs and/or one amino acid substitution in the light chain CDRs. In some embodiments, a derivative of an anti-CD134 antibody comprises one or more amino acid substitutions relative to the germ line amino acid sequence of the human gene. In a particular embodiment, one or more of those substitutions from germ line is in the CDR2 region of the heavy chain. In another particular embodiment, the amino acid substitutions relative to the germline are at one or more of the same positions as the substitutions relative to germ line in antibodies clone 12H3 and clone 20E5. In another embodiment, the amino acid substitution is to change one or more cysteines in an antibody to another residue, such as, without limitation, alanine or serine. The cysteine may be a canonical or non-canonical cysteine. The substitution can be made in a CDR or framework region of a variable domain or in the constant domain of an antibody. Another type of amino acid substitution is to eliminate asparagine-glycine pairs, which form potential deamidation sites, by altering one or both of the residues. In still other embodiments, the amino acid substitution is a conservative amino acid substitution. In one embodiment, the antibody derivative has 1, 2, 3, or 4 conservative amino acid substitutions in the heavy chain CDR regions relative to the amino acid sequences of clone 12H3 and/or clone 20E5. Another type of modification of an anti-CD134 antibody is the alteration of the original glycosylation pattern of the antibody. The term "alteration" refers to deletion of one or more carbohydrate moieties found in the antibody, and/or adding one or more glycosylation sites that are not present in the antibody.

Glycosylation of antibodies is typically N-linked. N-linked refers to the attachment of the carbohydrate moiety to the side chain of an asparagine residue. Examples of other modifications include acylation, amidation, acetylation, cross-linking, cyclization, formylation, hydroxylation, iodination, methylation, myristoylation, disulfide bond formation, demethylation, formation of covalent cross-links, formation of cysteine, oxidation, phosphorylation, prenylation, pegylation, proteolytic processing and sulfation.

A further embodiment provides an antibody derivative that comprises an anti-CD134 antibody, or antigen-binding fragment thereof, as described herein, linked to an additional molecular entity. Examples of additional molecular entities include pharmaceutical agents, peptides or proteins, and detection agents or labels. Specific examples of pharmaceutical agents that may be linked to an anti-CD134 antibody include cytotoxic agents or other cancer therapeutic agents, and radioactive isotopes. Specific examples of peptides or proteins that may be linked to an anti-CD134 antibody include antibodies, which may be the same anti-CD134 antibody or a different antibody. Specific examples of detection agents or labels that may be linked to an anti-CD134 antibody include (1) fluorescent compounds, such as fluorescein, fluorescein isothiocyanate, phycoerythrin, rhodamine, 5-dimethylamine-1-naphthalenesulfonyl chloride and lanthanide phosphors; (2) enzymes, such as horseradish peroxidase, alkaline phosphatase, luciferase, and glucose oxidase; (3) biotin; (4) a predetermined polypeptide epitope recognized by a secondary reporter, such as leucine zipper pair sequences, metal binding domains, epitope tags and binding sites for secondary antibodies. A further embodiment provides an antibody derivative which is a multimeric form of an anti-CD134 antibody, such as antibody dimers, trimers, or higher-order multimers of monomeric antibodies. Individual monomers within an antibody multimer may be identical or different, i.e., they may be heteromeric or homomeric antibody multimers. Multimerization of antibodies may be accomplished through natural aggregation. For example, some percentage of purified antibody preparations (e.g., purified IgG1 molecules) spontaneously form protein aggregates containing antibody homodimers, and other higher-order antibody multimers. Alternatively, antibody homodimers may be formed through chemical linkage techniques known in the art. Suitable crosslinkers include those that are heterobifunctional, such as m-maleimidobenzoyl-N-hydroxysuccinimide ester, N-succinimidyl S-acethylthio-acetate and succinimidyl 4-(maleimidomethyl)cyclohexane-1-carboxylate) or homobifunctional (such as disuccinimidyl suberate). Such linkers are commercially available. Antibodies can also be made to multimerize through recombinant DNA techniques known in the art.

A yet further embodiment provides an antibody derivative which is a chimeric antibody, comprising an amino acid sequence of a anti-human CD134 antibody described herein above. In another example, all of the CDRs of the chimeric antibody are derived from anti-human CD134 antibodies. In another example, the CDRs from more than one anti-human CD134 antibody are combined in a chimeric antibody. Further, a chimeric antibody may comprise the framework regions derived from one anti-human CD134 antibody and one or more CDRs from one or more different human antibodies. Chimeric antibodies can be generated using conventional methods known in the art. In some particular embodiments, the chimeric antibody comprises one, two, or three CDRs from the heavy chain variable region or from the light chain variable region of an antibody selected from antibody clone 12H3 and/or clone 20E5.

Examples of other antibody derivatives provided by the present invention include single chain antibodies, diabodies, domain antibodies, nanobodies, and unibodies. In preferred embodiments, the monoclonal antibodies may be chimeric antibodies, humanized antibodies, human antibodies, DeImmunized™ antibodies, single-chain antibodies, fragments, including Fab, F(ab')$_2$, Fv or other fragments which retain the antigen binding function of the parent antibody. Single chain antibodies ("ScFv") and the method of their construction are described in U.S. Pat. No. 4,946,778.

A "single-chain antibody" (scFv) consists of a single polypeptide chain comprising a VL domain linked to a VH domain wherein VL domain and VH domain are paired to form a monovalent molecule. Single chain antibody can be prepared according to method known in the art (see, for example, Bird et al., (1988) Science 242:423-426 and Huston et al., (1988) Proc. Natl. Acad. Sci. USA 85:5879-5883). A "diabody" consists of two chains, each chain comprising a heavy chain variable region connected to a light chain variable region on the same polypeptide chain connected by a short peptide linker, wherein the two regions on the same chain do not pair with each other but with complementary domains on the other chain to form a bispecific molecule. Methods of preparing diabodies are known in the art (See, e.g., Holliger P. et al., (1993) Proc. Natl. Acad. Sci. USA 90:6444-6448, and Poljak R. J. et al., (1994) Structure 2:1121-1123). Domain antibodies (dAbs) are small functional binding units of antibodies, corresponding to the variable regions of either the heavy or light chains of antibodies. Domain antibodies are well expressed in bacterial, yeast, and mammalian cell systems. Further details of domain antibodies and methods of production thereof are known in the art (see, for example, U.S. Pat. Nos. 6,291,158; 6,582,915; 6,593,081; WO04/003019 and WO03/002609). Nanobodies are derived from the heavy chains of an antibody. A nanobody typically comprises a single variable domain and two constant domains (CH2 and CH3) and retains antigen-binding capacity of the original antibody. Nanobodies can be prepared by methods known in the art (see e.g., U.S. Pat. No. 6,765,087, U.S. Pat. No. 6,838,254, WO 06/079372). Unibodies consist of one light chain and one heavy chain of an IgG4 antibody. Unibodies may be made by the removal of the hinge region of IgG4 antibodies. Further details of unibodies and methods of preparing them may be found in WO2007/059782.

In addition to the binding moiety, the molecules of the invention may further comprise a moiety for increasing the in vivo half-life of the molecule, such as but not limited to polyethylene glycol (PEG), human serum albumin, glycosylation groups, fatty acids and dextran. Such further moieties may be conjugated or otherwise combined with the binding moiety using methods well known in the art.

A further aspect of the invention provides a nucleic acid molecule encoding an amino acid sequence of a CD134-binding binding molecule according to the first aspect of the invention. The amino acid sequence encoded by the nucleic acid molecule may be any portion of an intact antibody, such as a CDR, a sequence comprising one, two, or three CDRs, or a variable region of a heavy chain or light chain, or may be a full-length heavy chain or light chain. In some embodiments, the nucleic acid molecule encodes an amino acid sequence that comprises (1) a CDR3 region, particularly a heavy chain CDR3 region, of antibodies clone 12H3 and/or clone 20E5; (2) a variable region of a heavy chain or variable region of a light chain of antibodies clone 12H3 and/or clone 20E5; or (3) a heavy chain or a light chain of antibodies clone 12H3 and/or clone 20E5. In other embodiments, the nucleic acid molecule encodes a polypeptide that comprises an amino acid sequence selected from the group consisting of SEQ ID NOs: 12, 13, 14, 15, 16, 17, 18 or 19, or from the group consisting of SEQ ID NOs: 4, 5, 6, 7, 8, 9, 10 or 11.

The nucleic acid molecules provided by the disclosure may be obtained from any source that produces a CD134 antibody in accordance with the invention. mRNA from anti-CD134 antibody-producing cells may be isolated by standard techniques, cloned and/or amplified using PCR and library construction techniques, and screened using standard protocols to obtain nucleic acid molecules encoding an amino acid sequence of an anti-CD134 antibody. The mRNA may be used to produce cDNA for use in the polymerase chain reaction (PCR) or cDNA cloning of antibody genes. In one embodiment, the nucleic acid molecule is obtained from a hybridoma that expresses an anti-CD134 antibody, as described above, preferably a hybridoma that has as one of its fusion partners a non-human transgenic animal cell that expresses human immunoglobulin genes. In another embodiment, the hybridoma is derived from a non-human, non-transgenic animal.

A nucleic acid molecule encoding the heavy chain of an anti-CD134 antibody may be constructed by fusing a nucleic acid molecule encoding the heavy variable region with a nucleic acid molecule encoding a constant region of a heavy chain. Similarly, a nucleic acid molecule encoding the light chain of an anti-CD134 antibody may be constructed by fusing a nucleic acid molecule encoding the light chain variable region with a nucleic acid molecule encoding a constant region of a light chain. The nucleic acid molecules encoding the VH and VL chain may be converted to full-length antibody genes by inserting them into expression vectors already encoding heavy chain constant and light chain constant regions, respectively, such that the VH segment is operatively linked to the heavy chain constant region (CH) segment(s) within the vector and the VL segment is operatively linked to the light chain constant region (CL) segment within the vector. Alternatively, the nucleic acid molecules encoding the VH or VL chains are converted into full-length antibody genes by linking, e.g., ligating, the nucleic acid molecule encoding a VH chain to a nucleic acid molecule encoding a CH chain using standard molecular biological techniques. The same may be achieved using nucleic acid molecules encoding VL and CL chains. Nucleic acid molecules encoding the full-length heavy and/or light chains may then be expressed from a cell into which they have been introduced and the anti-CD134 antibody isolated.

The nucleic acid molecules may be used to recombinantly express large quantities of anti-CD134 antibodies, as described below. The nucleic acid molecules may also be used to produce other binding molecules provided by the disclosure, such as chimeric antibodies, single chain antibodies, immunoadhesins, diabodies, mutated antibodies, and antibody derivatives, as described elsewhere herein. In one embodiment, a nucleic acid molecule is used as probe or PCR primer for specific antibody sequences. For instance, a nucleic acid molecule probe may be used in diagnostic methods or a nucleic acid molecule PCR primer may be used to amplify regions of DNA that could be used, inter alia, to isolate nucleic acid sequences for use in producing variable regions of the anti-CD134 antibodies.

Once DNA molecules encoding the VH and VL segments of an anti-CD134 antibody are obtained, these DNA molecules can be further manipulated by recombinant DNA techniques, for example to convert the variable region genes to full-length antibody chain genes, to Fab fragment genes, or to a scFv gene.

A further aspect of the invention provides a vector, which comprises a nucleic acid molecule described herein above. The nucleic acid molecule may encode a portion of a light chain or heavy chain (such as a CDR or a variable region), a full-length light or heavy chain, polypeptide that comprises a portion or full-length of a heavy or light chain, or an amino acid sequence of an antibody derivative or antigen-binding fragment.

An example of a suitable expression vector is one that encodes a functionally complete human CH or CL immunoglobulin sequence, with appropriate restriction sites engineered so that any VH or VL sequence can be inserted and expressed. The expression vector also can encode a signal peptide that facilitates secretion of the amino acid sequence of the antibody chain from a host cell. The DNA encoding the amino acid sequence of an antibody chain may be cloned into the vector such that the signal peptide is linked in-frame to the amino terminus of the amino acid sequence of the antibody chain. The signal peptide can be an immunoglobulin signal peptide or a heterologous signal peptide (i.e., a signal peptide from a non-immunoglobulin protein). In addition to the nucleic acid sequence encoding an amino acid sequence of an anti-CD134 antibody (antibody chain genes), the expression vectors carry regulatory sequences that control the expression of the antibody chain genes in a host cell. The design of the expression vector, including the selection of regulatory sequences, may depend on such factors as the choice of the host cell to be transformed, the level of expression of protein desired, and so forth. Regulatory sequences for mammalian host cell expression include viral elements that direct high levels of protein expression in mammalian cells, such as promoters and/or enhancers derived from retroviral LTRs, cytomegalovirus (CMV) (such as the CMV promoter/enhancer), Simian Virus 40 (SV40) (such as the SV40 promoter/enhancer), adenovirus, (e.g., the adenovirus major late promoter (AdMLP)), polyoma and strong mammalian promoters such as native immunoglobulin and actin promoters.

The host cell may be a mammalian, insect, plant, bacterial, or yeast cell. Examples of mammalian cell lines suitable as host cells include Chinese hamster ovary (CHO) cells, NSO cells, PER-C6 cells, SP2 cells, HEK-293T cells, NIH-3T3 cells, HeLa cells, baby hamster kidney (BHK) cells, African green monkey kidney cells (COS), human hepatocellular carcinoma cells (e.g., Hep G2), human lung cells, A549 cells, and a number of other cell lines. Examples of insect cell lines include Sf9 or Sf21 cells. Examples of plant host cells include *Nicotiana, Arabidopsis*, duckweed, corn, wheat, potato, and so forth. Bacterial host cells include *E. coli* and *Streptomyces* species. Examples of yeast host cells include *Saccharomyces cerevisiae* and *Pichia pastoris*.

Amino acid sequences of a binding molecule expressed by different cell lines or in transgenic animals may have different glycosylation. However, all binding molecules encoded by the nucleic acid molecules provided herein, or comprising the amino acid sequences provided herein are part of the present invention, regardless of the glycosylation of the binding molecules.

Another aspect of the invention provides a method for producing a CD134-binding molecule as defined above using phage display. The method comprises (a) synthesizing a library of human antibodies on phage, (b) screening the library with the CD134 or a portion thereof, (c) isolating phage that binds the CD134 or a portion thereof, and (d) obtaining the antibody from the phage. One exemplary method for preparing the library of antibodies comprises the step of: (a) immunizing a non-human animal comprising human immunoglobulin loci with CD134 or an antigenic portion thereof to create an immune response; (b) extracting antibody-producing cells from the immunized animal; (c) isolating RNA encoding heavy and light chains of the anti-CD134 antibodies from the extracted cells; (d) reverse transcribing the RNA to produce cDNA; (e), amplifying the cDNA; and (f) inserting the cDNA into a phage display vector such that antibodies are expressed on the phage. Recombinant anti-human CD134 antibodies or antigen binding fragments thereof can be isolated by screening a recombinant combinatorial antibody library. The library may be a scFv phage display library, generated using human VL and VH cDNAs prepared from mRNA isolated from B cells. Methods for preparing and screening such libraries are known in the art. Kits for generating phage display libraries are commercially available.

In a preferred embodiment according to the invention is provided a composition, e.g., a pharmaceutical composition, containing one or a combination of binding molecules as described herein, and optionally a pharmaceutically acceptable carrier. The compositions can be prepared by conventional methods known in the art. In some embodiments, the composition comprises an anti-CD134 antibody or an antigen-binding fragment thereof. In a particular embodiment, the composition comprises antibody clone 12H3 and/or clone 20E5, or an antigen-binding fragment of either antibody. In still other embodiments, the composition comprises a derivative of antibody clone 12H3 and/or clone 20E5. The term "pharmaceutically acceptable carrier" refers to any inactive substance that is suitable for use in a formulation for the delivery of a binding molecule. A carrier may be an antiadherent, binder, coating, disintegrant, filler or diluent, preservative (such as antioxidant, antibacterial, or antifungal agent), sweetener, absorption delaying agent, wetting agent, emulsifying agent, buffer, and the like.

Non-peptide molecules of the invention could be administered orally, including by suspension, tablets and the like. Liquid formulations could be administered by inhalation of lyophilized or aerosolized microcapsules. Suppositories could also be used. Additional pharmaceutical vehicles could be used to control the duration of action of the molecules of the invention. The dosage and scheduling for the formulation, which is selected can be determined by standard procedures, well known in the art. Such procedures involve extrapolating an estimated dosing schedule from animal models, and then determining the optimal dosage in a human clinical dose ranging study.

The compositions may be in any suitable forms, such as liquid, semi-solid, and solid dosage forms. The various dosage forms of the compositions can be prepared by conventional techniques known in the art.

The relative amount of a binding molecule included in the composition will vary depending upon a number of factors, such as the desired release and pharmacodynamic characteristics, the specific binding molecule and carriers used and dosage form. The amount of a binding molecule in a single dosage form will generally be that amount which produces a therapeutic effect, but may also be a lesser amount. Generally, this amount will range from about 0.001 percent to about 99 percent, from about 0.1 percent to about 70 percent, or from about 1 percent to about 30 percent relative to the total weight of the dosage form.

In addition to the binding molecule, one or more additional therapeutic agents may be included in the composition or separately as part of the same treatment regime. Examples of the additional therapeutic agents are described herein below. The suitable amount of the additional therapeutic agent to be included in the composition can be readily selected by a person skilled in the art, and will vary depending on a number of factors, such as the particular agent and carriers used, dosage form, and desired release and pharmacodynamic characteristics. The amount of the additional therapeutic agent included in a single dosage form will generally be that amount of the agent which produces a therapeutic effect, but may be a lesser amount as well.

Binding molecules and pharmaceutical compositions comprising a binding molecule provided by the present disclosure are useful for therapeutic, diagnostic, or other purposes, such as enhancing an immune response, treating cancer, enhancing efficacy of other cancer therapy, or enhancing vaccine efficacy, and have a number of utilities, such as for use as medicaments or diagnostic agents. Thus, in preferred aspect, of the invention is provided methods of using the binding molecules or pharmaceutical compositions.

A further aspect of the invention provides a method for modulation of human CD134-mediated anti-tumour immune responses, including enhancement of human CD134 expressing human Teffs effector function and/or attenuation of human CD134 expressing human Tregs suppressive function, using binding molecules that bind to human CD134, including anti-human CD134 antibodies, which (1) circumvent the interaction of naturally occurring human OX40L with the human CD134 receptor and/or (2) do not block human CD134-mediated cell signalling after occupancy with its natural occurring human OX40L.

Another aspect of the invention provides a method of modulation of human CD134-mediated anti-tumour immune responses, whereby said method does not include binding molecules that bind to human CD134, including anti-human CD134 antibodies, such as human OX40L mimetics, which interact with human OX40L binding domain on the human CD134 receptor and/or block human OX40L-human CD134 cell signalling.

The present invention discloses binding molecules that bind to human CD134, including anti-human CD134 antibodies, for anti-tumour therapeutic purposes. The anti-human CD134 antibodies bind to the extracellular domain of human CD134. More specifically, the anti-human CD134 antibodies bind to non-OX40L-binding regions (i.e. the anti-human CD134 antibodies do not completely block the binding of human OX40L to human CD134) on the extracellular domain of human CD134 on activated human Teffs and human Tregs.

In one particular aspect, methods are provided for enhancing immune response in a mammal, comprising administering to the mammal a therapeutically effective amount of a binding molecule as described herein. In some embodiments, the binding molecule is an anti-CD134 antibody or antigen-binding fragment thereof and the mammal is a human. In a further embodiment, the binding molecule is antibody clone 12H3 and/or clone 20E5, or an antigen-binding fragment of either antibody. The term "enhancing immune response", means stimulating, evoking, increasing, improving, or augmenting any response of a mammal's immune system. The immune response may be a cellular response (i.e. cell-mediated, such as cytotoxic T lymphocyte mediated) or a humoral response (i.e. antibody mediated response), and may be a primary or secondary immune response. Examples of enhancement of immune response include increased CD4+ helper T cell activity and generation of cytolytic T cells. The enhancement of immune response can be assessed using a number of in vitro or in vivo measurements known to those skilled in the art, including, but not limited to, cytotoxic T lymphocyte assays, release of cytokines (for example IL-2 production), regression of tumours, survival of tumour bearing animals, antibody production, immune cell proliferation, expression of cell surface markers, and cytotoxicity. In one embodiment, the method enhances a cellular immune response, particularly a cytotoxic T cell response.

One aspect of the invention provides a binding molecule that binds to human CD134, wherein at or above the saturation concentration of said binding molecule, the effect on binding of OX40L to CD134 is reduced by not more than 70%, on human CD134 expressing T-cells, as measured by a fluorescence-based flow cytometric assay, as described in Example 2(f). More preferably, the effect on binding of OX40L to CD134 is reduced by not more than about 60%, or about 50%, or about 40%, or about 30%, or about 20%, or about 10% or less, or preferably no reduction in binding at all.

Another aspect of the invention provides a binding molecule wherein at a concentration of 70 nM of the binding molecule, the effect on binding of OX40L to CD134 is reduced by not more than 70% on human CD134 expressing T-cells, as measured by a fluorescence-based flow cytometric assay, as described in Example 2(f). More preferably, the effect on binding of OX40L to CD134 is reduced by not more than about 60%, or about 50%, or about 40%, or about 30%, or about 20%, or about 10% or less, or preferably no reduction in binding at all.

Another aspect of the invention provides a binding molecule that competes for human CD134 binding with an antibody comprising (1) a heavy chain variable region comprising the amino acid sequence of SEQ ID NO: 12 and (2) a light chain variable region comprising the amino acid sequence of SEQ ID NO: 13, as shown by cross-competition between an un-labelled said binding molecule and a fluorescent-labelled said antibody on PHA-stimulated human CD134-expressing T-lymphocytes, as measured by flow cytometry (further described in Example 2(e)). Preferably, the binding of said antibody, at or above its saturation concentration, is reduced by at least about 50%, or about 60%, or about 70%, or about 80%, or about 90% or more, and is preferably abolished, when assayed by cross-competition against said binding molecule.

Another aspect of the invention provides a binding molecule that competes for human CD134 binding with an antibody comprising (1) a heavy chain variable region comprising the amino acid sequence of SEQ ID NO: 4 and (2) a light chain variable region comprising the amino acid sequence of SEQ ID NO: 5, as shown by cross-competition between an un-labelled said binding molecule and a fluorescent-labelled said antibody on PHA-stimulated human CD134 expressing T-lymphocytes, as measured by flow cytometry (further described in Example 2(e)). Preferably, the binding of said antibody, at or above its saturation concentration, is reduced by at least about 50%, or about 60%, or about 70%, or about 80%, or about 90% or more, and is preferably abolished, when assayed by cross-competition against said binding molecule.

Another aspect of the invention provides a binding molecule that binds to human CD134, wherein the effect on binding of OX40L to CD134 on human CD134 expressing T-cells is reduced by not more than about 70%, or about 60%, or about 50%, or about 40%, or about 30%, or about 20%, or about 10% or less, and wherein said binding molecule further does not impede the immunostimulatory and/or proliferative responses of human OX40L on human CD134 expressing T-effector cells.

Another aspect of the invention provides a binding molecule that binds to human CD134, wherein the binding molecule does not prevent human CD134 (OX40) receptor binding to OX40 ligand (OX40L) and wherein said binding molecule further does not impede the immunostimulatory and/or proliferative responses of human OX40L on human CD134 expressing T-effector cells.

Another aspect of the invention provides a binding molecule that binds to human CD134, wherein the effect on binding of OX40L to CD134 on human CD134 expressing T-cells is reduced by not more than about 70%, or about 60%, or about 50%, or about 40%, or about 30%, or about 20%, or about 10% or less, and wherein said binding molecule enhances the immunostimulatory and/or proliferative responses of human OX40L on human CD134 expressing T-effector cells.

Another aspect of the invention provides a binding molecule that binds to human CD134, wherein the binding molecule does not prevent human CD134 (OX40) receptor binding to OX40 ligand (OX40L) and wherein said binding molecule enhances the immunostimulatory and/or proliferative responses of human OX40L on human CD134 expressing T-effector cells.

Another aspect of the invention provides a binding molecule that binds to human CD134, wherein the effect on binding of OX40L to CD134 on human CD134 expressing human T-cells is reduced by not more than about 70%, or about 60%, or about 50%, or about 40%, or about 30%, or about 20%, or about 10% or less, and wherein said binding molecule further does not impede suppressor function responses of human OX40L on human CD134 expressing T-regulatory cells.

Another aspect of the invention provides a binding molecule that binds to human CD134, wherein the binding molecule does not prevent human CD134 (OX40) receptor binding to OX40 ligand (OX40L) and wherein said binding molecule further does not impede suppressor function responses of human OX40L on human CD134 expressing T-regulatory cells.

Another aspect of the invention provides a binding molecule that binds to human CD134, wherein the effect on binding of OX40L to CD134 on human CD134 expressing human T-cells is reduced by not more than about 70%, or about 60%, or about 50%, or about 40%, or about 30%, or about 20%, or about 10% or less, and wherein said binding molecule enhances the suppressor function responses of human OX40L on human CD134 expressing T-regulatory cells.

Another aspect of the invention provides a binding molecule that binds to human CD134, wherein the binding molecule does not prevent human CD134 (OX40) receptor binding to OX40 ligand (OX40L) and wherein said binding molecule enhances the suppressor function responses of human OX40L on human CD134 expressing T-regulatory cells Another aspect of the invention provides a binding molecule that binds to human CD134, wherein the effect on binding of OX40L to CD134 on human CD134 expressing T-cells is reduced by not more than about 70%, or about 60%, or about 50%, or about 40%, or about 30%, or about 20%, or about 10% or less, and wherein said binding molecule further does not impede the proliferative responses of human OX40L on human CD134 expressing T-regulatory cells.

Another aspect of the invention provides a binding molecule that binds to human CD134, wherein the binding molecule does not inhibit or prevent human CD134 (OX40) receptor binding to OX40 ligand (OX40L) and wherein said binding molecule further does not impede the proliferative responses of human OX40L on human CD134 expressing T regulatory cells.

Another aspect of the invention provides a binding molecule that binds to human CD134, wherein the effect on binding of OX40L to CD134 on human CD134 expressing T-cells is reduced by not more than about 70%, or about 60%, or about 50%, or about 40%, or about 30%, or about 20%, or about 10% or less, and wherein said binding molecule inhibits the proliferative responses of human OX40L on human CD134 expressing T-regulatory cells.

Another aspect of the invention provides a binding molecule that binds to human CD134, wherein the binding molecule does not inhibit or prevent human CD134 (OX40) receptor binding to OX40 ligand (OX40L) and wherein said binding molecule inhibits the proliferative responses of human OX40L on human CD134 expressing T regulatory cells.

A suitable method for measuring the simultaneous binding of OX40L and anti-CD134 antibody is described as follows. FITC fluorescent signal (geomean or mean fluorescent intensity (MFI)) of human OX40L binding on PHA-stimulated human CD134 expressing PBMCs in absence of anti-human CD134 antibody is set at 100%. PE fluorescent signal (MFI) of anti-human CD134 antibody binding on PHA-stimulated human CD134 expressing PBMCs in absence of human OX40L is set at 100%. Reduction of this FITC fluorescent signal and PE fluorescent signal when both human OX40L and anti-human CD134 antibody are added simultaneously to PHA-stimulated human CD134 expressing PBMCs preferably does not exceed about 70%, or about 60%, or about 50%, or about 40%, or about 30%, or about 20%, or about 10% or less.

A suitable method for measuring the lack of impediment on OX40L-mediated proliferative responses of Teffs is as follows. Tritiated thymidine or BrdU incorporation in human CD134 expressing Teffs after human OX40L treatment is set at 100%. Change (i.e. decrement or increment) of this tritiated thymidine or BrdU incorporation when both human OX40L and anti-human CD134 antibody are added simultaneously to activated (e.g., PHA-stimulated or anti-CD3/anti-CD28 beads-stimulated) human CD134 expressing Teffs preferably does not exceed about 30%, or about 20%, or about 10% or less.

A suitable method for measuring enhancement on OX40L-mediated proliferative responses of Teffs, is as follows. Tritiated thymidine or BrdU incorporation in human CD134 expressing Teffs after human OX40L treatment is set at 100%. Enhancement of this tritiated thymidine or BrdU incorporation when both human OX40L and anti-human CD134 antibody are added simultaneously to activated (e.g., PHA-stimulated or anti-CD3/anti-CD28 beads-stimulated) human CD134 expressing Teffs is preferably greater than about 30%, or about 40%, or about 50%, or about 60%, or about 70%, or higher.

A suitable method for measuring the lack of impediment on OX40L-mediated suppression function of Tregs is as follows. Tritiated thymidine or BrdU incorporation in human CD134 expressing Teffs, which are co-cultured with human CD134 expressing Teffs (e.g., Teff/Treg ratio=1:1), after human OX40L treatment is set at 100%. Change (i.e. decrement or increment) of this tritiated thymidine or BrdU incorporation when both human OX40L and anti-human CD134 antibody are added simultaneously to activated (e.g., PHA-stimulated or anti-CD3/anti-CD28 beads-stimulated) human CD134 expressing Teffs, which are co-cultured with human CD134 expressing Teffs (e.g., Teff/Treg ratio=1:1), preferably does not exceed about 30%, or about 20%, or about 10% or less.

A suitable method for measuring enhancement on OX40L-mediated suppression function of Tregs is as follows. Tritiated thymidine or BrdU incorporation in human CD134 expressing Teffs, which are co-cultured with human CD134 expressing Teffs (e.g., Teff/Treg ratio=1:1), after human OX40L treatment is set at 100%. Enhancement of this tritiated thymidine or BrdU incorporation when both human OX40L and anti-human CD134 antibody are added simultaneously to activated (e.g., PHA-stimulated or anti-CD3/anti-CD28 beads-stimulated) human CD134 expressing Teffs, which are co-cultured with human CD134 expressing Teffs (e.g., Teff/Treg ratio=1:1), is preferably greater than about 30%, or about 40%, or about 50%, or about 60%, or about 70%, or higher.

A suitable method for measuring the lack of impediment on OX40L-mediated proliferative responses of Tregs is as follows. Tritiated thymidine or BrdU incorporation in human CD134 expressing Tregs after human OX40L treatment is set at 100%. Change (i.e. decrement or increment) of this tritiated thymidine or BrdU incorporation when both human OX40L and anti-human CD134 antibody are added simultaneously to activated (e.g., PHA-stimulated or anti-CD3/anti-CD28 beads-stimulated) human CD134 expressing Tregs preferably does not exceed about 30%, or about 20%, or about 10% or less.

A suitable method for measuring the inhibition of OX40L-mediated proliferative responses of Tregs, is as follows. Tritiated thymidine or BrdU incorporation in human CD134 expressing Tregs after human OX40L treatment is set at 100%. Reduction of this tritiated thymidine or BrdU incorporation when both human OX40L and anti-human CD134 antibody are added simultaneously to activated (e.g., PHA-stimulated or anti-CD3/anti-CD28 beads-stimulated) human CD134 expressing Tregs is preferably greater than about 30%, or about 40%, or about 50%, or about 60%, or about 70%, or higher.

Another aspect of the invention provides a method of treating cancer in a mammal, comprising administering to the mammal a therapeutically effective amount of a binding molecule as described herein.

In a further preferred embodiment of the invention the binding molecule is antibody clone 12H3 and/or clone 20E5, or an antigen-binding fragment of either antibody. In a further embodiment, the mammal is a human.

In another preferred embodiment of the invention is provided a method of preventing cancer in a mammal, comprising administering to the mammal a therapeutically effective amount of a binding molecule as described herein.

The term "preventing cancer" or "prevention of cancer" refers to delaying, inhibiting, or preventing the onset of a cancer in a mammal in which the onset of oncogenesis or tumorigenesis is not evidenced but a predisposition for cancer is identified whether determined by genetic screening, for example, or otherwise. The term also encompasses treating a mammal having premalignant conditions to stop the progression of, or cause regression of, the premalignant conditions towards malignancy. Examples of premalignant conditions include hyperplasia, dysplasia, and metaplasia. In some embodiments, the binding molecule is an anti-CD134 antibody or a fragment thereof as described herein. In a further embodiment of the invention is provided a binding molecule selected from antibody clone 12H3 and/or clone 20E5, or an antigen-binding fragment of either antibody. In a further embodiment, the mammal is a human.

A variety of cancers, including malignant or benign and/or primary or secondary, may be treated or prevented with a method according to the invention. Examples of such cancers are known to those skilled in the art and listed in standard textbooks such as the Merck Manual of Diagnosis and Therapy (published by Merck).

In another embodiment of the invention, the binding molecules may be administered alone as monotherapy, or administered in combination with one or more additional therapeutic agents or therapies. Thus, in another embodiment of the invention is provided a method of treating or preventing cancer by a combination therapy, which method comprises administering a binding molecule as disclosed herein, in combination with one or more additional therapies or therapeutic agents. The term "additional therapy" refers to a therapy which does not employ a binding molecule provided by the disclosure as a therapeutic agent. The term "additional therapeutic agent" refers to any therapeutic agent other than a binding molecule provided by the disclosure. In some embodiments, the binding molecule is anti-human CD134 antibody clone 12H3 and/or clone 20E5, or an antigen-binding fragment of either antibody. In one particular aspect, the present disclosure provides a combination therapy for treating cancer in a mammal, which comprises administering to the mammal a therapeutically effective amount of a binding molecule provided by the disclosure in combination with one or more additional therapeutic agents. In a further embodiment, the mammal is a human.

A wide variety of cancer therapeutic agents may be used in combination with a binding molecule. One of ordinary skill in the art will recognize the presence and development of other cancer therapies which can be used in combination with the methods and binding molecules of the present disclosure, and will not be restricted to those forms of therapy set forth herein. Examples of categories of additional therapeutic agents that may be used in the combination therapy for treating cancer include (1) chemotherapeutic agents, (2) immunotherapeutic agents, and (3) hormone therapeutic agents.

The term "chemotherapeutic agent" refers to a chemical or biological substance that can cause death of cancer cells, or interfere with division, repair, growth, and/or function of cancer cells. Examples of chemotherapeutic agents include those that are disclosed in WO 2006/088639, WO 2006/129163, and US 20060153808, the disclosures of which are incorporated herein by reference.

The term "immunotherapeutic agents" refers to a chemical or biological substance that can enhance an immune response of a mammal. Examples of immunotherapeutic agents include: bacillus Calmette-Guerin (BCG); cytokines such as interferons; vaccines such as MyVax personalized immunotherapy, Onyvax-P, Oncophage, GRNVACI, Favld, Provenge, GVAX, Lovaxin C, BiovaxiD, GMXX, and NeuVax; and antibodies such as alemtuzumab (CAMPATH), bevacizumab (AVASTIN), cetuximab (ERBITUX), gemtuzunab ozogamicin (MYLOTARG), ibritumomab tiuxetan (ZEVALIN), panitumumab (VECTIBIX), rituximab (RITUXAN, MABTHERA), trastuzumab (HERCEPTIN), tositumomab (BEXXAR), tremelimumab, CAT-3888, and agonist antibodies to CD40 receptor that are disclosed in WO2003/040170.

The term "hormone therapeutic agent" refers to a chemical or biological substance that inhibits or eliminates the production of a hormone, or inhibits or counteracts the effect of a hormone on the growth and/or survival of cancerous cells. Examples of such agents suitable for the methods herein include those that are disclosed in US20070117809. Examples of particular hormone therapeutic agents include tamoxifen (NOLVADEX), toremifene (Fareston), fulvestrant (FASLODEX), anastrozole (ARIMIDEX), exemestane (AROMASIN), letrozole (FEMARA), megestrol acetate (MEGACE), goserelin (ZOLADEX), and leuprolide (LUPRON). The binding molecules of this disclosure may also be used in combination with non-drug hormone therapies such as (1) surgical methods that remove all or part of the organs or glands which participate in the production of the hormone, such as the ovaries, the testicles, the adrenal gland, and the pituitary gland, and (2) radiation treatment, in which the organs or glands of the patient are subjected to radiation in an amount sufficient to inhibit or eliminate the production of the targeted hormone.

in another embodiment of the invention is provided a method of treating or preventing cancer by a combination therapy, which method comprises administering a binding molecule as disclosed herein, and surgery to remove a tumour. The binding molecule may be administered to the mammal before, during, or after said surgery.

The combination therapy for treating cancer also encompasses combination of a binding molecule provided by the disclosure with radiation therapy, such as ionizing (electromagnetic) radiotherapy (e.g., X-rays or gamma rays) and particle beam radiation therapy (e.g., high linear energy radiation). The source of radiation can be external or internal to the mammal. The binding molecule may be administered to the mammal before, during, or after the radiation therapy.

The binding molecules and compositions provided by the present disclosure can be administered via any suitable enteral route or parenteral route of administration. The term "enteral route" of administration refers to the administration via any part of the gastrointestinal tract. Examples of enteral routes include oral, mucosal, buccal, and rectal route, or intragastric route. "Parenteral route" of administration refers to a route of administration other than enteral route. The suitable route and method of administration may vary depending on a number of factors such as the specific antibody being used, the rate of absorption desired, specific formulation or dosage form used, type or severity of the disorder being treated, the specific site of action, and conditions of the patient, and can be readily selected by a person skilled in the art.

The term "therapeutically effective amount" of a binding molecule refers to an amount that is effective for an intended therapeutic purpose. For example, in the context of enhancing an immune response, a "therapeutically effective amount" is any amount that is effective in stimulating, evoking, increasing, improving, or augmenting any response of a mammal's immune system. In the context of treating cancer, a "therapeutically effective amount" is any amount that is sufficient to cause any desirable or beneficial effect in the mammal being treated, such as inhibition of further growth or spread of cancer cells, death of cancer cells, inhibition of reoccurrence of cancer, reduction of pain associated with the cancer, or improved survival of the mammal. In a method of preventing cancer, a "therapeutically effective amount" is any amount that is effective in delaying, inhibiting, or preventing the onset of a cancer in the mammal to which the binding molecule is administered.

The therapeutically effective amount of a binding molecule usually ranges from about 0.001 to about 500 mg/kg, and more usually about 0.05 to about 100 mg/kg, of the body weight of the mammal. For example, the amount can be about 0.3 mg/kg, 1 mg/kg, 3 mg/kg, 5 mg/kg, 10 mg/kg, 50 mg/kg, or 100 mg/kg of body weight of the mammal. In some embodiments, the therapeutically effective amount of an anti-human CD134 antibody is in the range of about 0.1-30 mg/kg of body weight of the mammal. The precise dosage level to be administered can be readily determined by a person skilled in the art and will depend on a number of factors, such as the type, and severity of the disorder to be treated, the particular binding molecule employed, the route of administration, the time of administration, the duration of the treatment, the particular additional therapy employed, the age, sex, weight, condition, general health and prior medical history of the patient being treated, and like factors well known in the art.

A binding molecule or composition is usually administered on multiple occasions. Intervals between single doses can be, for example, weekly, monthly, every three months or yearly. An exemplary treatment regimen entails administration once per week, once every two weeks, once every three weeks, once every four weeks, once a month, once every 3 months or once every three to 6 months. Typical dosage regimens for an anti-human CD134 antibody include 1 mg/kg body weight or 3 mg/kg body weight via intravenous administration, using one of the following dosing schedules: (i) every four weeks for six dosages, then every three months; (ii) every three weeks; (iii) 3 mg/kg body weight once followed by 1 mg/kg body weight every three weeks.

This invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLES

Example 1

Generation of Mouse Anti-Human CD134 (=OX40) Monoclonal Antibodies (a). Generation of Sf9 Insect Cells Expressing Surface CD134 cDNA encoding for human CD134 protein (GenBank ref CAB96543.1; see SEQ ID NO.1) was optimized for Sf9 insect cell (*Spodotera frugiperda*) expression and synthesized by GENEART, Regensburg, Germany (see SEQ ID NO.2). This cDNA was subcloned in baculovirus transfer plasmid pVL1393 (BD transfection kit cat no. 560129; BD Biosciences). Subsequently, Sf9 insect cells (ATCC) were co-transfected with transfer plasmid pVL1393 containing cDNA encoding human CD134 together with BaculoGold Baculovirus DNA (BD transfection kit), and then incubated at 27° C. for 4-5 days. After this co-transfection step, supernatant was collected and stored at 4° C., and used to infect more Sf9 insect cells for virus amplification. For this purpose, Sf9 insect cells were transfected with amplified recombinant baculovirus, and then incubated at 27° C. for 3-5 days. These Sf9 insect cells were harvested, washed with sterile PBS, and aliquoted at $5 \times 10^6$ cells/250 µl in PBS and stored at −80° C. to obtain cell lysates. Prior to storage, human CD134 surface expression on transfected Sf9 insect cells were confirmed using 1:10 phycoerythrin (PE)-conjugated mouse anti-human CD134 (clone ACT35; BD Biosciences) and flow cytometry.

(b). Immunization and Generation of Mouse Anti-Human CD134 Monoclonal Antibodies BALB/c mice (females, 6 weeks of age; Charles River Laboratories) were subcutaneously injected with ≈400 µL human CD134-transfected Sf9 insect cell lysates (250 µL cell lysate aliquot+250 µL Complete Freund's adjuvant; Sigma) on Day 0. Similar subcutaneous injections using human CD134-transfected Sf9 insect cell lysates and Incomplete Freund's adjuvant (Sigma) were given on Day 21 and Day 42. Intraperitoneal booster injections with human CD134-transfected Sf9 insect cell lysates (250 µL/mouse) without adjuvant were given on Day 61 and on Day 62. On day 65, splenocytes from immunized mice were fused with SP2/0 myeloma cells (ATCC) using standard hybridoma technology initially described by Köhler and Milstein (Nature 1975; 256: p 495-497). Hybridomas, which produced antibodies (mouse IgG class) against human CD134 (screened with conventional ELISA and flow cytometric techniques using a recombinant human CD134:human Fcγ fusion protein (R&D Systems) and human CD134 expressing PHA (Roche)-stimulated CD4 T cell blasts (see Example 2 below) as targets, respectively) were expanded, cryopreserved, and cloned by limiting dilution. Anti-human CD134 specific monoclonal antibodies were purified using protein G columns (GE Healthcare), and resulted in mouse anti-human CD134 monoclonal antibodies clone 12H3 (mouse IgG1κ isotype; determined with IsoStrip™ Mouse Monoclonal antibody Isotype Kit from Roche) and clone 20E5 (mouse IgG1κ isotype; idem).

Example 2

Flow Cytometric Characterization of Mouse Anti-Human CD134 Monoclonal Antibodies Clones 12H3 and 20E5

(a). CD134 Expression on PHA-Stimulated Human T Lymphocytes

Human peripheral blood mononuclear cells (PBMC) from healthy donors (informed consent) were isolated by density centrifugation on Lymphoprep (1.077 g/mL; Nycomed). Subsequently, $1-2 \times 10^6$ PBMC/mL in RPMI-1640 culture medium (Gibco) containing 10% fetal calf serum (Bodinco) and 50 µg/mL gentamycin (Gibco) was supplemented with 0, 0.1, 1.0 or 10.0 µg/mL phytohaemagglutinin-M (PHA-M; Roche) at 37° C./5% $CO_2$ for 1-3 days. After culture, PBMC were harvested and put at $1-2 \times 10^6$ cells/mL in ice-chilled phosphate-buffered saline containing 0.1% bovine serum albumin (Sigma)/0.05% $NaN_3$ (PBS/BSA/$NaN_3$) supplemented with 10% human pooled serum (HPS; blocking Fcγ receptors; BioWhittaker). Cells were incubated with 10 µg/mL commercially available mouse anti-human CD134 antibody clone ACT35 (mouse IgG1 isotype; BD Biosciences, Alphen aan de Rijn, The Netherlands) for 30 minutes at 4° C. After extensive washing in PBS/BSA/$NaN_3$, cells were subsequently incubated with 1:200 diluted PE-conjugated goat anti-mouse IgG antibodies (Jackson ImmunoResearch) for 30 minutes at 4° C. After extensive washing in PBS/BSA/NaN$_3$, cells were incubated with 1:20 diluted Fluorescein isothiocyanate (FITC)-conjugated mouse anti-human CD3 antibody (BD Biosciences) to detect T lymphocytes for 30 minutes at 4° C. After extensive washing in PBS/BSA/NaN$_3$, cells were fixed in 2% formaldehyde in PBS/BSA/NaN$_3$ for 30 minutes at 4° C. Binding of antibodies was measured using flow cytometry (FACSCalibur; BD Biosciences).

As shown in FIG. 1 (n=1 from each donor), peripheral blood-derived non-stimulated/resting human T lymphocytes did not express any CD134, however, PHA dose-dependently stimulated human CD3$^{positive}$ T lymphocytes to express surface CD134. When exposed to 10 μg/mL PHA, CD134 expression levels on activated human CD3$^{positive}$ T lymphocytes seemed to reach a plateau between 'day 1' and 'day 2', however, the percentage of human CD134$^{positive}$/CD3$^{positive}$ T lymphocytes time-dependently increased during experimentation.

(b). CD134 Expression on PHA-Stimulated Human CD4 T Lymphocyte Subpopulation

PHA-stimulated (at 0 and 10 μg/mL for 1 day; see above) human CD134 expressing T lymphocytes were generated. Cells were harvested and put at 1-2×10$^6$ cells/mL in ice-chilled PBS/BSA/NaN$_3$ supplemented with 10% HPS (blocking Fcγ receptors; BioWhittaker). Cells were incubated with 1:10 diluted FITC-conjugated mouse anti-human CD4 antibody (BD Biosciences) or 1:10 diluted FITC-conjugated mouse anti-human CD8 antibody (BD Biosciences) in combination with 1:10 diluted commercially available PE-conjugated mouse anti-human CD134 clone ACT35 (BD Biosciences) for 30 minutes at 4° C. After extensive washing in PBS/BSA/NaN$_3$, cells were fixed in 2% formaldehyde in PBS/BSA/NaN$_3$ for 30 minutes at 4° C. Binding of antibodies was measured using flow cytometry (FACSCalibur; BD Biosciences).

Figure 2:
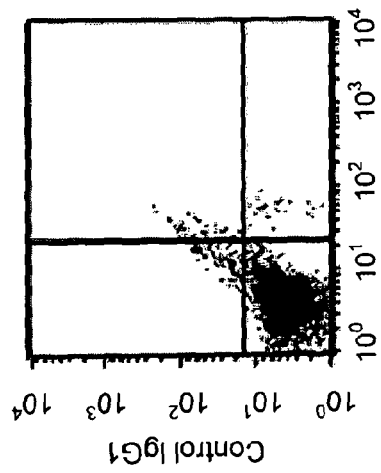
FIG. 2. Human CD134 expression on resting and on PHA-M-activated human CD4 T lymphocytes.
Figure 2:
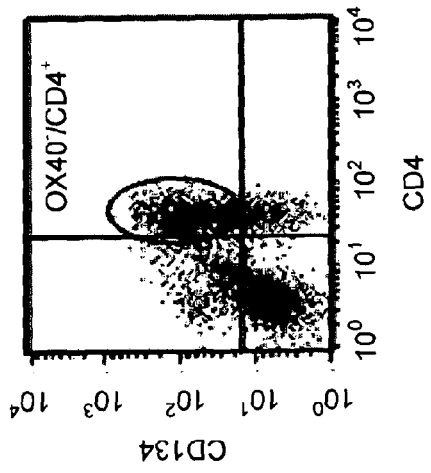
Figure 2:
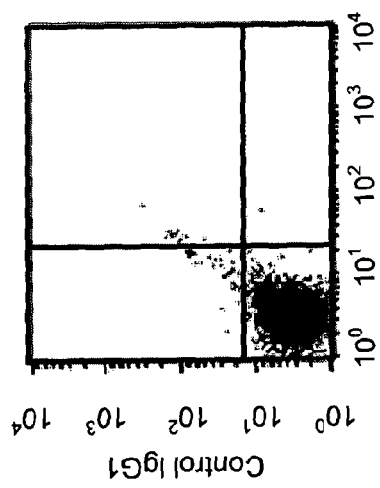
Figure 2:
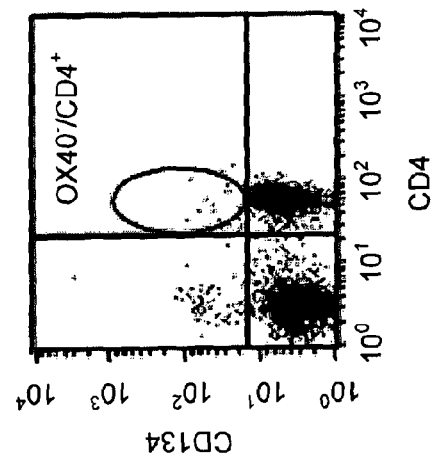

As shown in FIG. 2, CD134 expression was observed on PHA-stimulated human CD4$^{positive}$ T lymphocytes and not on resting human CD4$^{positive}$ T lymphocytes. Low CD134 expression was found on PHA-activated human CD8$^{positive}$ T lymphocytes and not on resting human CD8$^{positive}$ T lymphocytes (data not shown).

(c). Binding of Mouse Anti-Human CD134 Monoclonal Antibodies Clones 12H3 and 20E5 on PHA-Stimulated Human CD134 Expressing T Lymphocytes PHA-stimulated (at 10 μg/mL for 2 days; see above) human CD134 expressing T lymphocytes were generated. Cells were harvested and put at 1-2×10$^6$ cells/mL in ice-chilled PBS/BSA/NaN$_3$ supplemented with 10% HPS (blocking Fcγ receptors; BioWhittaker). Cells were incubated with 0, 0.007, 0.02, 0.07, 0.2, 0.6, 1.9, 5.6, 16.7, 50.0 μg/mL commercially available mouse anti-human CD134 antibody clone ACT35 (mouse IgG1 isotype; BD Biosciences) and in-house generated mouse anti-human CD134 antibody clone 12H3 or clone 20E5 for 30 minutes at 4° C. After extensive washing in PBS/BSA/NaN$_3$, cells were subsequently incubated with 1:200 diluted PE-conjugated goat anti-mouse IgG antibodies (Jackson ImmunoResearch) for 30 minutes at 4° C. After extensive washing in PBS/BSA/NaN$_3$, cells were incubated with 1:20 diluted FITC-conjugated mouse anti-human CD3 antibody (BD Biosciences) to detect T lymphocytes for 30 minutes at 4° C. After extensive washing in PBS/BSA/NaN$_3$, cells were fixed in 2% formaldehyde in PBS/BSA/NaN$_3$ for 30 minutes at 4° C. Binding of antibodies was measured using flow cytometry (FACSCalibur; BD Biosciences).

Figure 3:
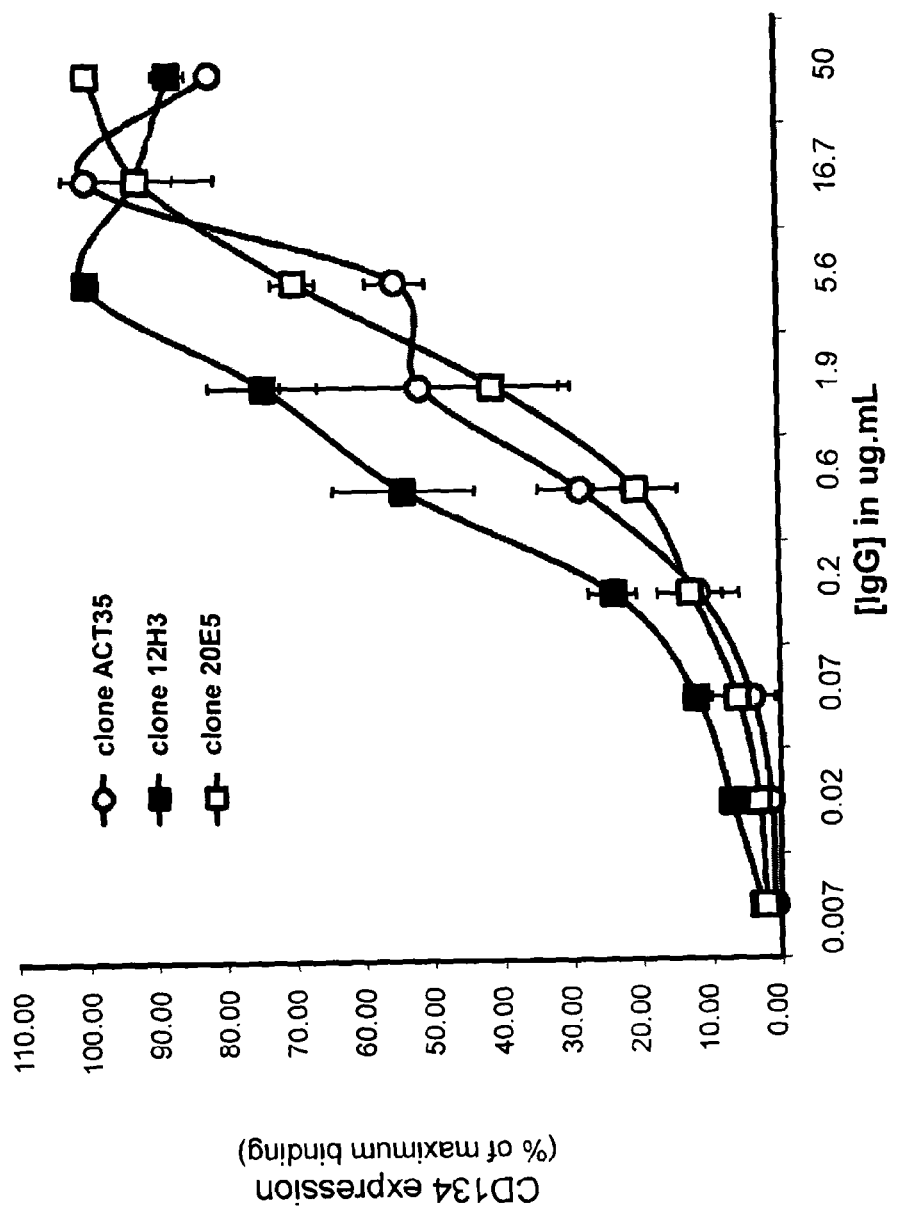
FIG. 3. Binding characteristics of mouse anti-human CD134 antibodies clone ACT35, clone 12H3, and clone 20E5 on PHA-M-stimulated human CD134 expressing T lymphocytes.

As shown in FIG. 3 (mean±SD; results observed in two donors), mouse anti-human CD134 antibody clone ACT35, clone 12H3, and clone 20H5 saturated human CD134 surface molecules on PHA-stimulated CD3$^{positive}$ T lymphocytes at approximately 5.0-10.0 μg/mL. Using these two donors, half maximal binding was observed at ≈0.5 μg/mL for mouse anti-human CD134 antibody clone 12H3, and at ≈2.5 μg/mL for mouse anti-human CD134 antibody clone ACT35 and clone 20E5.

(d). Binding of Mouse Anti-Human CD134 Monoclonal Antibodies Clones 12H3 and 20E5 on PHA-Stimulated Human CD134 Expressing CD4 Positive and CD8 Positive T Lymphocytes PHA-stimulated (at 20 μg/mL for 1 day; see above) human CD134 expressing T lymphocytes were generated. Cells were harvested and put at 1-2×10$^6$ cells/mL in ice-chilled PBS/BSA/NaN$_3$ supplemented with 10% HPS (blocking Fcγ receptors; BioWhittaker). Cells were incubated with 20.0 μg/mL mouse IgG1κ isotype control (BD Biosciences), or with 20.0 μg/mL mouse anti-human CD134 monoclonal antibody clone 12H3 or clone 20E5 for 30 minutes at 4° C. After extensive washing in PBS/BSA/NaN$_3$, cells were subsequently incubated with 1:100 diluted PE-conjugated goat anti-mouse IgG antibodies (Jackson ImmunoResearch) for 30 minutes at 4° C. After extensive washing in PBS/BSA/NaN$_3$, cells were incubated for 30 minutes at 4° C. with 1:20 diluted FITC-conjugated mouse anti-human CD4 antibody (BD Biosciences) or with 1:20 diluted FITC-conjugated mouse anti-human CD8 antibody (BD Biosciences) to detect T lymphocyte subpopulations. After extensive washing in PBS/BSA/NaN$_3$, cells were fixed in 2% formaldehyde in PBS/BSA/NaN$_3$ for 30 minutes at 4° C. Binding of antibodies was measured using flow cytometry (FACSCalibur; BD Biosciences).

Figure 4:
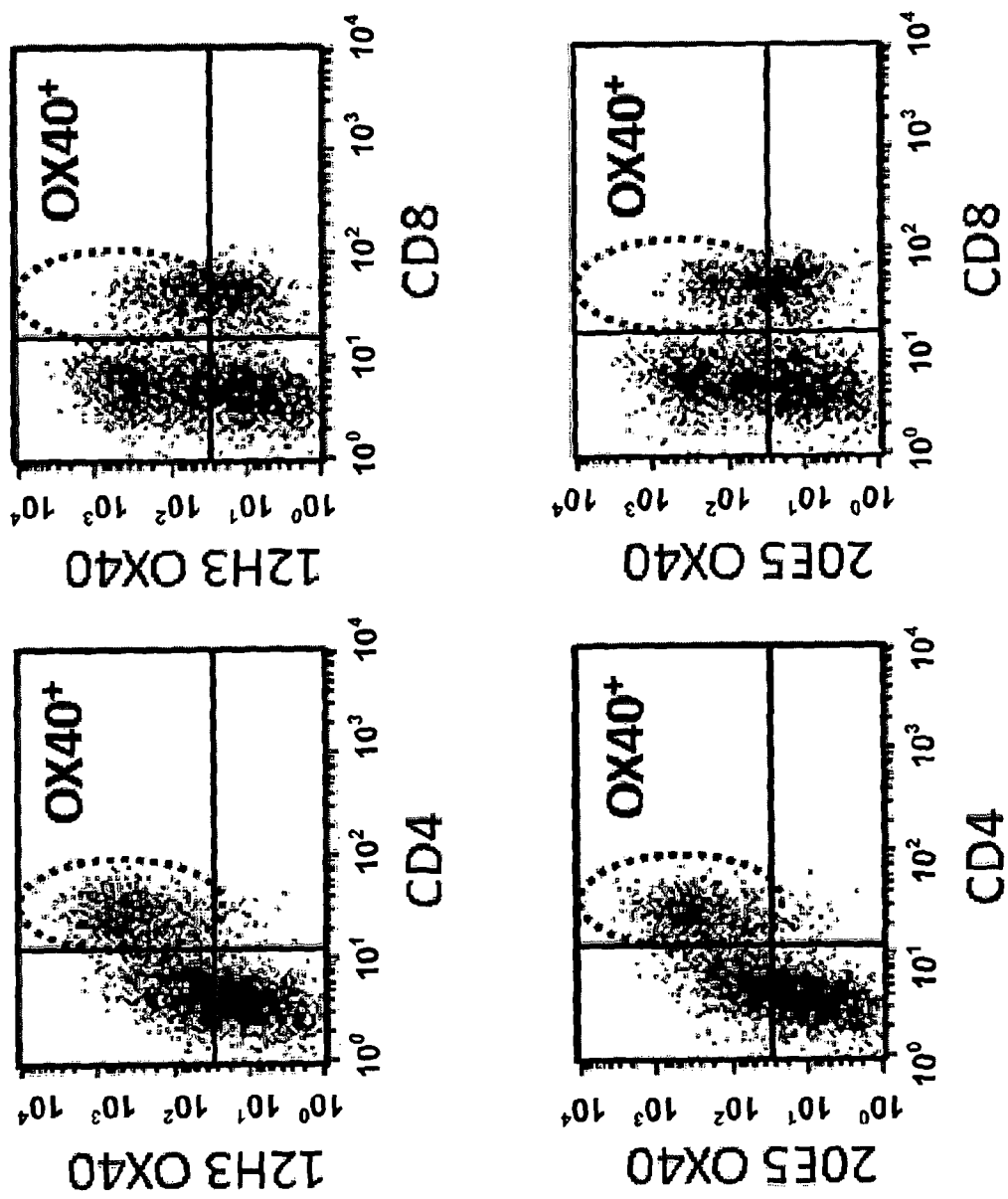
FIG. 4. Binding of mouse anti-human CD134 antibodies clone 12H3 and clone 20E5 on PHA-M-stimulated human CD134 expressing CD4 T lymphocytes and CD8 T lymphocytes.

As shown in FIG. 4, mouse anti-human CD134 monoclonal antibody clone 12H3 and clone 20E5 demonstrated positive staining on the activated human CD4$^{positive}$ T lymphocyte subpopulation, and low positive staining on the activated human CD8$^{positive}$ T lymphocyte subpopulation.

(e). Cross-Competition of Non-Labeled Mouse Anti-Human CD134 Antibodies Clones 12H3 and 20E5 with PE-Conjugated Commercial Mouse Anti-CD134 Antibodies on PHA-Stimulated Human CD134 Expressing T Lymphocytes PHA (at 10 μg/mL or at 20 μg/mL for 4 days or for 1 day, respectively; see above) stimulated human CD134 expressing T lymphocytes were generated. Cells were harvested and put at 1-2×10$^6$ cells/mL in ice-chilled PBS/BSA/NaN$_3$ supplemented with 10% HPS (blocking Fcγ receptors; BioWhittaker). Cells were incubated with 20 μg/mL non-labeled mouse anti-human CD134 monoclonal antibody clone 12H3 or with 10 μg/mL non-labeled clone 20E5 for 30 minutes at 4° C. Cells were subsequently incubated with 1:20 diluted PE-conjugated commercially available mouse anti-human CD134 antibody clone ACT35 (BD Biosciences) or clone L106 (BD Biosciences; see also Godfrey patent) for 30 minutes at 4° C. After extensive washing in PBS/BSA/NaN$_3$, cells were fixed in 2% formaldehyde in PBS/BSA/NaN$_3$ for 30 minutes at 4° C. Binding of PE-conjugated commercial available anti-CD134 antibodies was measured using flow cytometry (FACSCalibur; BD Biosciences).

Figure 5:
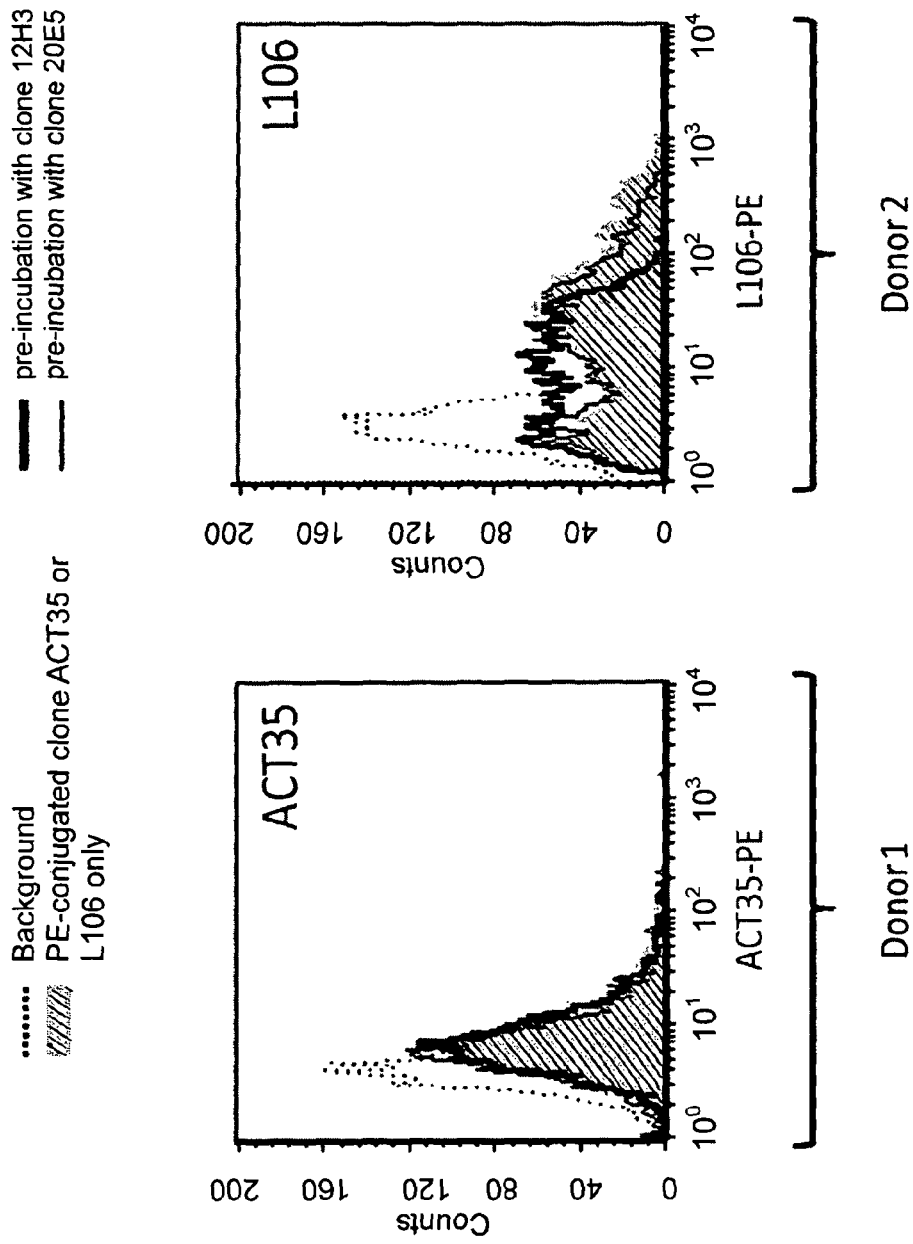
FIG. 5. Cross-competition of non-labeled mouse anti-human CD134 antibodies clone 12H3 or clone 20E5 with PE-conjugated commercial mouse anti-CD134 antibodies clone ACT35 or clone L106 on PHA-M-stimulated human CD134 expressing T lymphocytes.

As shown in FIG. 5, pre-incubation with non-labeled mouse anti-human CD134 antibody clone 12H3 partially blocked the binding of commercial PE-conjugated mouse anti-human CD134 antibody clone L106 against human CD134 on PHA-stimulated T lymphocytes. Pre-incubation with non-labelled mouse anti-human CD134 antibody clone 20E5 slightly blocked the binding of commercial PE-conjugated mouse anti-human CD134 antibody clone L106 against human CD134 on PHA-stimulated T lymphocytes. Pre-incubation with non-labelled mouse anti-human CD134 antibody clone 12H3 and clone 20E5 showed no effect on the binding of commercial PE-conjugated mouse anti-human CD134 antibody clone ACT35 against human CD134 on PHA-stimulated T lymphocytes.

These results demonstrated that mouse anti-human CD134 antibody clone 12H3 specifically recognized human CD134 (partial blocking of clone L106 binding) on PHA-stimulated T lymphocytes, and bound (ii) to a non-identical epitope on human CD134, which was recognized by commercial mouse anti-human CD134 antibody clone L106. These results also demonstrated that mouse anti-human CD134 antibody clone 20E5 (i) specifically recognized human CD134 (slight blocking of clone L106 binding) on PHA-stimulated T lymphocytes, and (ii) bound to a non-identical epitope, which was recognized by commercial mouse anti-human CD134 antibody clone L106. Moreover, these results demonstrated that mouse anti-human CD134 antibody clone 12H3 and clone 20E5 seemed to recognize human CD134 epitopes on PHA-stimulated T lymphocytes, which were different to the epitope recognized by commercial mouse anti-human CD134 antibody clone ACT35. In addition, these results demonstrated that mouse anti-human CD134 antibody clone 12H3 and clone 20E5 seemed to recognize dissimilar human CD134 epitopes (evidenced by partial blocking vs slight blocking of L106 binding, respectively) on PHA-stimulated T lymphocytes.

(f). Simultaneous Binding of Recombinant Human OX40 Ligand and Mouse Anti-Human CD134 Antibodies Clones 12H3 and 20E5 on PHA-Stimulated Human CD134 Expressing T Lymphocytes PHA-stimulated (at 10 µg/mL for 1 day; see above) human CD134 expressing T lymphocytes were generated. Cells were harvested and put at $1-2\times10^6$ cells/mL in ice-chilled PBS/BSA/NaN$_3$ supplemented with 10% HPS (blocking Fcγ receptors; BioWhittaker). Cells were incubated with 10.0 µg/mL polyhistidine-tagged recombinant human OX40 ligand (OX40L; R&D Systems) in combination with 50.0 µg/mL anti-polyhistidine antibody (mouse IgG$_1$, clone AD1.1.10; R&D Systems) for 30 minutes at 4° C. After extensive washing in PBS/BSA/NaN$_3$, cells were subsequently incubated with 1:100 diluted FITC-conjugated goat anti-mouse IgG antibodies (Jackson ImmunoResearch) for 30 minutes at 4° C. After extensive washing in PBS/BSA/NaN$_3$, cells were incubated with 10.0 µg/mL biotinylated (using N-hydroxysuccinimido-biotin from Pierce) mouse anti-human CD134 monoclonal antibody clone 12H3 or clone 20E5 for 30 minutes at 4° C. After extensive washing in PBS/BSA/NaN$_3$, cells were incubated with 1:100 diluted PE-conjugated streptavidin (Jackson ImmunoResearch) for 30 minutes at 4° C. After extensive washing in PBS/BSA/NaN$_3$, cells were fixed in 2% formaldehyde in PBS/BSA/NaN$_3$ for 30 minutes at 4° C. Binding of human OX40L and anti-human CD134 antibodies was measured using flow cytometry (FACSCalibur; BD Biosciences).

Figure 6:
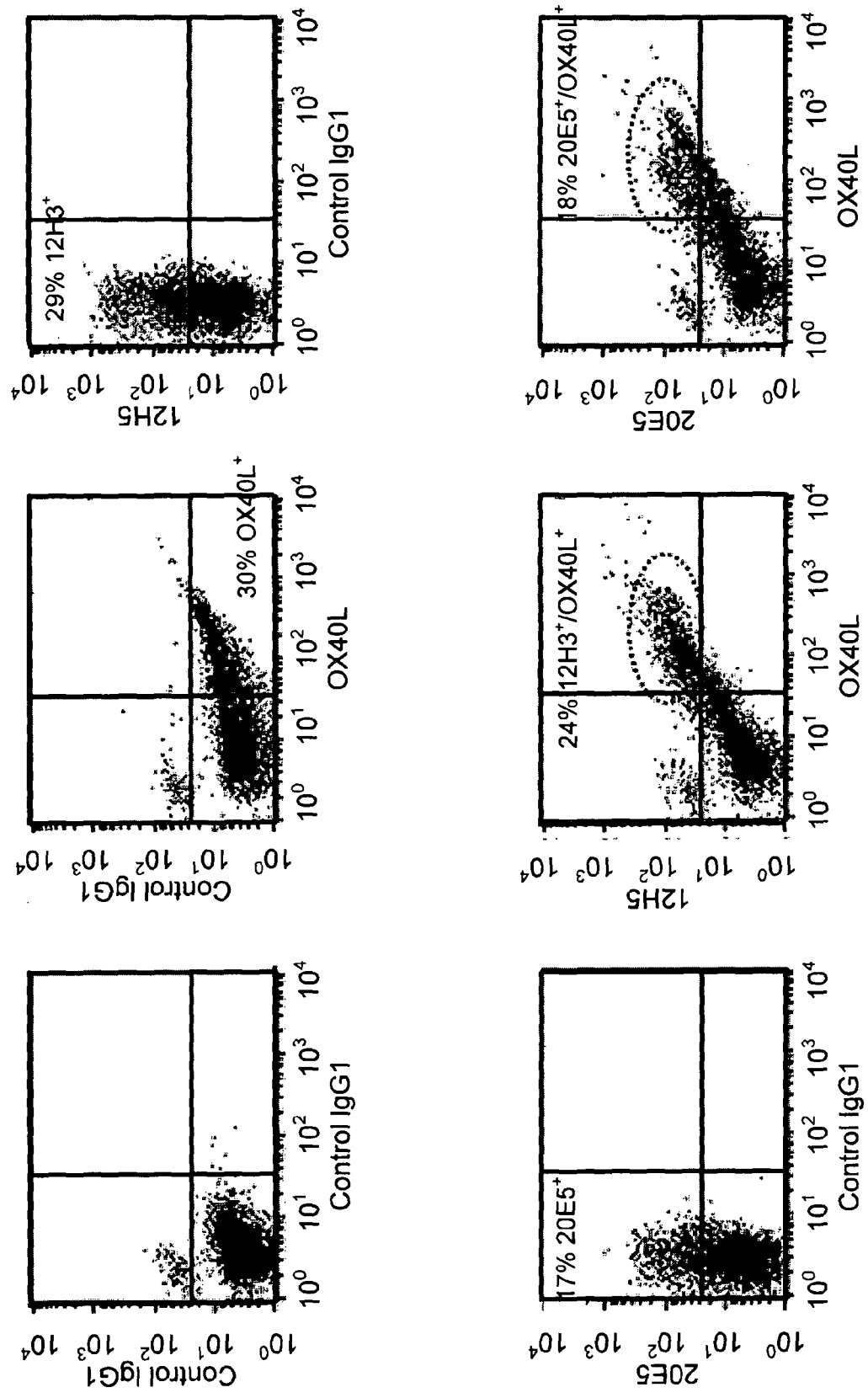
FIG. 6. Simultaneous binding of mouse anti-human CD134 antibodies clone 12H3 or clone 20E5 with human OX40L on PHA-M-stimulated human CD134 expressing T lymphocytes.

As shown in FIG. 6, both mouse anti-human CD134 monoclonal antibody clone 12H3 and mouse anti-human CD134 monoclonal antibody clone 20E5 bound simultaneously with human OX40L on PHA-stimulated human CD134 expressing T lymphocytes. This indicated that mouse anti-human CD134 monoclonal antibody clone 12H3 and clone 20E5 do not interact with epitopes within the OX40L binding region on human CD134 receptors. This finding is in contrast with commercially available mouse anti-human CD134 monoclonal antibody clone L106 (Stanford University/Godfrey patent EP 0 726 952 B1), which recognized an epitope within the human OX40L binding region of human CD134 receptors (Taylor and Schwarz. J Immunol Methods 2001; 255: 67-72; Kirin & La Jolla Institute/Croft patent WO 2007/062235 A2).

(g). CD134 Expression on Human Effector and Regulatory T Lymphocytes after Stimulation with Anti-Human CD3/Anti-Human CD28 Antibody Stimulator Beads Human CD4 T lymphocytes were purified from PBMCs by positive selection using microbeads-conjugated mouse anti-human CD4 antibodies (Miltenyi Biotec) and VarioMACS™ Magnet/LS columns (Miltenyi Biotec). Subsequently, these CD4 T lymphocytes were stained with FITC-conjugated mouse anti-human CD4 antibodies (Dako) and PE-conjugated mouse anti-human CD25 antibodies (BD Biosciences). $CD4^{positive}/CD25^{negative}$ conventional effector T lymphocytes (Teffs) and $CD4^{positive}/CD25^{high}$ regulatory T lymphocytes (Tregs) were sorted using an Altra flow cytometric cell sorter (Beckman-Coulter). This resulted in enrichments of >95% Teffs and of >95% Tregs. Teffs and Tregs were put on $2.5\times10^5$ cells/mL in RPMI-1640/glutamax culture medium (Gibco) supplemented with 0.02 mM pyruvate (Gibco), 100 U/mL penicillin (Gibco), 100 µg/mL streptomycin (Gibco), and 10% heat inactivated HPS (HPS$_i$; from LMI). Then, cells were seeded at $2.5\times10^4$ cells/200 µL/well in 96-well round-bottom plates (Greiner), and stimulated with mouse anti-human CD3/mouse anti-human CD28 antibody stimulator beads (CD3/CD28 beads; Invitrogen) at 1 bead/2 cells in the presence of 25 U/mL recombinant human interleukin-2 (Proleukin® from Novartis Pharmaceuticals UK Ltd) at 37° C./5% CO$_2$ for 2-8 days. After culture, cells were harvested and put at $1-2\times10^6$ cells/mL in ice-chilled PBS/0.2% BSA, and were simultaneously stained with 1:50 diluted FITC-conjugated mouse anti-human CD4 antibody (Dako), 1:10 diluted PE-conjugated mouse anti-human CD25 antibody (BD Biosciences), 1:50 diluted ECD™-conjugated mouse anti-human CD3 antibody (Beckman-Coulter), 1:10 diluted PE-Cy™5-conjugated mouse anti-human CD134 antibody (clone ATC35; BD Biosciences), and 1:10 diluted PE-Cy™7-conjugated mouse anti-human CD127 antibody (eBiosciences). Binding of antibodies was measured using flow cytometry (FACSCalibur; BD Biosciences).

Figure 7:
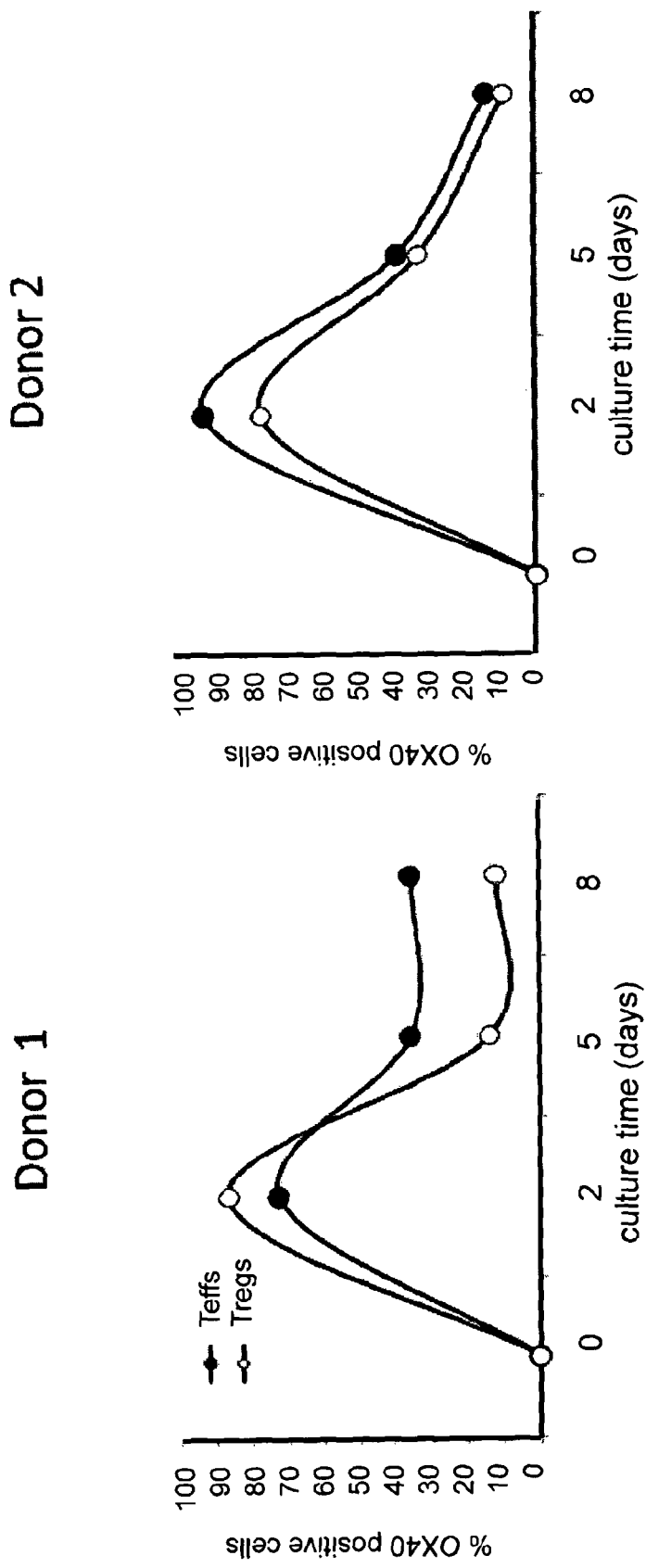
FIG. 7. Time course effect of exposure to anti-human CD3/anti-human CD28 antibody stimulator beads on surface human CD134 expression of human effector T lymphocytes (Teffs) and of regulatory T lymphocytes (Tregs).

As shown in FIG. 7 (n=1 from each donor), peripheral blood-purified non-stimulated/resting (day 0) human Teffs and human Tregs did not express any CD134, however, CD3/CD28 beads-stimulated human Teffs and human Tregs expressed surface CD134. CD134 expression on activated human Teffs and human Tregs peaked after 2 days in culture, and attenuated after 5 and 8 days in culture.

Example 3

Biological Characterization of Mouse Anti-Human CD134 Monoclonal Antibodies Clones 12H3 and 20E5

(a). Proliferation of PHA-Stimulated Human CD134 Expressing T Lymphocytes after Treatment with Mouse Anti-Human CD134 Antibodies Clones 12H3 and 20E5

PHA-stimulated (at 0 and 10 µg/mL for 1 day; see above) human CD134 expressing T lymphocytes were generated. Cells were harvested and suspended at $2\times10^6$ cells/mL in RPMI culture medium (Gibco) containing 10% fetal calf serum (Bodinco) and 50 µg/mL gentamycin (Gibco). Cells were seeded at $0.1\times10^6$ cells/100 µL/well (i.e., $1\times10^6$ cells/mL) in 96-wells flat-bottom plates (Corning), and were exposed to 0, 0.025, 0.25, 2.5, or 25.0 µg/mL mouse anti-human CD134 monoclonal antibody clone 12H3 or mouse anti-human CD134 monoclonal antibody clone 20E5, or/and in combination with 0, 0.01, 0.1, or 1.0 µg/mL polyhistidine-tagged recombinant human OX40L (in the presence of 1:5 molar ratio mouse anti-polyhistidine antibody; R&D Systems) at 37° C./5% $CO_2$ for 6 days. After 6 days, cell proliferation was measured using the colorimetric (BrdU incorporation) Cell Proliferation ELISA™ (Roche) and an ELISA reader (BioRad) at A450 nm.

Figure 8:
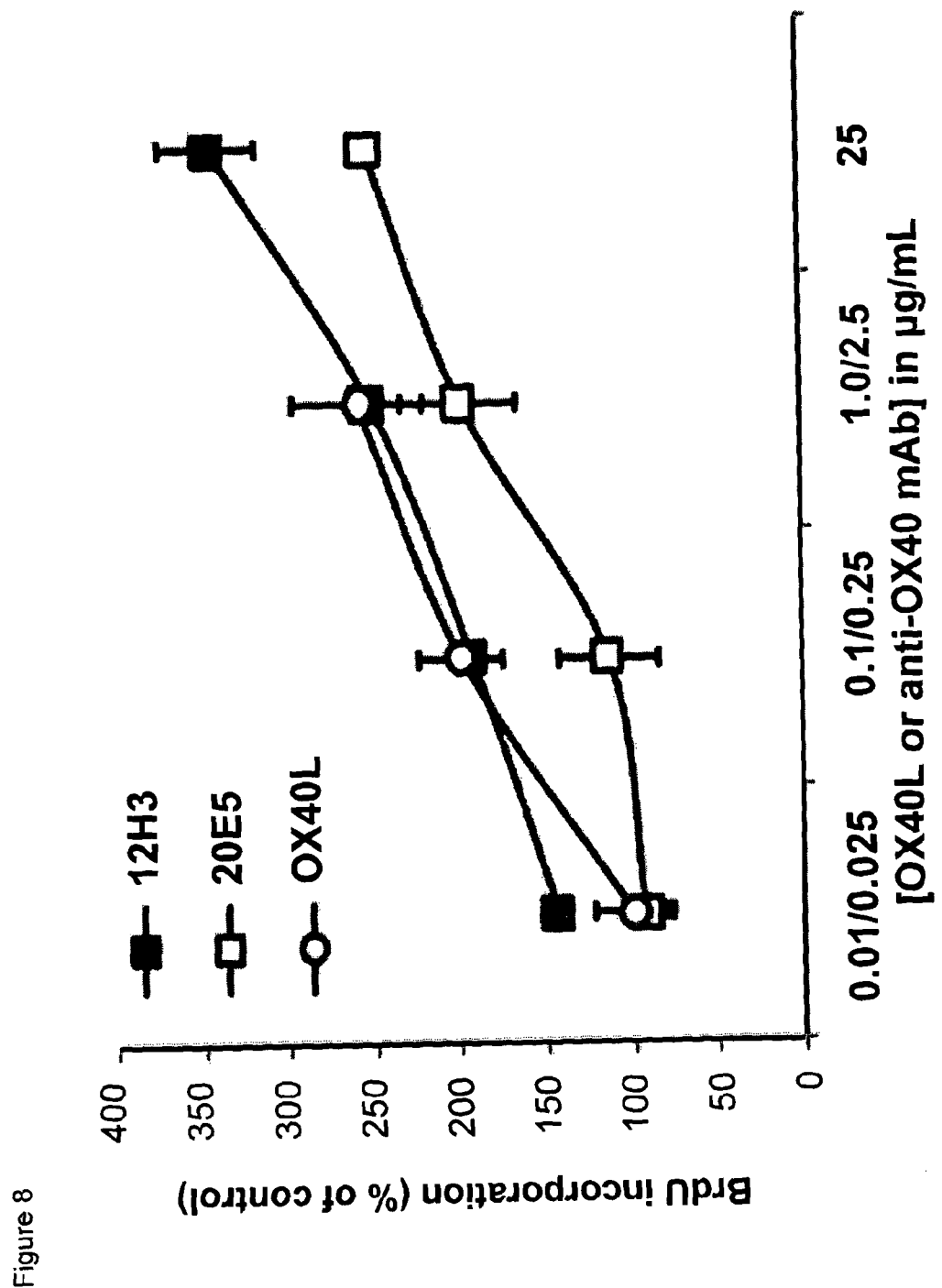
FIG. 8. Dose effect of exposure to mouse anti-human CD134 antibodies clone 12H3 or clone 20E5, or to human OX40L on proliferation of PHA-M-stimulated human CD134 expressing T lymphocytes.

As shown in FIG. 8 (mean±SD, n=4 using one donor), mouse anti-human CD134 monoclonal antibody clone 12H3 and mouse anti-human CD134 monoclonal antibody clone 20E5 dose-dependently induced proliferation in PHA-stimulated human CD134 expressing T lymphocytes. Mouse anti-human CD134 monoclonal antibody clone 12H3 induced proliferation at 0.25, 2.5, and 25 µg/mL. Mouse anti-human CD134 monoclonal antibody clone 12H3 induced proliferation at 2.5 and 25 µg/mL. In addition, human OX40L also dose-dependently induced proliferation in PHA-stimulated human CD134 expressing T lymphocytes. Human OX40L induced proliferation at 0.1 and 1.0 µg/mL. Resting (without PHA stimulation) human $CD134^{negative}$ T lymphocytes did not show any proliferative responses after treatment with mouse anti-human CD134 monoclonal antibody clone 12H3, mouse anti-human CD134 monoclonal antibody clone 20E5, or human OX40L (data not shown).

Figure 9:
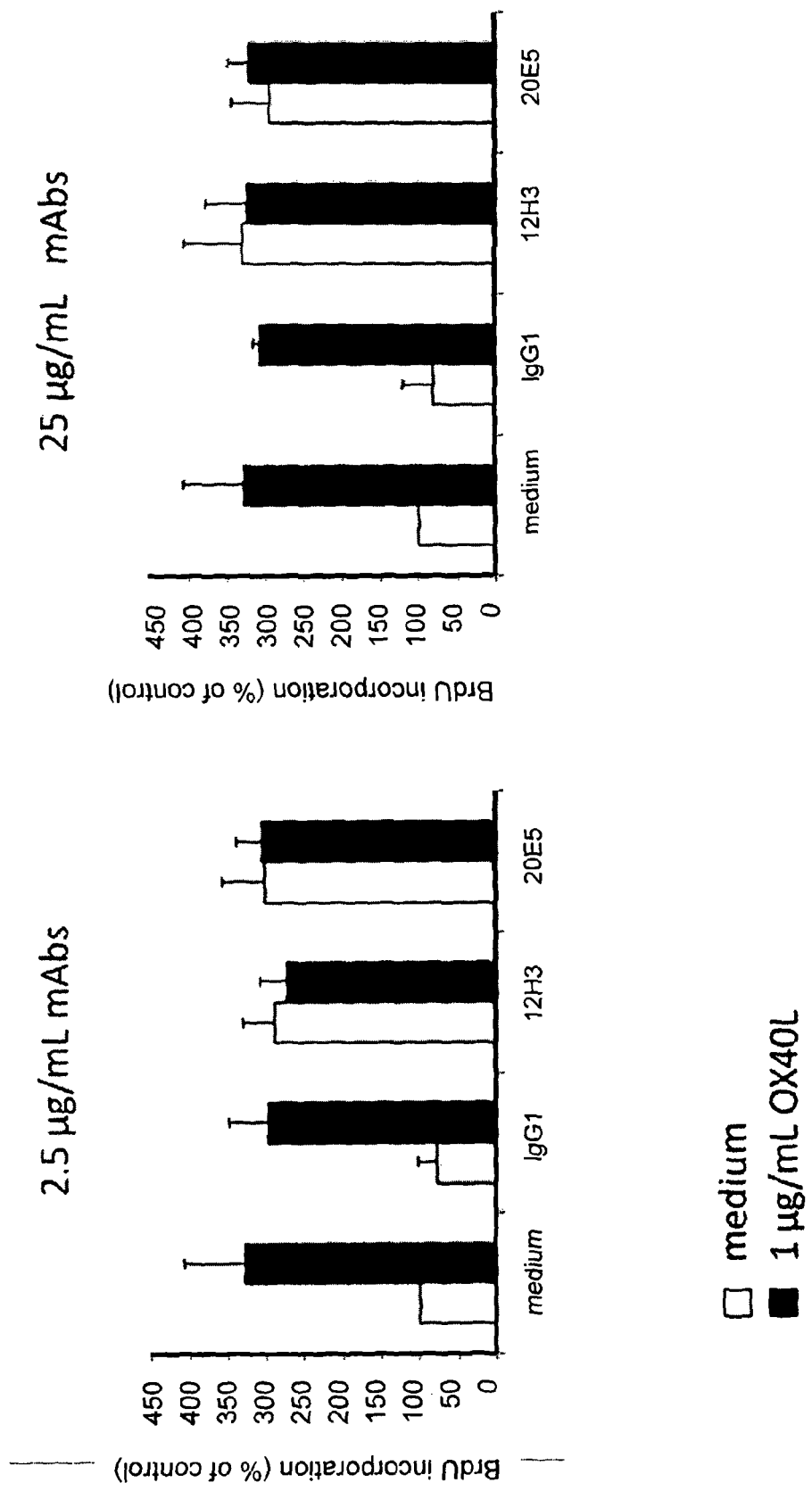
FIG. 9. Effect of combining mouse anti-human CD134 antibodies clone 12H3 with human OX40L, or mouse anti-human CD134 antibodies clone 20E5 with human OX40L on proliferation of PHA-M-stimulated human CD134 expressing T lymphocytes.

As shown in FIG. 9 (mean±SD, n=2 using one donor), mouse anti-human CD134 monoclonal antibody clone 12H3 (at 2.5 and 25 µg/mL), mouse anti-human CD134 monoclonal antibody clone 20E5 (at 2.5 and 25 µg/mL), and human OX40L (at 1.0 µg/mL) induced proliferation in PHA-stimulated human CD134 expressing T lymphocytes. Non-treated (medium only) or treatment with mouse IgG1κ isotype control (at 2.5 and 25 µg/mL; BD Biosciences) did not demonstrate any effect on PHA-stimulated human CD134 expressing T lymphocyte proliferation. The combination of mouse anti-human CD134 monoclonal antibody clone 12H3 at 2.5 and 25 µg/mL (or at lower concentrations; data not shown)) or mouse anti-human CD134 monoclonal antibody clone 20E5 at 2.5 and 25 µg/mL (or at lower concentrations; data not shown) with human OX40L at 1.0 µg/mL (or at lower concentrations; data not shown) did not demonstrate any reciprocal (i.e., synergistic or additive, or even inhibitory) effects on proliferation in PHA-stimulated human CD134 expressing T lymphocytes.

(b). Proliferation of Anti-Human CD3/Anti-CD28 Beads-Stimulated Human CD134 Expressing T Effector and T Regulator Lymphocytes after Treatment with Mouse Anti-Human CD134 Antibodies Clones 12H3 and 20E5

Human CD4 T lymphocytes were purified from PBMCs by negative selection using a cocktail of mouse antibodies (BD BioSciences) directed against human CD8 (clone RPA-T8), CD14 (clone M5E2), CD16 (clone 3G8), CD19 (clone 4G7), CD33 (clone P67.6), CD56 (clone B159), and CD235a (HIR2). After incubation with Dynabeads®-conjugated sheep anti-mouse IgG (Invitrogen), unbound CD4 T lymphocytes were collected from the Dynal Magnetic Particle Concentrator, MPC™-6 (Invitrogen). From these enriched CD4 T lymphocytes, $CD25^{high}$ Tregs and $CD25^{negative}$ Teffs were separated by MACS-sorting using 10 µL microbeads-conjugated mouse anti-human CD25 antibodies (Miltenyi Biotec)/$10^7$ cells and MiniMACS™ Magnet/MS columns (Miltenyi Biotec VarioMACS™ Magnet/LS columns (Miltenyi Biotec). This resulted in enrichments of >90% Teffs and of >90% Tregs. Teffs and Tregs were put on $0.25×10^6$ cells/mL in RPMI-1640/glutamax culture medium (Gibco) supplemented with 0.02 mM pyruvate (Gibco), 100 U/mL penicillin (Gibco), 100 µg/mL streptomycin (Gibco), and 10% HPS, Then, Teffs and Tregs were seeded at $2.5×10^4$ cells/200 µL/well (i.e., $0.125×10^6$ cells/mL) in 96-wells round-bottom plates (Greiner), and were stimulated with CD3/CD28 beads (Invitrogen) at 1 bead/5 cells with or without 5.0 µg/mL mouse anti-human CD134 monoclonal antibody clone 12H3, 5.0 µg/mL mouse anti-human CD134 monoclonal antibody clone 20E5, 1.0 µg/mL polyhistidine-tagged recombinant human OX40L (in the presence of 1:5 molar ratio mouse anti-polyhistidine antibody; R&D Systems), a combination of 5.0 µg/mL mouse anti-human CD134 monoclonal antibody clone 12H3 with 1.0 µg/mL polyhistidine-tagged recombinant human OX40L (in the presence of 1:5 molar ratio mouse anti-polyhistidine antibody), or a combination of 5.0 µg/mL mouse anti-human CD134 monoclonal antibody clone 20E5 with 1.0 µg/mL polyhistidine-tagged recombinant human OX40L (in the presence of 1:5 molar ratio mouse anti-polyhistidine antibody) at 37° C./5% $CO_2$ for 4 or 5 days. After 4 or 5 days, cell proliferation was measured using 0.5 µCi tritiated thymidine (Perkin & Elmer) incorporation and a β-counter (Canberra-Packard).

Figure 10:
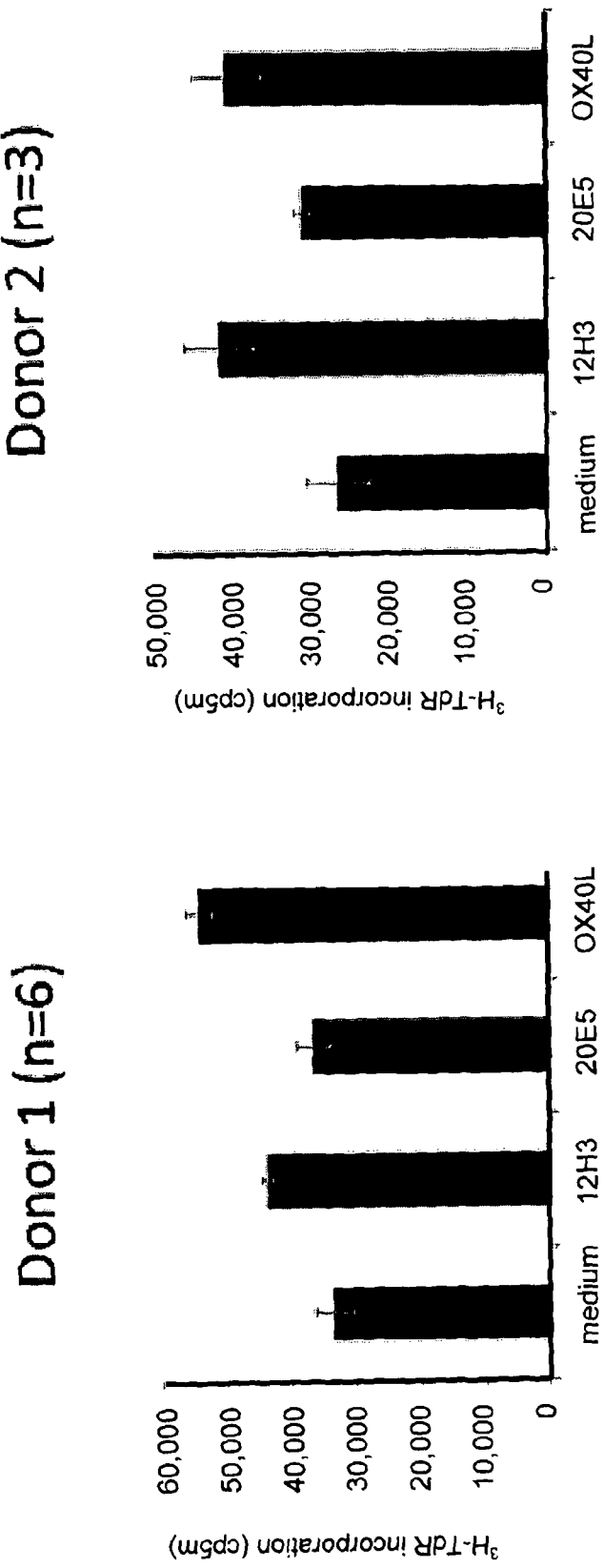
FIG. 10. Effect of exposure to mouse anti-human CD134 antibodies clone 12H3 or clone 20E5, or to human OX40L on proliferation of anti-human CD3/anti-human CD28 antibody stimulator beads-stimulated human CD134 expressing human effector T lymphocytes.
Figure 10:
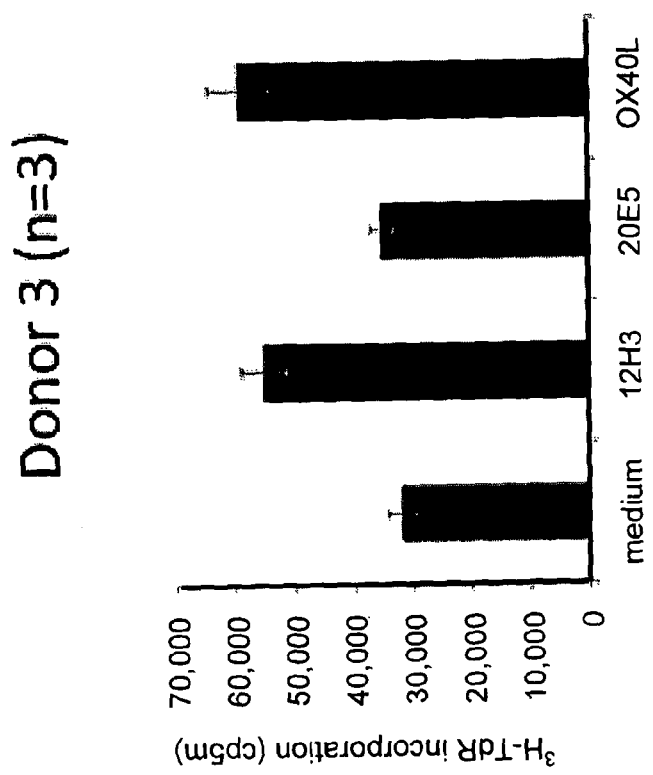

As shown in FIG. 10 (mean±SD), although CD3/CD28 stimulator beads alone induced considerable proliferation in human CD134 expressing Teffs (i.e. medium), mouse anti-human CD134 monoclonal antibody clone 12H3 or human OX40L induced additional proliferation in CD3/CD28 beads-stimulated human CD134 expressing Teffs. Mouse anti-human CD134 monoclonal antibody clone 20E5 did not induce additional proliferation in CD3/CD28 beads-stimulated human CD134 expressing Teffs.

Figure 11:
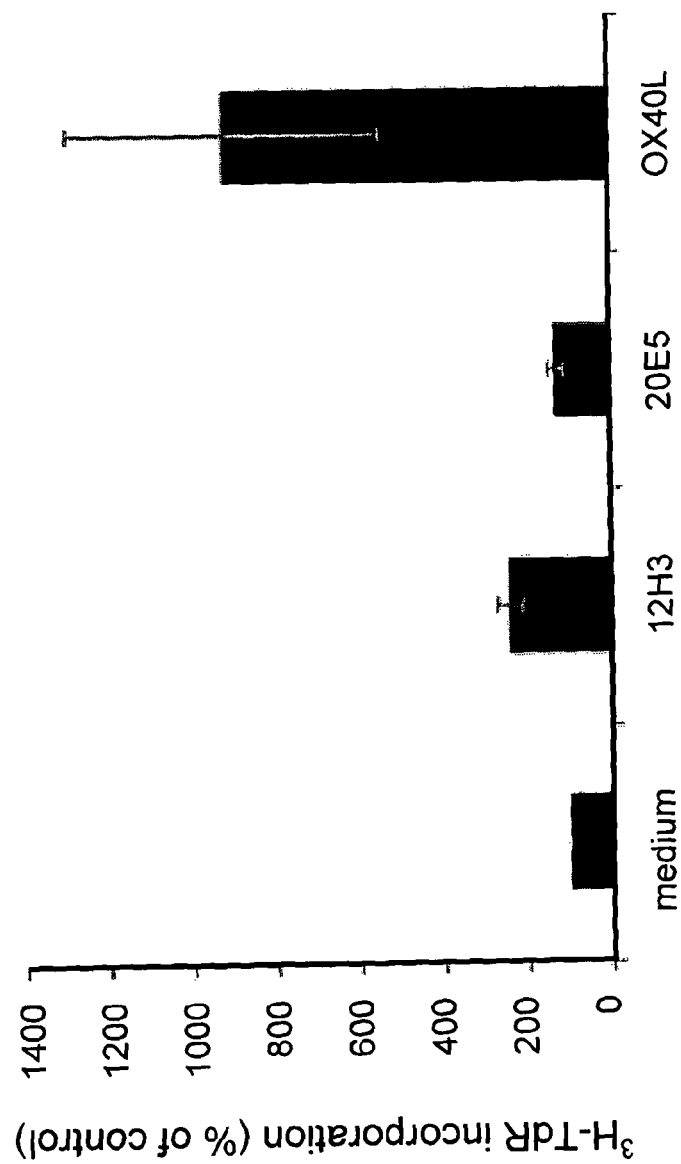
FIG. 11. Effect of exposure to mouse anti-human CD134 antibodies clone 12H3 or clone 20E5, or to human OX40L on proliferation of anti-human CD3/anti-human CD28 antibody stimulator beads-stimulated human CD134 expressing human regulatory T lymphocytes.

As shown in FIG. 11 (mean±SEM from 5 donors), mouse anti-human CD134 monoclonal antibody clone 12H3 and mouse anti-human CD134 monoclonal antibody clone 20E5 did not induce or induced low proliferation in CD3/CD28 beads-stimulated human CD134 expressing Tregs, whereas human OX40L induced very strong proliferation in CD3/CD28 beads-stimulated human CD134 expressing Tregs.

Figure 12:
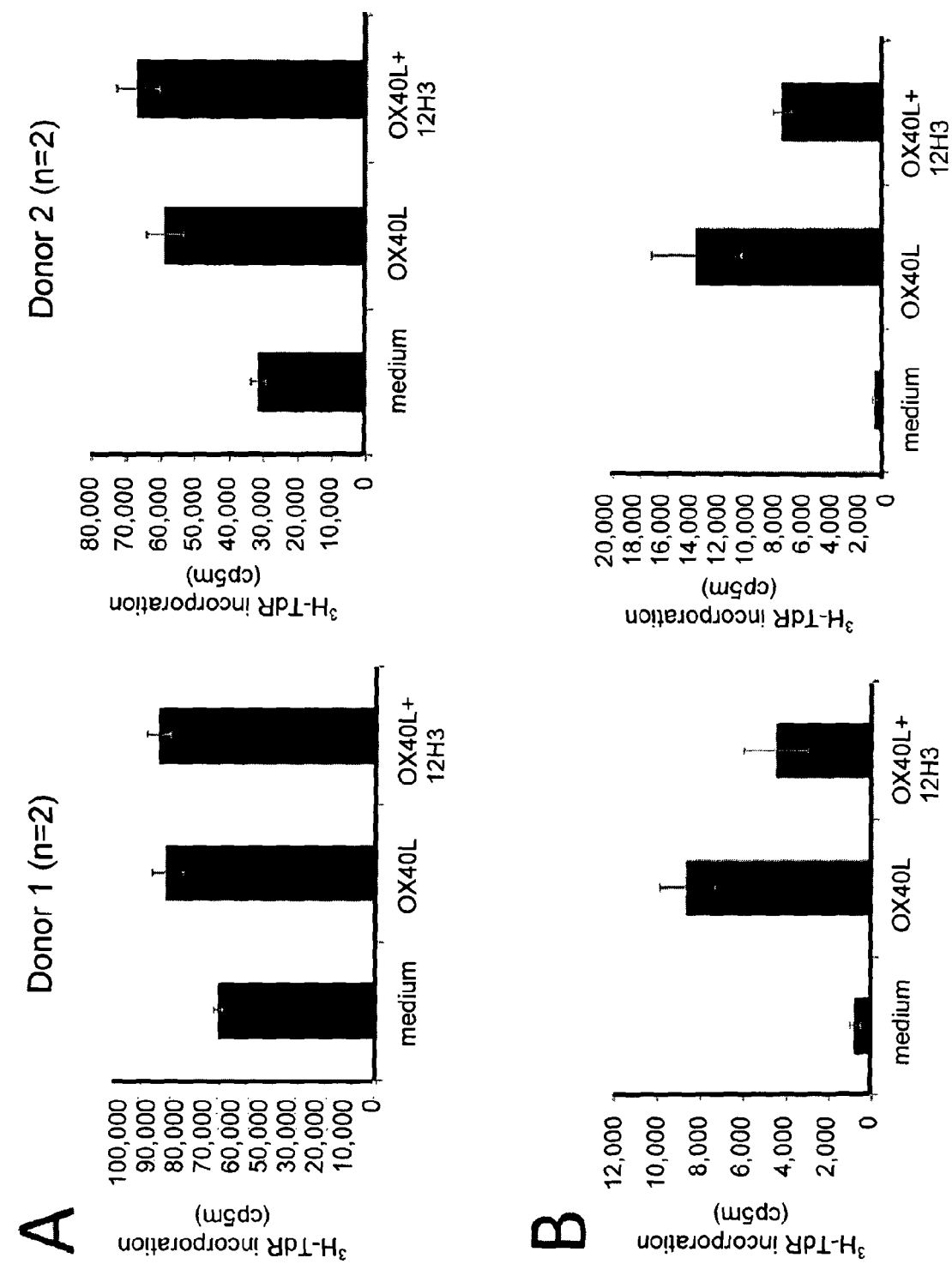
FIG. 12. Effect of mouse anti-human CD134 antibody clone 12H3 on human OX40L-mediated proliferation of anti-human CD3/anti-human CD28 antibody stimulator beads-stimulated human CD134 expressing human effector (A) and regulatory (B) T lymphocytes.

As shown in FIG. 12A (mean±SD), mouse anti-human CD134 monoclonal antibody clone 12H3 in combination with human OX40L did not demonstrate any reciprocal (i.e., inhibitory, synergistic or additive) effects in CD3/CD28 beads-stimulated human CD134 expressing Teffs. Furthermore, mouse anti-human CD134 monoclonal antibody clone 20E5 in combination with human OX40L did not demonstrate any reciprocal (i.e., inhibitory, synergistic or additive) effects in CD3/CD28 beads-stimulated human CD134 expressing Teffs (data not shown).

As shown in FIG. 12B (mean±SD), in contrast to the (lack of any) effect observed with human OX40L-mediated proliferative responses in CD3/CD28 beads-stimulated human CD134 expressing Teffs, mouse anti-human CD134 monoclonal antibody clone 12H3 strongly suppressed human OX40L-mediated proliferative responses in CD3/CD28 beads-stimulated human CD134 expressing Tregs.

(c). Suppression Function of Anti-Human CD3/Anti-CD28 Beads-Stimulated Human CD134 Expressing T Regulator Lymphocytes after Treatment with Mouse Anti-Human CD134 Antibodies Clones 12H3 and 20E5

Human CD4 T lymphocytes were purified from PBMCs, and Teffs and Tregs were enriched as described in Example 3(b) above. Teffs and Tregs were put on $0.25×10^6$ cells/mL in RPMI-1640/glutamax culture medium (Gibco) supplemented with 0.02 mM pyruvate (Gibco), 100 U/mL penicillin (Gibco), 100 µg/mL streptomycin (Gibco), and 10%

HPS$_i$. Then, Teffs were seeded at 2.5×10$^4$ cells/200 μL/well (i.e., 0.125×10$^6$ Teffs/mL) and co-cultured with 2.5×10$^4$ suppressive Tregs/200 μL/well (i.e., 0.125×10$^6$ Tregs/mL; Teffs/Tregs ratio=1:1) in 96-wells round-bottom plates (Greiner). These Teffs/Tregs co-cultures were stimulated with CD3/CD28 beads (Invitrogen) at 1 bead/10 cells with or without 5.0 μg/mL mouse anti-human CD134 monoclonal antibody clone 12H3, 5.0 μg/mL mouse anti-human CD134 monoclonal antibody clone 20E5, and 1.0 μg/mL polyhistidine-tagged recombinant human OX40L (in the presence of 1:5 molar ratio mouse anti-polyhistidine antibody; R&D Systems) at 37° C./5% CO$_2$ for 5 days. After 5 days, cell proliferation was measured using 0.5 μCi tritiated thymidine (Perkin & Elmer) incorporation and a β-counter (Canberra-Packard).

Figure 13:
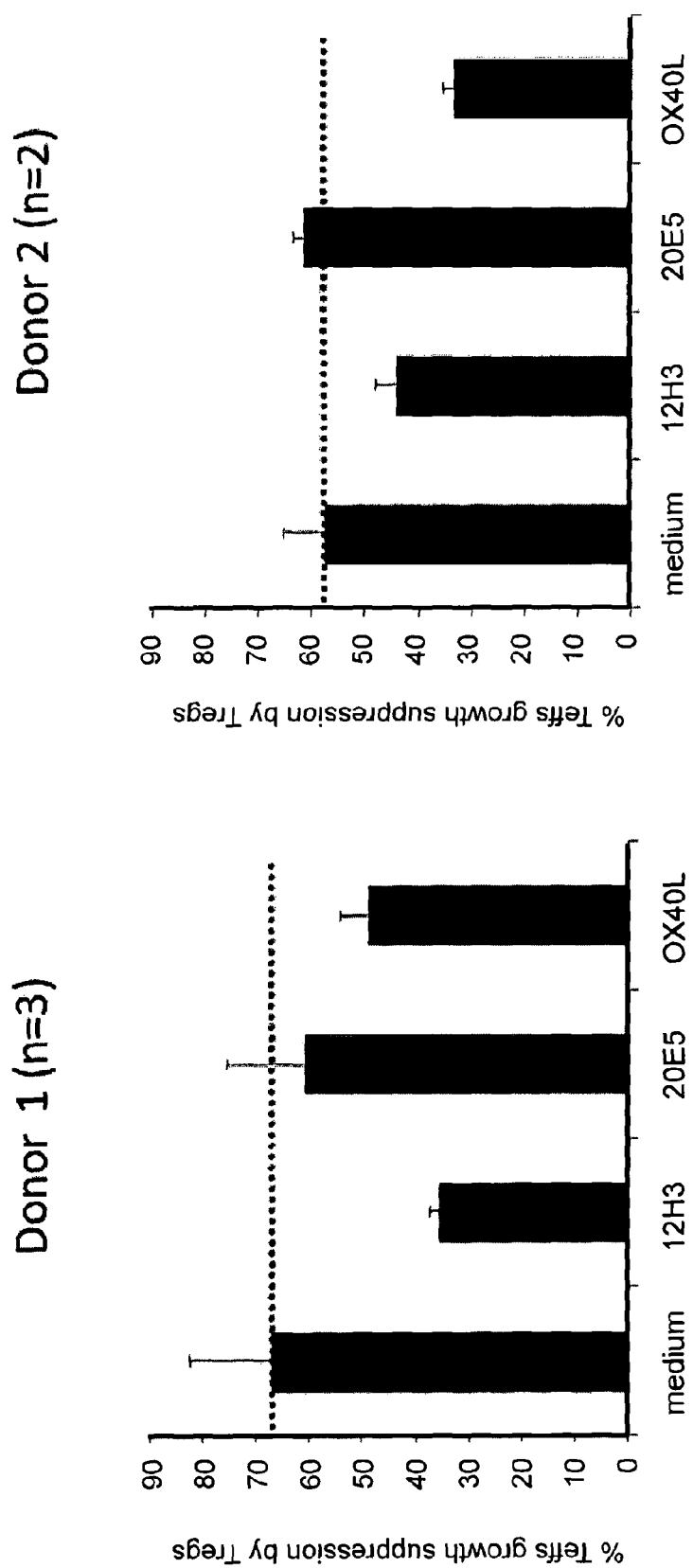
FIG. 13. Effect of exposure to mouse anti-human CD134 antibodies clone 12H3 or clone 20E5, or to human OX40L on human CD134 expressing human regulatory T lymphocyte-mediated suppression of human CD134 expressing human effector T lymphocyte proliferation.

As shown in FIG. 13 (mean±SD), human Tregs suppressed CD3/CD28 beads-induced human Teffs proliferative responses (i.e., medium). This suppressive function of human Tregs was dampened in the presence of mouse anti-human CD134 monoclonal antibody clone 12H3 or in the presence of human OX40L. Mouse anti-human CD134 monoclonal antibody clone 20E5 showed no effect on human Tregs suppressive function.

Example 4

Molecular Genetic Characterization of Mouse Anti-Human CD134 Monoclonal Antibodies Clones 20E5 and 12H3

(a). Isotyping and Edman Degradation

Mouse immunoglobulin class, isotype, and light chain type of Protein G-purified mouse anti-human CD134 monoclonal antibodies clones 20E5 and 12H3 were determined using the IsoStrip™ Mouse Monoclonal Antibody Isotype Kit (Roche), and showed that both mouse anti-human CD134 monoclonal antibodies clones 20E5 and 12H3 were mouse IgG1 with K light chains.

After standard LDS-PAGE electrophoresis, using the precast gel NuPage® Novex® system (Invitrogen) under reduced (DTT and 70° C. heating) conditions, mouse anti-human CD134 monoclonal antibody clone 20E5 was electro-blotted onto a polyvinylidene fluoride (PDVF/Immobilon-P) transfer membrane (Millipore), and stained with Coomassie brilliant blue (BioRad). Then, heavy and light chains bands (50 kDa and 25 kDa, respectively) were excised from the PVDF membrane, and used for Edman degradation analysis (performed by EuroSequence, Groningen, The Netherlands) to determine the N-terminal amino acid sequences. The results are shown in SEQ ID NO.3 and SEQ ID NO.61 for mouse anti-human CD134 monoclonal antibody clone 20E5. Eleven amino acids of the N-terminus from heavy chains and 11 amino acids of the N-terminus from light chains were determined.

(b). RT PCR

Hybridoma cells of clone 20E5 and 12H3 were harvested from cell culture. Cells were washed with PBS, aliquoted in vials containing 5×10$^6$ cells, and stored as pellets at −80° C. Cell pellets were used to isolate RNA by using RNeasy Mini Isolation Kit (QIAGEN). RNA concentration was determined (A260 nm) and RNA was stored at −80° C. Total yield of isolated RNA: 27.3 μg and 58.4 μg for clone 20E5 and clone 12H3, respectively (A260/A280 ratio for both 1.9). By reverse transcriptase, cDNA was synthesized from 1 μg of RNA using the RevertAid™ H Minus First Strand cDNA Synthesis Kit (Fermentas), and stored at −20° C.

Based on the isotype (mouse kappa/IgG1) and Edman degradation analysis of mouse anti-human CD134 monoclonal antibody clone 20E5, following primers were designed to amplify V-regions of mouse anti-human CD134 monoclonal antibody clone 20E5:

| Primer No.* | Sequence** | SEQ ID No. | Direction | Gene |
|---|---|---|---|---|
| 201 | GACAGTTGGTGCAGCATCAG | 39 | antisense | mkappa |
| 266 | CACTGGATGGTGGGAAGATG | 40 | antisense | mkappa |
| 203 | GGCCAGTGGATAGACAGATG | 41 | antisense | mIgG1 |
| 204 | TGGACAGGGATCCAGAGTTC | 42 | antisense | mIgG1 |
| 259 | GCGAAGTACAAYTNCARCARWSNGG | 43 | sense | 20E5HC |
| 260 | GCGTACAATTACARCARWSNGGNCC | 44 | sense | 20E5HC |
| 265 | GCGATATACARATGACNCARAC | 45 | sense | 20E5LC |

*no. according to Bioceros internal coding system;
**degenerated primers: N = A, C, G, or T, Y = C or T, R = A or G, W = A or T, and S = G or C.

Based on the isotype (mouse kappa/IgG1) of mouse anti-human CD134 monoclonal antibody clone 12H3 and sense primers annealing to cDNAs encoding mouse signal peptides (partially based on Antibody Engineering Volume 1 Kontermann, Roland E.; Dübel, Stefan (Eds.), Springer Lab Manuals, 2nd ed., 2010), following primers were designed to amplify V-regions of mouse anti-human CD134 monoclonal antibody clone 12H3:

| Primer No.* | Sequence** | SEQ ID No. | Direction | Gene |
|---|---|---|---|---|
| 416 | CAGTGGATAGACAGATGGGGG | 46 | antisense | mIgG1 |
| 394 | ACTGGATGGTGGGAAGATGG | 47 | antisense | mkappa |
| 405 | ATGGGATGGAGCTRTATCATSYTCTT | 48 | sense | signal peptide |

-continued

| Primer No.* | Sequence** | SEQ ID No. | Direction | Gene |
|---|---|---|---|---|
| 410 | ATGGRATGGAGCKGGGTCTTTMTCTT | 49 | sense | signal peptide |
| 389 | ATGGGCWTCAAAGATGGAGTCACA | 50 | sense | signal peptide |

*no. according to Bioceros internal coding system;
**degenerated primers: N = A, C, G, or T, Y = C or T, R = A or G, W = A or T, and S = G or C, M = C or A and K = G or T..

Primers 201 and 266 are antisense designed to anneal within the constant region of the mouse kappa gene at position 214-232 and 236-255 respectively (based on accession number V00807 [version V00807.1]).

Primers 203 and 204 are antisense designed to anneal within the constant region of mouse IgG1 at position 115-134 and 221-240 respectively (based on accession number J00453 [version J00453.1]).

Primers 259 and 260 are sense degenerate primers (degeneracy respectively 512 and 256) annealing at the N-terminus (amino acid 1-8 and 2-9 respectively) of the heavy chain of mouse anti-human CD134 antibody clone 20E5 based on Edman degradation.

Primer 265 is a sense degenerate primer (degeneracy of 16) annealing at the N-terminus (amino acid 1-7) of the light chain of mouse anti-human CD134 antibody clone 20E5 based on Edman degradation.

Primer 416 is antisense designed to anneal within the constant region of mouse IgG1 at position 111-131 (based on accession number J00453 [version J00453.1]).

Primer 394 is antisense designed to anneal within the constant region of the mouse kappa gene at position 235-254 (based on accession number V00807 [version V00807.1]).

Primers 389, 405 and 410 are degenerated primers (degeneracy respectively 2, 8 and 8) annealing with signal peptide sequences of murine antibodies. Primer 389 was designed for the light chain, primers 405 and 410 for the heavy chain.

Primers 201, 266, 203, 204, 259, 260, and 265 were used in various combinations to amplify variable regions of mouse anti-human CD134 antibody clone 20E5, and primers 416, 394, 405, 410, and 389 were used in various combinations to amplify variable regions of mouse anti-human CD134 antibody clone 12H3. Various different PCRs were done using generated cDNA of both clones as template.

Accuprime™ Pfx DNA Polymerase (Invitrogen) was used to amplify variable regions of heavy and light chains of both mouse anti-human CD134 antibody clone 20E5 and clone 12H3. The PCR products were analyzed on a 1% agarose gel. Products of PCR reactions were gel-purified and cloned in the pCR-Blunt II-TOPO® vector for sequence analysis. From plasmids containing a PCR insert, cloned inserts were analysed by DNA sequencing (performed by ServicXS B.V., Leiden, The Netherlands or Macrogen, Amsterdam, The Netherlands) using T7 to obtain the consensus sequence for V-regions of mouse anti-human CD134 antibodies clones 20E5 and 12H3. Eleven informative sequences heavy chain reactions and 3 informative light chain sequence reactions were obtained for mouse anti-CD134 antibody clone 20E5. Five informative sequences heavy chain reactions and 3 informative light chain sequence reactions were obtained for mouse anti-CD134 antibody clone 12H3. Based on this information, consensus sequences of V-regions of both antibodies were determined (see SEQ ID NO. 4, 5, 12 and 13).

The listing or discussion of an apparently prior-published document in this specification should not necessarily be taken as an acknowledgement that the document is part of the state of the art or is common general knowledge.

Example 5

Generation of Chimeric Human IgG4/Kappa and/or Human IgG1/Kappa (i.e., Swapping Mouse Constant Domains for Constant Human IgG/Kappa Domains) Anti-Human CD134 Monoclonal Antibodies Clones 20E5 an 12H3

Based on determined murine V-regions (see Example 4 (b) above) of mouse anti-CD134 antibodies clones 20E5 and 12H3, a design was made to generate chimeric human antibody versions. To this end, CHO cell-optimized cDNA sequences (see SEQ ID NO. 20 (coding for chimeric human heavy IgG4 chain clone 20E5), SEQ ID NO. 21 (coding for chimeric human light κ chain clone 20E5), SEQ ID NO. 22 (coding for chimeric human heavy IgG1 chain clone 20E5), SEQ ID NO. 23 (coding for chimeric human heavy IgG4 chain clone 12H3), and SEQ ID NO. 24 (coding for chimeric human light κ chain clone 12H3)), were ordered at GENEART (Regensburg, Germany), which encoded for a murine signal peptide followed by either the variable light chain linked to human kappa constant region, or followed by the variable heavy chain linked to human IgG constant region. This design was done for both antibodies; for clone 20E5, the variable heavy chain was linked to human IgG4 or to human IgG1 constant region; for clone 12H3, the variable heavy chain region was linked to human IgG4 constant region. Using suitable restriction enzymes, generated cDNAs were subcloned in pcDNA3.1-derived expression plasmids. Chimeric antibodies were expressed using FreeStyle™ MAX CHO (CHO-S cells) Expression System (Invitrogen). Expressed antibodies were purified using affinity chromatography protein A columns (GE Healthcare). For chimeric amino acid sequences, see SEQ ID NO. 25, 26, 27, 28, and 29.

Example 6

Binding Characterization of Chimeric Human IgG4/Kappa and/or IgG1/Kappa Anti-Human CD134 Monoclonal Antibody Clone 20E5

(a). Binding Characteristics of Human IgG4κ Anti-Human CD134 Monoclonal Antibody Clone 20E5 on PHA-Stimulated Human CD134 Expressing CD4 Positive T Lymphocytes PHA-stimulated (at 10 μg/mL for 1 day; see above) human CD134 expressing T lymphocytes were generated. Cells were harvested and put at $1\text{-}2\times10^6$ cells/mL in ice-chilled PBS/BSA/NaN$_3$. Cells were incubated with 0, 0.007, 0.02, 0.07, 0.2, 0.6, 1.9, 5.6, 16.7, 50.0 μg/mL chimeric human IgG4κ anti-human CD134 antibody clone 20E5 for 30 minutes at 4° C. After extensive washing in PBS/BSA/NaN$_3$, cells were subsequently incubated with 1:50 diluted FITC-conjugated mouse anti-human IgG4 antibodies (Sigma) for 30 minutes at 4° C. After extensive washing in PBS/BSA/NaN$_3$, cells were incubated with 1:10 diluted PE-conjugated mouse anti-human CD4 antibody (BD Biosciences) for 30 minutes at 4° C. After extensive washing in PBS/BSA/NaN$_3$, cells were fixed in 2% formaldehyde in PBS/BSA/NaN$_3$ for 30 minutes at 4° C. Binding of antibodies was measured using flow cytometry (FACSCalibur; BD Biosciences).

Chimeric human IgG4κ anti-human CD134 antibody clone 20E5 saturated human CD134 surface molecules on PHA-stimulated CD4$^{positive}$ T lymphocytes at approximately 5.0-10.0 μg/mL (data not shown). Half maximal binding was observed at ≈1.0 μg/mL for chimeric human IgG4κ anti-human CD134 antibody clone 20E5 (data not shown).

(b). Binding of Chimeric Human IgG4κ Anti-Human CD134 Monoclonal Antibody Clone 20E5 on PHA-Stimulated Human CD134 Expressing CD4 Positive and CD8 Positive T Lymphocytes PHA-stimulated (at 10 μg/mL for 1 day; see above) human CD134 expressing T lymphocytes were generated. Cells were harvested and put at 1-2×10$^6$ cells/mL in ice-chilled PBS/BSA/NaN$_3$. Cells were incubated with or without 20.0 μg/mL chimeric human IgG4κ anti-human CD134 antibody clone 20E5 for 30 minutes at 4° C. After extensive washing in PBS/BSA/NaN$_3$, cells were subsequently incubated for 30 minutes at 4° C. with 1:200 diluted PE-conjugated goat anti-human IgG (Fcγ specific) antibodies (Jackson ImmunoResearch) for 30 minutes at 4° C. After extensive washing in PBS/BSA/NaN$_3$, cells were incubated with 1:10 diluted FITC-conjugated mouse anti-human CD4 antibody (BD Biosciences) or with 1:10 diluted FITC-conjugated mouse anti-human CD8 antibody (BD Biosciences) to detect T lymphocyte subpopulations. After extensive washing in PBS/BSA/NaN$_3$, cells were fixed in 2% formaldehyde in PBS/BSA/NaN$_3$ for 30 minutes at 4° C. Binding of antibodies was measured using flow cytometry (FACSCalibur; BD Biosciences).

Chimeric human IgG4κ anti-human CD134 antibody clone 20E5 demonstrated positive staining on the PHA-activated human CD4$^{positive}$ T lymphocyte subpopulation, and low positive staining on the PHA-activated human CD8$^{positive}$ T lymphocyte subpopulation (data not shown).

(c). Binding of Chimeric Human IgG4κ Anti-Human CD134 Monoclonal Antibody Clone 20E5 on Anti-Human CD3/Anti-Human CD28 Antibody Stimulator Beads-Stimulated Human CD134 Expressing CD4 Positive and CD8 Positive T Lymphocytes Human peripheral blood mononuclear cells (PBMC) from healthy donors (informed consent) were isolated by density centrifugation on Lymphoprep (1.077 g/mL; Nycomed). Subsequently, 1×10$^6$ PBMC/mL in RPMI-1640 culture medium (Gibco) containing 10% fetal calf serum (Bodinco) and 50 μg/mL gentamycin (Gibco) were stimulated with mouse anti-human CD3/mouse anti-human CD28 antibody stimulator beads (CD3/CD28 beads; Invitrogen) at 1 bead/4 cells in the absence or presence of 25 U/mL recombinant human interleukin-2 (PeproTech) at 37° C./5% CO$_2$ for 1 day. After culture, PBMC were harvested and put at 1-2×10$^6$ cells/mL in ice-chilled PBS/BSA/NaN$_3$. Cells were incubated with or without 20.0 μg/mL chimeric human IgG4κ anti-human CD134 antibody clone 20E5 for 30 minutes at 4° C. After extensive washing in PBS/BSA/NaN$_3$, cells were subsequently incubated with 1:200 diluted PE-conjugated goat anti-human IgG (Fcγ specific) antibodies (Jackson ImmunoResearch) for 30 minutes at 4° C. After extensive washing in PBS/BSA/NaN$_3$, cells were incubated for 30 minutes at 4° C. with 1:10 diluted FITC-conjugated mouse anti-human CD4 antibody (BD Biosciences) or with 1:10 diluted FITC-conjugated mouse anti-human CD8 antibody (BD Biosciences) to detect T lymphocyte subpopulations. After extensive washing in PBS/BSA/NaN$_3$, cells were fixed in 2% formaldehyde in PBS/BSA/NaN$_3$ for 30 minutes at 4° C. Binding of antibodies was measured using flow cytometry (FACSCalibur; BD Biosciences).

Figure 14:
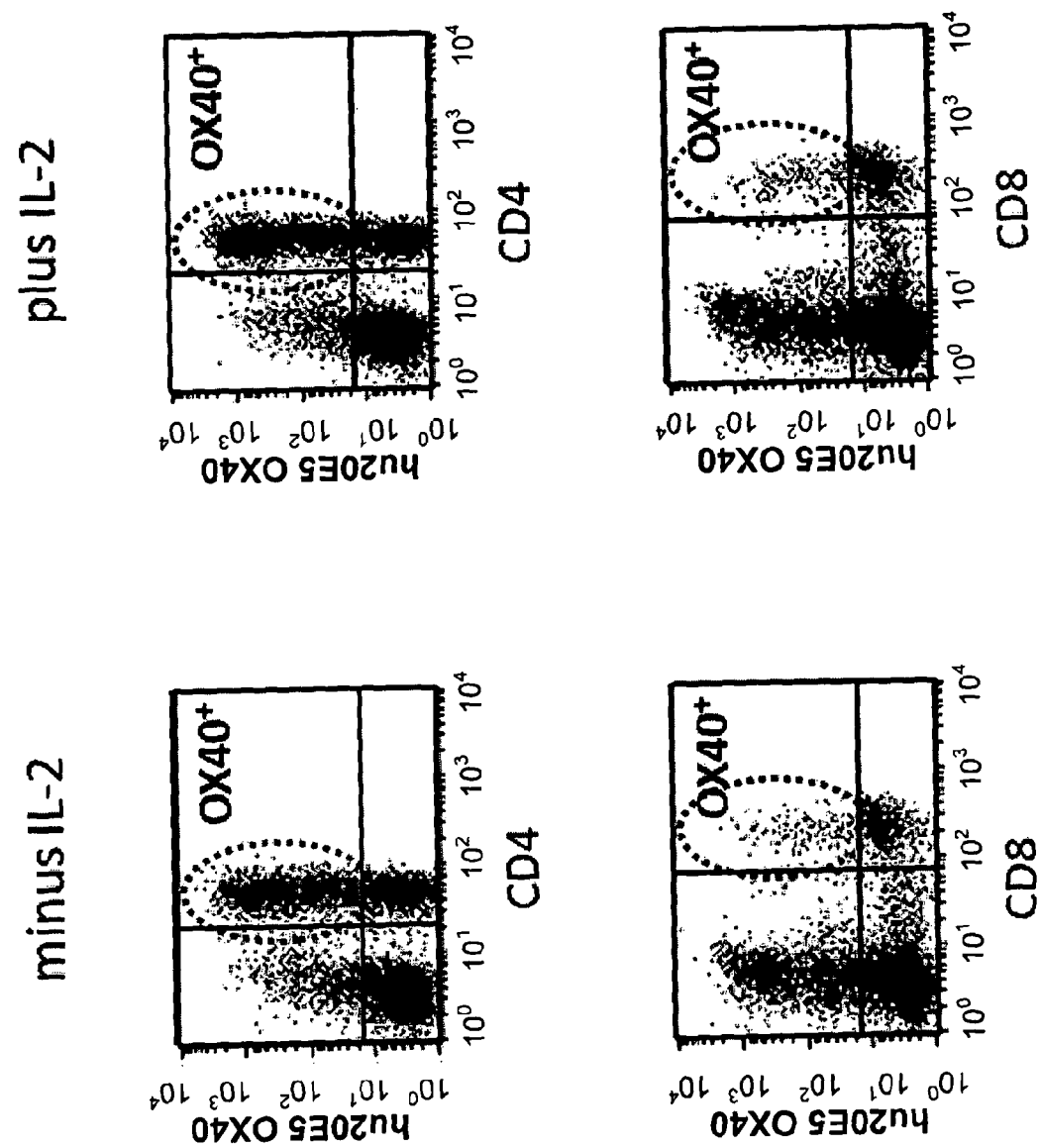
FIG. 14. Binding of chimeric human IgG4κ anti-human CD134 antibody clone 20E5 on (minus and plus IL-2) CD3/CD28 beads-stimulated human CD134 expressing CD4 T lymphocytes and CD8 T lymphocytes.

As shown in FIG. 14, chimeric human IgG4κ anti-human CD134 antibody clone 20E5 demonstrated positive staining on the CD3/CD28 beads-activated human CD4$^{positive}$ T lymphocyte subpopulation, and low positive staining on the CD3/CD28 beads-activated human CD8$^{positive}$ T lymphocyte subpopulation. No apparent effect was observed using recombinant human IL-2 supplement.

Example 7

Biological Characterization of Chimeric Human IgG4/Kappa Anti-Human CD134 Monoclonal Antibody Clone 20E5

(a). Proliferation of PHA-Stimulated Human CD134 Expressing T Lymphocytes after Treatment with Chimeric Human IgG4κ Anti-Human CD134 Monoclonal Antibody Clone 20E5

PHA-stimulated (10 μg/mL for 1 day; see above) human CD134 expressing T lymphocytes were generated. Cells were harvested and suspended at 2×10$^6$ cells/mL in RPMI culture medium (Gibco) containing 10% fetal calf serum (Bodinco) and 50 μg/mL gentamycin (Gibco). Cells were seeded at 0.1×10$^6$ cells/100 μL/well (i.e., 1×10$^6$ cells/mL) in 96-wells flat-bottom plates (Corning), and were exposed to 25.0 μg/mL chimeric human IgG4κ anti-human CD134 antibody clone 20E5 or to 25.0 μg/mL control human IgG4κ anti-human CD40 antibody (PG102; Pangenetics), or to 1.0 μg/mL polyhistidine-tagged recombinant human OX40L (in the presence of 1:5 molar ratio mouse anti-polyhistidine antibody; R&D Systems) at 37° C./5% CO$_2$ for 6 days. After 6 days, cell proliferation was measured using the colorimetric (BrdU incorporation) Cell Proliferation ELISA™ (Roche) and an ELISA reader (BioRad) at A450 nm.

Figure 15:
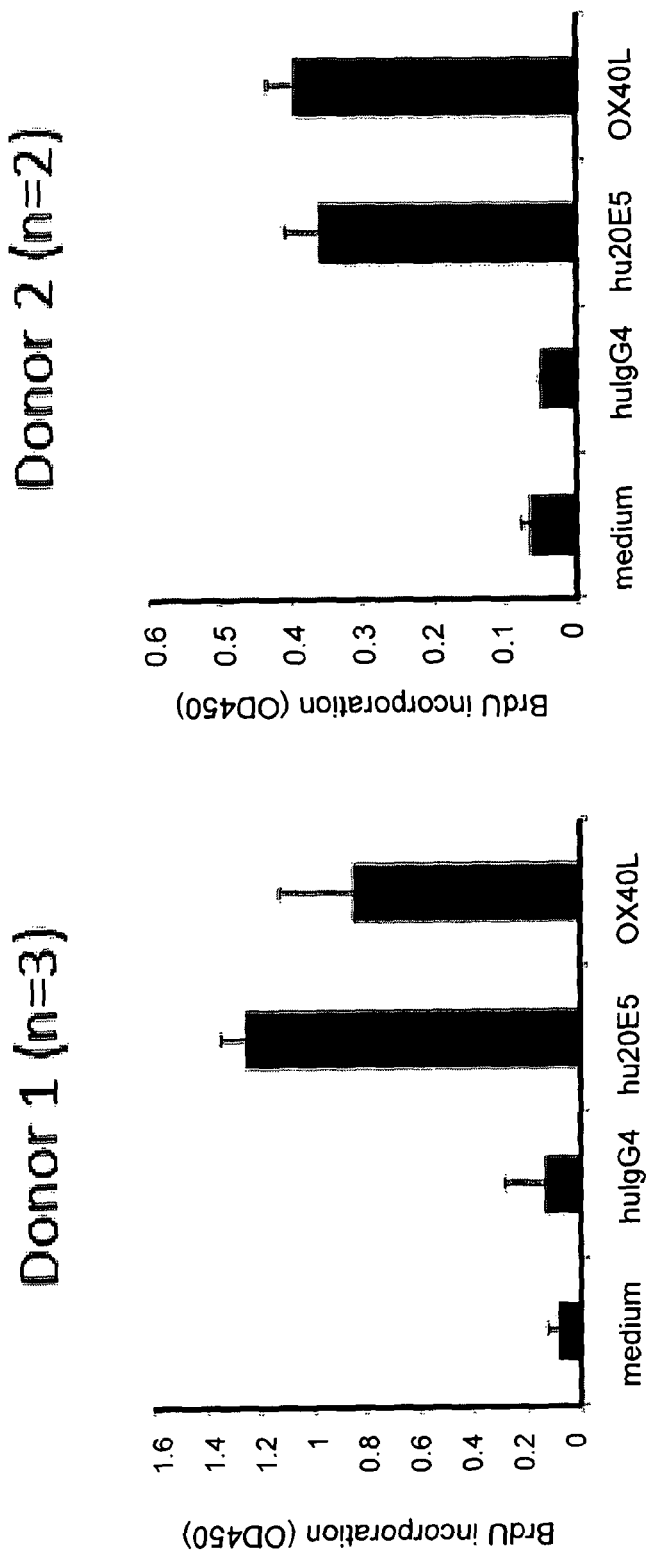
FIG. 15. Effect of chimeric human IgG4κ anti-human CD134 antibody clone 20E5 or human OX40L on proliferation of PHA-M-stimulated human CD134 expressing T lymphocytes.
Figure 15:
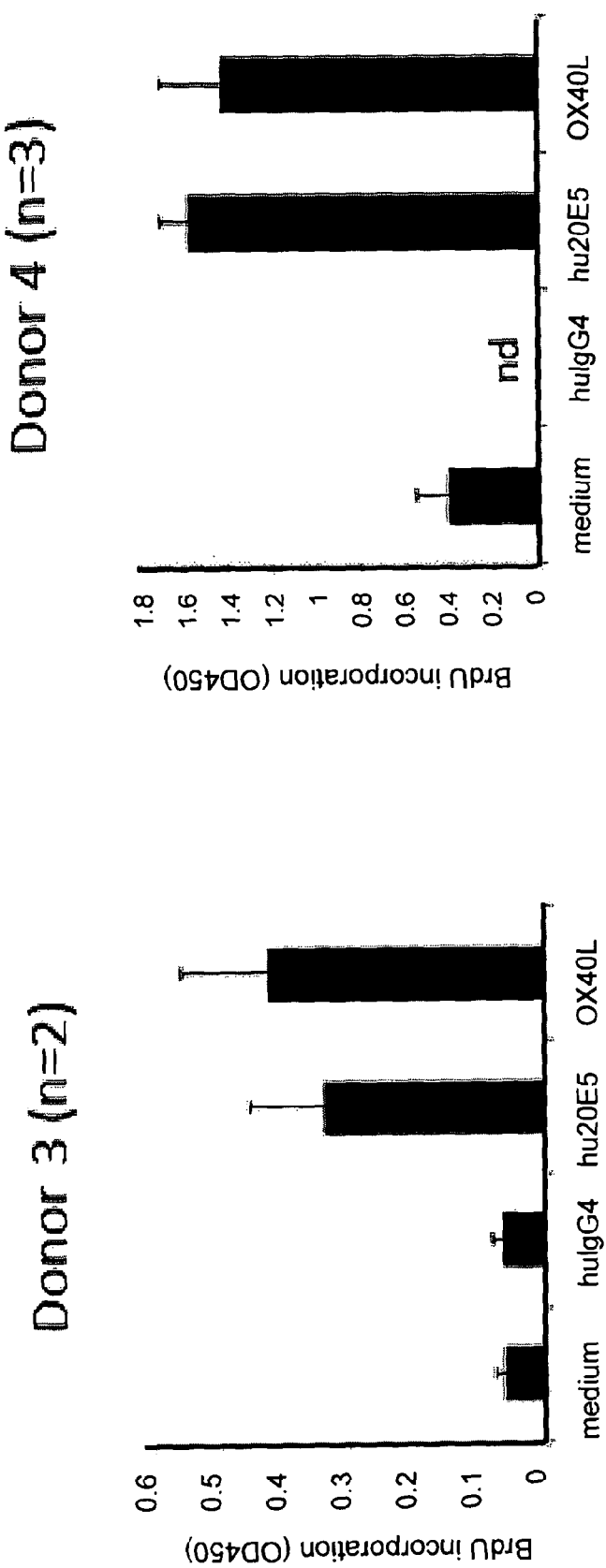
Figure 15:
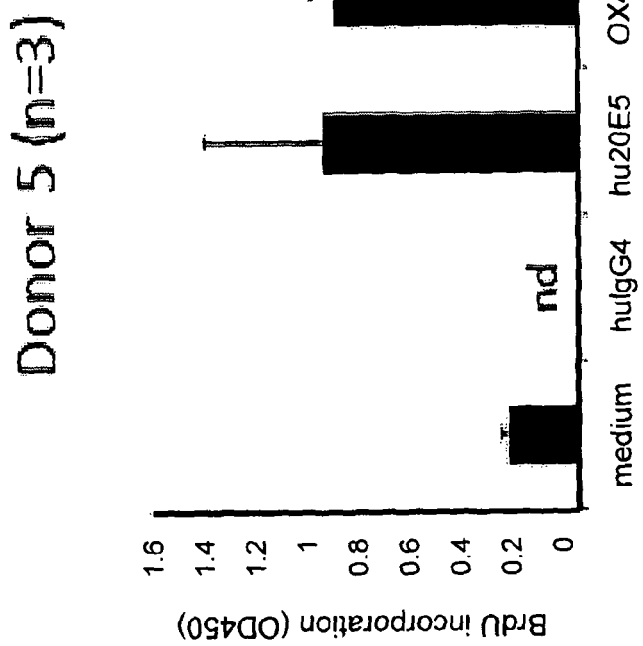

As shown in FIG. 15 (mean±SD), chimeric human IgG4κ anti-human CD134 antibody clone 20E5 (hu20E5) and human OX40L induced proliferation in PHA-stimulated human CD134 expressing T lymphocytes. Non-treated (medium only) or treatment with control human IgG4κ anti-human CD40 antibody (huIgG4) did not demonstrate any effect on PHA-stimulated human CD134 expressing T lymphocyte proliferation.

(b). Proliferation of PHA-Stimulated Human CD134 Expressing T Lymphocytes after Treatment with Chimeric Human IgG4κ Anti-Human CD134 Monoclonal Antibody Clone 20E5 in Combination with Recombinant Human OX40L PHA-stimulated (10 μg/mL for 1 day; see above) human CD134 expressing T lymphocytes were generated. Cells were harvested and suspended at 2×10$^6$ cells/mL in RPMI culture medium (Gibco) containing 10% fetal calf serum (Bodinco) and 50 μg/mL gentamycin (Gibco). Cells were seeded at 0.1×10$^6$ cells/100 μL/well (i.e., 1×10$^6$ cells/mL) in 96-wells flat-bottom plates (Corning), and were exposed to 0, 0.025, 0.25, 2.5, or 25.0 μg/mL chimeric human IgG4κ anti-human CD134 antibody clone 20E5, or/and in combination with 0, 0.01, 0.1, or 1.0 μg/mL polyhistidine-tagged recombinant human OX40L (in the presence of 1:5 molar ratio mouse anti-polyhistidine antibody; R&D Systems) at 37° C./5% $CO_2$ for 6 days. After 6 days, cell proliferation was measured using the colorimetric (BrdU incorporation) Cell Proliferation ELISA™ (Roche) and an ELISA reader (BioRad) at A450 nm.

Figure 16:
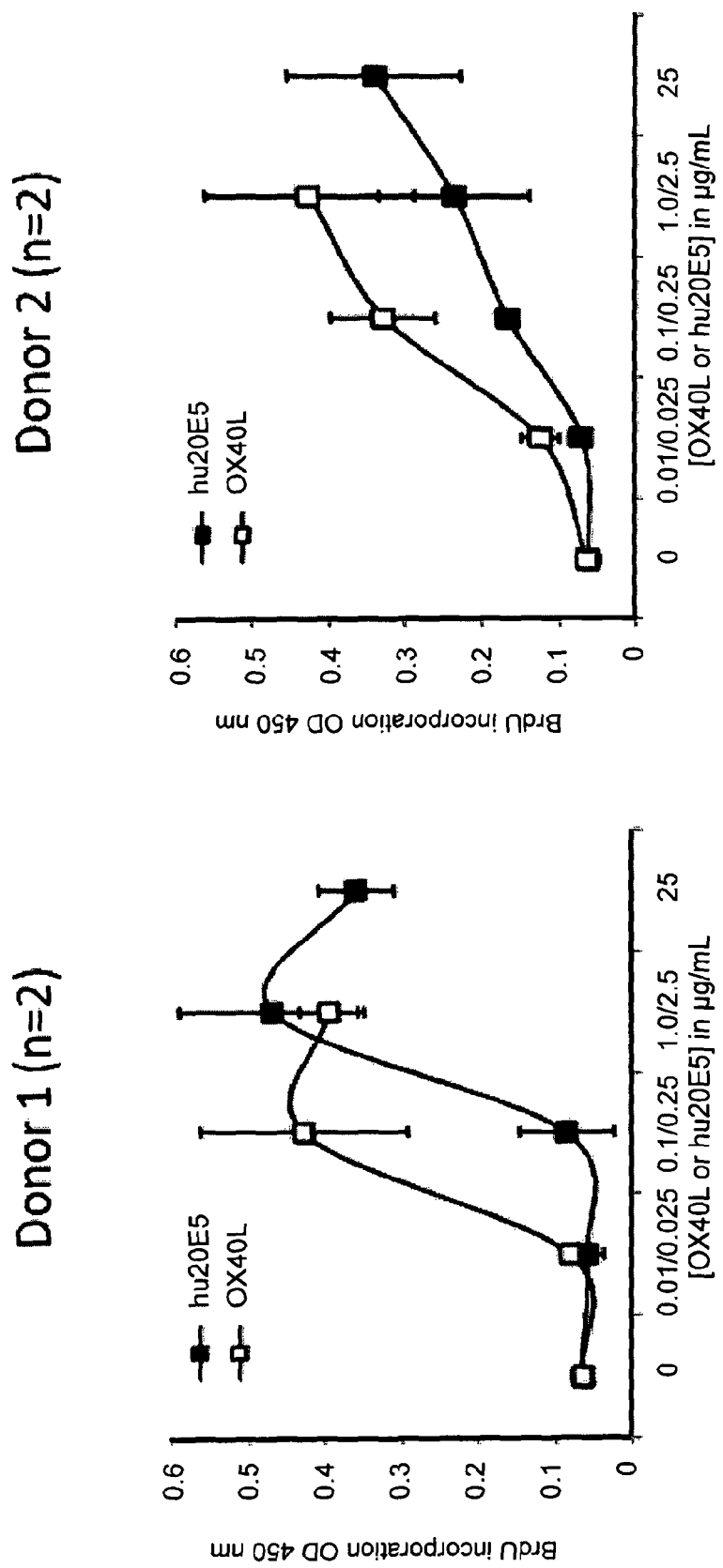
FIG. 16. Dose effect of exposure to chimeric human IgG4κ anti-human CD134 antibody clone 20E5 or to human OX40L on proliferation of PHA-M-stimulated human CD134 expressing T lymphocytes FIG. 17. Effect of combining chimeric human IgG4κ anti-human CD134 antibody clone 20E5 with human OX40L on proliferation of PHA-M-stimulated human CD134 expressing T lymphocytes.

As shown in FIG. 16 (mean±SD), chimeric human IgG4κ anti-human CD134 antibody clone 20E5 (hu20E5) and human OX40L dose-dependently induced proliferation in PHA-stimulated human CD134 expressing T lymphocytes. Chimeric human IgG4κ anti-human CD134 antibody clone 20E5 donor-dependently induced proliferation at either 2.5 and 25 μg/mL (donor 1) or at 0.25, 2.5, and 25 μg/mL (donor 2). In addition, human OX40L donor-dependently induced proliferation at either 0.1 and 1.0 μg/mL (donor 1) or at 0.01, 0.1, and 1.0 μg/mL (donor 2).

Figure 17:
Figure 17:
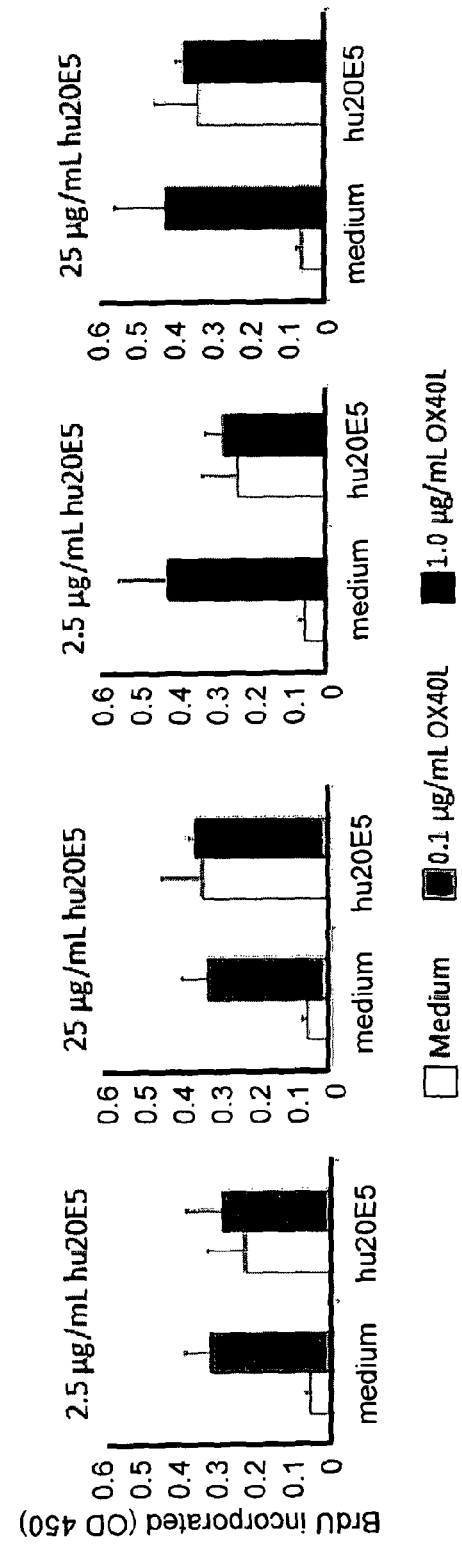

As shown in FIG. 17 (mean±SD), the combination of chimeric human IgG4κ anti-human CD134 antibody clone 20E5 (hu20E5) at 2.5 and 25 μg/mL (or at lower concentrations; data not shown) with human OX40L at 0.1 and 1.0 μg/mL (or at lower concentrations; data not shown) did not demonstrate any reciprocal (i.e., synergistic or additive, or even inhibitory) effects on proliferation in PHA-stimulated human CD134 expressing T lymphocytes.

(c). Proliferation of Anti-Human CD3/Anti-Human CD28 Antibody Stimulator Beads-Stimulated Human CD134 Expressing T Lymphocytes after Treatment with Chimeric Human IgG4κ Anti-Human CD134 Monoclonal Antibody Clone 20E5

Human peripheral blood mononuclear cells (PBMC) from healthy donors (informed consent) were isolated by density centrifugation on Lymphoprep (1.077 g/mL; Nycomed). Subsequently, PBMC were seeded at $0.1 \times 10^6$ cells/100 μL/well (i.e., $1 \times 10^6$ cells/mL) in 96-wells flat-bottom plates (Corning) in RPMI-1640 culture medium (Gibco) containing 10% fetal calf serum (Bodinco) and 50 μg/mL gentamycin (Gibco), and were stimulated with mouse anti-human CD3/mouse anti-human CD28 antibody stimulator beads (CD3/CD28 beads; Invitrogen) at 1 bead/2 cells in the absence or presence of 25 U/mL recombinant human interleukin-2 (PeproTech) at 37° C./5% $CO_2$. After 1 day or after 2 days, these (minus and plus interleukin-2) CD3/CD28 beads-stimulated human CD134 expressing T lymphocytes were exposed to 25.0 μg/mL chimeric human IgG4κ anti-human CD134 antibody clone 20E5 or to 1.0 μg/mL polyhistidine-tagged recombinant human OX40L (in the presence of 1:5 molar ratio mouse anti-polyhistidine antibody; R&D Systems) at 37° C./5% $CO_2$ for 6 days or for 5 days, respectively. Cells, which were initially stimulated with combination of CD3/CD28 beads plus recombinant human interleukin-2, were re-stimulated 1 day prior to cell proliferation measurements with 25 U/mL of recombinant human interleukin-2. After 6 days or after 5 days exposure to chimeric human IgG4κ anti-human CD134 antibody clone 20E5 or to human OX40L, cell proliferation was measured using the colorimetric (BrdU incorporation) Cell Proliferation ELISA™ (Roche) and an ELISA reader (BioRad) at A450 nm.

Figure 18:
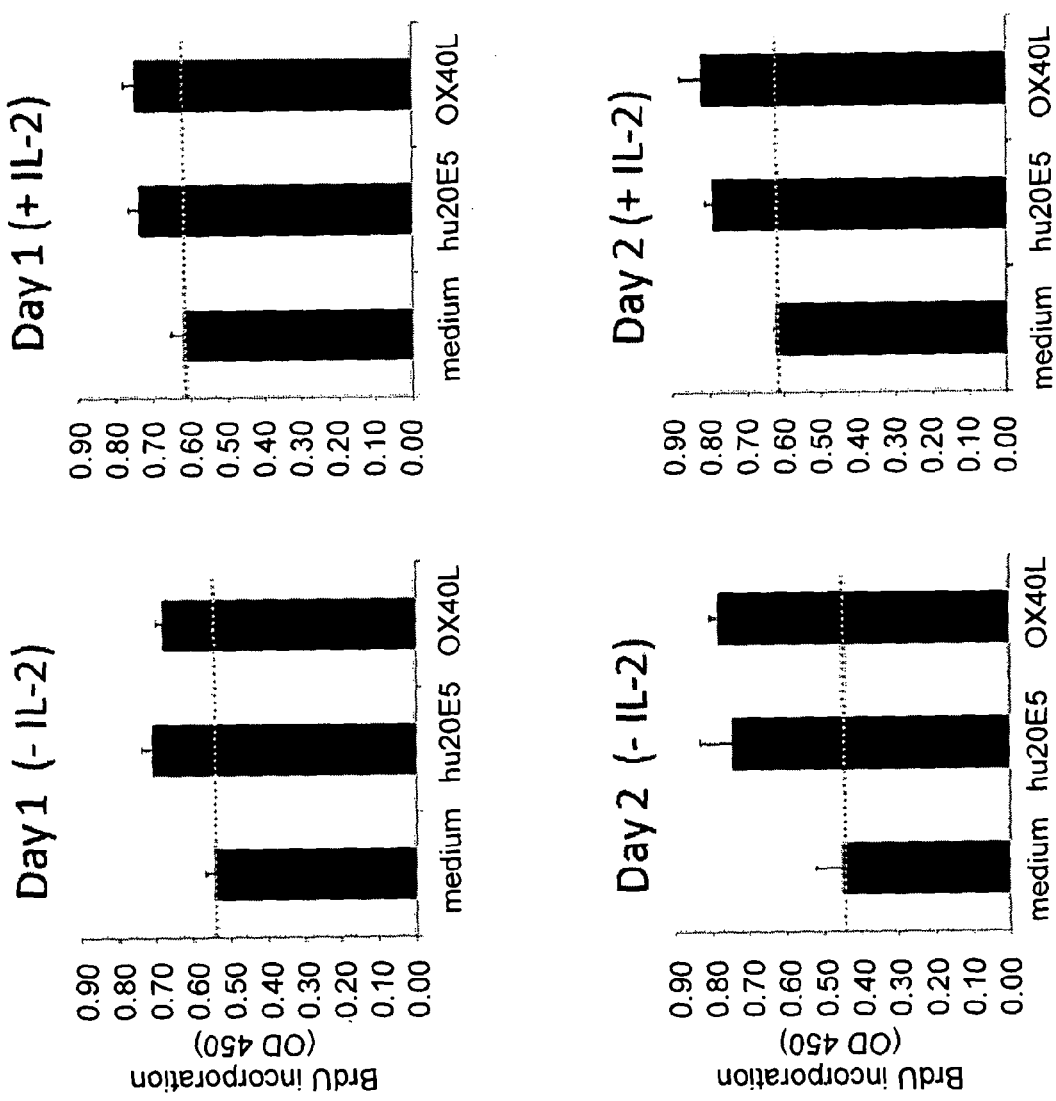
FIG. 18. Effect of chimeric human IgG4κ anti-human CD134 antibody clone 20E5 or human OX40L on proliferation of (minus and plus IL-2) CD3/CD28 beads-stimulated human CD134 expressing T lymphocytes.

As shown in FIG. 18 (mean±SD, n=3 using one donor), although CD3/CD28 stimulator beads alone induced considerable proliferation in human CD134 expressing T lymphocytes (i.e., medium), chimeric human IgG4κ anti-human CD134 antibody clone 20E5 (hu20E5) and human OX40L induced additional proliferation in CD3/CD28 beads-stimulated human CD134 expressing T lymphocytes. Addition of interleukin-2 only seemed to enhance basal (i.e., medium) proliferation in CD3/CD28 beads-stimulated human CD134 expressing T lymphocytes.

(d). Immunostimulatory Responses in Rhesus Macaque Monkeys after Treatment with Human (Chimeric) Anti-Human CD134 Antibodies Clones 12H3 and 20E5

Non-human primates rhesus macaque monkeys may be immunized with the simian immunodeficiency virus protein, gp130, as described by Weinberg et al. (J Immunother 2006; 29: 575-585).

The draining lymph nodes from immunized monkeys treated with human (e.g., chimeric or humanized or deimmunized; e.g., subclass human IgG1 or IgG4) anti-human CD134 antibodies clones 12H3 and 20E5 are expected to show enlarged lymph nodes compared with control immunized monkeys. Human (e.g., chimeric or humanized or deimmunized) anti-human CD134 antibodies clones 12H3-treated and 20E5-treated monkeys are expected to show increased gp130-specific antibody titres, and increased long-lived T-cell responses, compared with controls. There should be no overt signs of toxicity in (e.g., chimeric or humanized or deimmunized) anti-human CD134 antibody clone 12H3-treated or clone 20E5-treated monkeys.

Example 8

Characterization of Human CD134 Domains and Epitopes Recognized by Mouse Anti-Human CD134 Monoclonal Antibody Clones 12H3 and 20E5

(a). Binding of Mouse Anti-Human CD134 Monoclonal Antibodies Clones 12H3 and 20E5 with Non-Reduced and Reduced Recombinant Human CD134:Human Fcγ Fusion Protein (Western Blotting)

Thirteen hundred or 650 ng/lane (for Coomassie brilliant blue staining) or 250 ng/lane (for western blotting) recombinant human CD134:human Fcγ (IgG1) fusion protein (R&D Systems) was electrophorized using 4-12% Tris-Bis gels and MOPS running buffer (Invitrogen) under a variety of non-reducing and reducing conditions (see FIG. 19-A) in pre-cast LDS-PAGE denaturing electrophoresis NuPage® Novex® system. Then, recombinant human CD134:human Fcγ fusion protein was either stained with Coomassie brilliant blue (BioRad) or electro-blotted onto a polyvinylidene fluoride (PDVF) transfer membrane (Millipore). After blocking with PBS/0.05% Tween 20/1% BSA fraction V (Roche) for 20 min at RT, PDVF membranes were incubated with 100 ng/mL mouse anti-human CD134 monoclonal antibody clone 12H3 or 20E5 for 1 hour at RT. In parallel, 100 ng/mL mouse IgG1κ isotype control antibody (BD Biosciences) was used as a negative control. After extensive washing in PBS/0.05% Tween 20, binding of mouse anti-human CD134 monoclonal antibody clone 12H3 or 20E5 was determined with 1:5000 diluted horseradish peroxidase-conjugated goat anti-mouse Fcγ-specific antibodies (Jackson ImmunoResearch) for 1 hour at RT, followed by a ready-to-use solution of TMB substrate (Sigma) for colorimetric detection.

Figure 19:
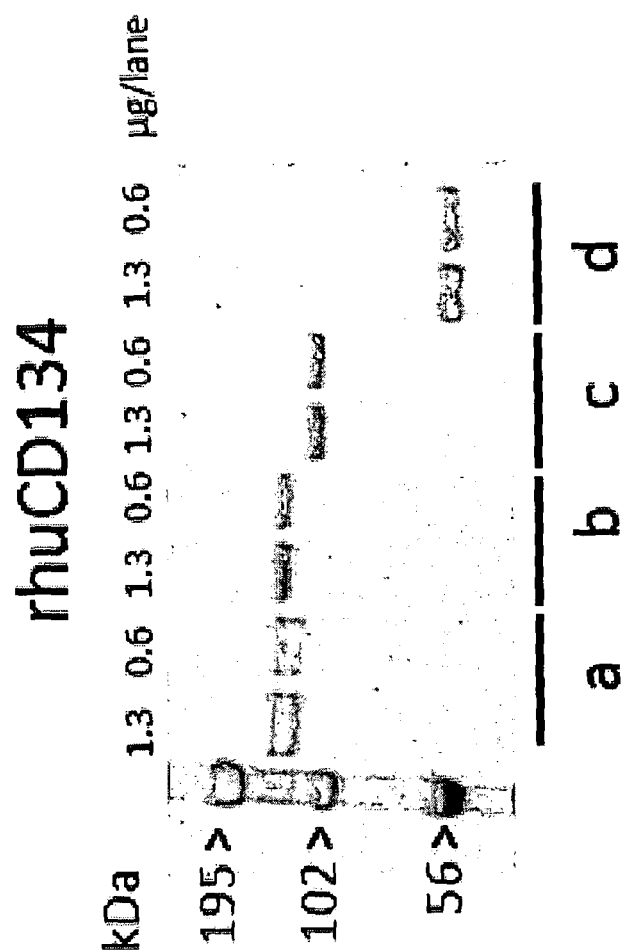
FIG. 19. Binding of mouse anti-human CD134 antibodies clones 12H3 and 20E5 with non-reduced and reduced recombinant human CD134:human Fcγ fusion protein. (A) Examined non-reducing (a, b) and reducing (c, d) conditions. (B) Electrophoretic migration patterns of recombinant human CD134:human Fcγ fusion protein (rhuCD134) under non-reducing (a, b) and reducing (c, d) conditions using Coomassie brilliant blue staining. (C) Western blot of non-reducing (a, b) and reducing (c, d) recombinant human CD134:human Fcγ fusion protein exposed to mouse IgG1κ isotype control antibody (mIgG1) or to mouse anti-human CD134 antibodies clones 12H3 and 20E5 (m12H3 and m20E5, respectively).
Figure 19:
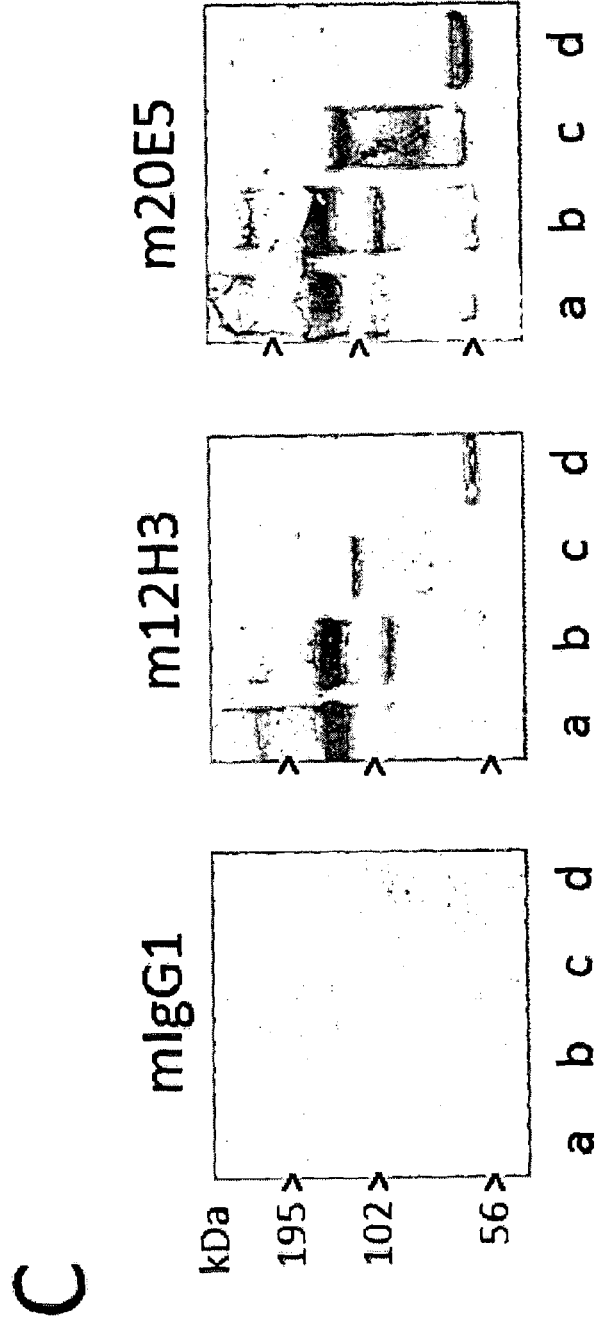

As shown in FIG. 19-B, recombinant human CD134:human Fcγ fusion protein under non-reducing (and LDS denaturing without and with heat denaturing, condition a and b, respectively) conditions demonstrated a molecular mass of ≈130-140 kDa. Non-reduction without heating (condition a) showed two bands at close proximity, which suggested that a fraction of recombinant human CD134:human Fcγ fusion protein was incompletely denatured/ unfolded. Non-reduction with heating (condition b) showed one band, which suggested that recombinant human CD134:human Fcγ fusion protein was completely denatured/unfolded. Recombinant human CD134:human Fcγ fusion protein under reducing (and LDS denaturing without and with heat denaturing, condition c and d, respectively) conditions resulted in bands at ≈110 kDa (condition c) and at ≈60-65 kDa (condition d). Former observation suggested incomplete reduction of recombinant human CD134:human Fcγ fusion protein, and latter observation suggested complete reduction/breakage of disulfide bridges joining two human IgG1-derived Fcγ-fragments within each recombinant human CD134:human Fcγ fusion protein molecule.

As shown in FIG. 19-C, both mouse anti-human CD134 antibodies clone 12H3 and clone 20E5 recognized recombinant human CD134:human Fcγ fusion protein under non-reducing (and LDS denaturing without and with heat denaturing, condition a and b, respectively) conditions at predominantly ≈130 kDa. In contrast, mouse anti-human CD134 antibody clone 12H3 showed only a slight binding with recombinant human CD134:human Fcγ fusion protein under reducing (and LDS denaturing without and with heat denaturing, condition c and d, respectively) conditions, whereas mouse anti-human CD134 antibody clone 20E5 showed a strong binding to recombinant human CD134:human Fcγ fusion protein under reducing (and LDS denaturing without and with heat denaturing, condition c and d, respectively) conditions.

These results demonstrated that mouse anti-human CD134 antibodies clone 12H3 and clone 20E5 specifically recognized human CD134. Furthermore, these results demonstrated that mouse anti-human CD134 antibodies clone 12H3 and clone 20E5 seemed to recognize dissimilar human CD134 epitopes, which is evidenced by respective slight binding (clone 121-13) vs strong binding (clone 20E5) with recombinant human CD134:human Fcγ fusion protein under reducing (and LDS denaturing with and without heat denaturing) conditions. These results suggested that mouse anti-human CD134 antibody clone 12H3 recognized an epitope on human CD134, which is not sensitive to denaturation (LDS and heat treatment) and sensitive to reduction (i.e., breakage of disulphide bridge(s)—most likely, cysteine-rich domains (CRD)-related—by DTT). These results suggested that mouse anti-human CD134 antibody clone 20E5 recognized an epitope on human CD134, which is not sensitive to denaturation (LDS and heat treatment) and not sensitive to reduction (i.e., breakage of disulphide bridge(s)—most likely, CRD-related—by DTT).

(b). Binding of Mouse Anti-Human CD134 Monoclonal Antibodies Clones 12H3 and 20E5 with Full-Length Human CD134 Construct and Various Truncated Human CD134 Constructs Expressed on 293-F Cell Line (Domain Mapping)

In order to analyze the fine specificity of mouse anti-human CD134 monoclonal antibodies clones 12H3 and 20E5, the location of epitope(s) recognized by mouse anti-human CD134 monoclonal antibodies clones 12H3 and 20E5 was determined by domain mapping. The ability of mouse anti-human CD134 monoclonal antibodies clones 12H3 and 20E5 to bind to truncated human CD134 constructs, expressed on the surface of (HEK-derived) 297-F cells, was determined by FACS analysis.

Figure 20:
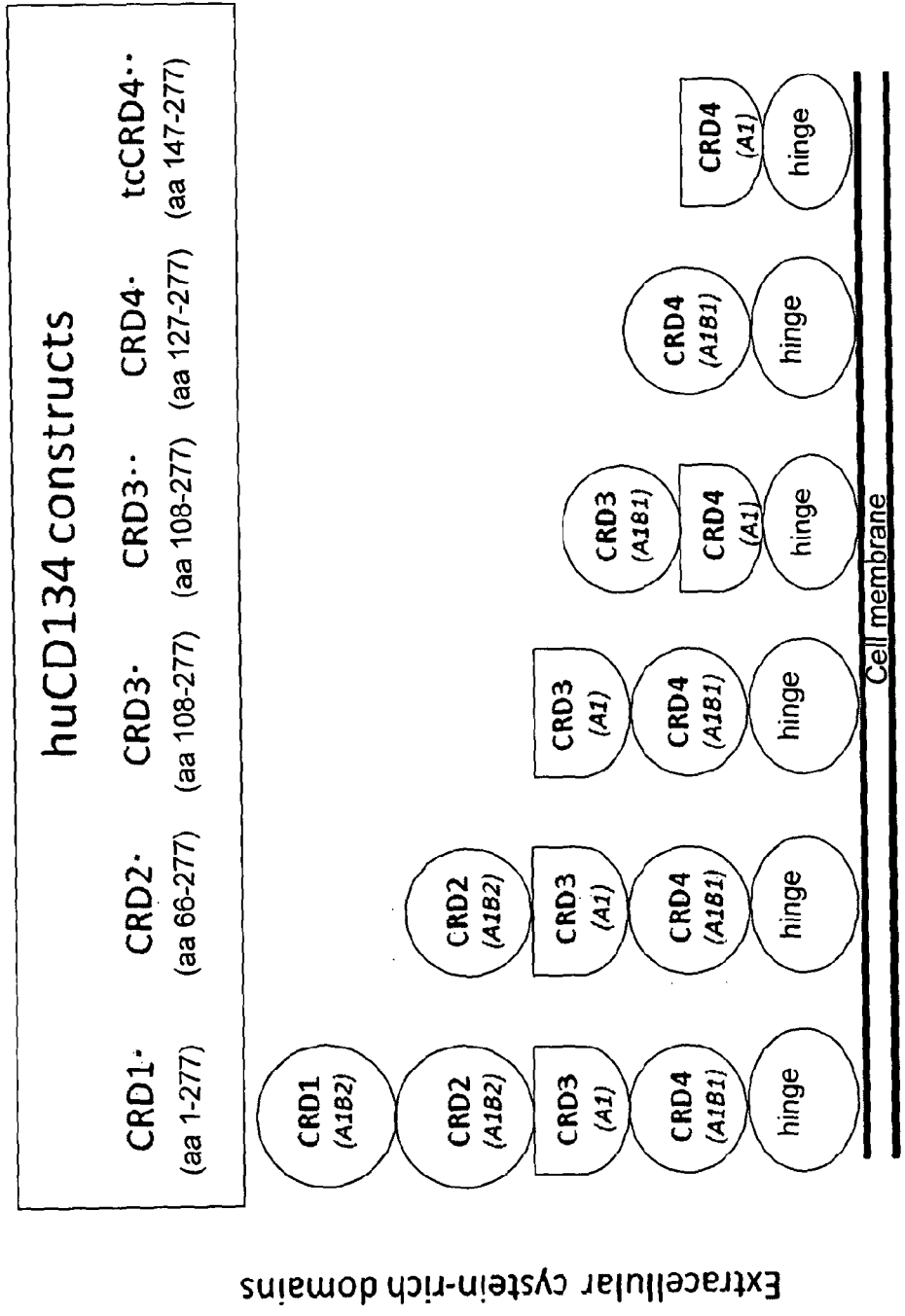
FIG. 20. Schematic representation of cysteine-rich domains (CRD) in full-length human CD134 (denoted as 'CRD1') and in various truncated human CD134 forms (denoted as 'CRD2', 'CRD3', 'CRD4', and 'truncated (tc) CRD4').

Based on literature (Swiss-Prot: P43489.1; Latza et al. Eur J Immunol 1994; 24: 677-683; Bodmer et al. Trends Biochem Sci 2002; 27: 19-26; Compaan et al. Structure 2006; 14: 1321-1330; US patent 2011/0028688 A1), cysteine-rich domains (CRD) and a hinge-like structure in the extracellular region of human CD134 were identified. CRDs are coded CRD1, CRD2, (truncated) CRD3, (truncated) CRD4 (see FIG. 20). CRDs contain topologically distinct types of modules, called an A-module and a B-module (see also FIG. 20). A-modules are C-shaped structures, and B-modules are S-shaped structures. A typical CRD is usually composed of A1-B2-modules or A2-B1-modules (or, less frequently, a different pair of modules, like A1-B1) with 6 conserved cysteine residues, wherein the numeral denotes the number of disulphide bridges within each module (see also FIG. 20). As shown in FIG. 20, 5 different human CD134 constructs were generated and expressed: (1) full-length human CD134 construct, which starts with N-terminal CRD1 (i.e., CRD1 A1-B2-module covers amino acids 29-65), and therefore denoted as 'CRD1', and comprised amino acids 1-277 (see SEQ ID NO. 1), (2) 'CRD2' construct, which starts with N-terminal CRD2 (i.e., CRD2 A1-B2-module covers amino acids 66-107), and comprised amino acids 66-277 linked to signal peptide amino acids 1-28 (see SEQ ID NO. 30), (3) 'CRD3' construct, which starts with N-terminal CRD3 (i.e., CRD3 A1-B1-module covers amino acids 108-146 (according to Compaan et al. Structure 2006; 14: 1321-1330) or truncated CRD3 A1-module covers amino acids 108-126 (according to Latza et al. Eur J Immunol 1994; 24: 677-683)), and comprised amino acids 108-277 linked to signal peptide amino acids 1-28 (see SEQ ID NO. 31), (4) 'CRD4' construct, which consists of N-terminal CRD4 or CRD3 subdomain B1-module/truncated CRD4 A1-module (i.e., CRD4 A1-B1-module covers amino acids 127-167 (Latza et al. Eur J Immunol 1994; 24: 677-683) or a combination (not shown in FIG. 20) of CRD3 subdomain B1-module with truncated CRD4 A1-module covers amino acids 127-146 with amino acids 147-167, respectively (Compaan et al. Structure 2006; 14: 1321-1330)), and comprised amino acids 127-277 linked to signal peptide amino acids 1-28 (see SEQ ID NO. 32), and (5) 'truncated (tc) CRD4' construct, which consists of with N-terminal truncated CRD4 or CRD4 subdomain B1-module (i.e., truncated CRD4 A1-module covers amino acids 147-167 (Compaan et al. Structure 2006; 14: 1321-1330) or CRD4 subdomain B1-module (not shown in FIG. 20; Latza et al. Eur J Immunol 1994; 24: 677-683) covers amino acids 147-167), and comprised amino acids 147-277 linked to signal peptide amino acids 1-28 (see SEQ ID NO. 33). By assembly PCR using Accuprime™ Pfx DNA Polymerase (Invitrogen), these 5 human CD134 constructs were generated using primers shown in the following table:

| Primer No.* | Sequence | SEQ ID No. | Direction | Gene |
|---|---|---|---|---|
| 362 | CTCGGATCCGCCACCATGTGCGTG | 51 | sense | CD134 leader |
| 363 | AGAATTCTTATTAGATCTTGGCCA | 55 | antisense | CD134 end |
| 364 | ACTGTCACTGGACCCTGCGGTCCC | 52 | sense | CRD2 |

-continued

| Primer No.* | Sequence | SEQ ID No. | Direction | Gene |
|---|---|---|---|---|
| 365 | GGGACCGCAGGGTCCAGTGACAGT | 53 | antisense | CRD2 |
| 366 | ACTGTCACTGGAAGGTGCAGGGCT | 54 | sense | CRD3 |
| 367 | AGCCCTGCACCTTCCAGTGACAGT | 56 | antisense | CRD3 |
| 368 | ACTGTCACTGGACCCTGCCCCCCT | 57 | sense | CRD4 |
| 369 | AGGGGGGCAGGGTCCAGTGACAGT | 58 | antisense | CRD4 |
| 370 | ACTGTCACTGGATGCACCCTGGCT | 59 | sense | CRD4 truncated |
| 371 | AGCCAGGGTGCATCCAGTGACAGT | 60 | antisense | CRD4 truncated |

*Primer No. according to Bioceros internal coding system

Briefly, cDNA encoding amino acids 1-28 of signal peptide and cDNA encoding amino acids 66-277 of human CD134 were amplified using respectively primer pair 362/365 and 364/363 in a PCR reaction with full-length human CD134 as a template. Subsequently, 'CRD2' construct was generated by using these two PCR products in an assembly PCR using primer pair 362/363. The cDNA encoding 'CRD2' construct was subcloned into a pcDNA3.1-derived expression plasmid using suitable restriction sites. Similarly, 'CRD3' construct (amino acids 1-28 of signal peptide linked to amino acids 108-277 of human CD134), 'CRD4' construct (amino acids 1-28 of signal peptide linked to amino acid 127-277), and 'truncated CRD4' construct (amino acids 1-28 of signal peptide linked to amino acid 147-277) were generated and subcloned in pcDNA3.1-derived expression plasmids using the corresponding primers shown in above-mentioned table. Furthermore, full-length human CD134 (SEQ ID NO. 1) was also re-cloned in a pcDNA3.1-derived expression plasmid.

Using the FreeStyle™ 293 Expression System (Invitrogen), FreeStyle™ 293-F cells (Invitrogen) were transiently transfected with the 5 generated variants of human CD134. After 48-72 h, surface human CD134 expression on transfected cells was analyzed by FACS analysis. To this end, transfected cells were harvested and put at $1-2 \times 10^6$ cells/mL in ice-chilled PBS/BSA/NaN$_3$. Cells were incubated with 20.0 µg/mL mouse anti-human CD134 monoclonal antibodies clones 12H3 and 20E5 for 30 minutes at 4° C. In parallel, 20.0 µg/mL mouse IgG1κ isotype control antibody (BD Biosciences) was used as a negative control. After extensive washing in PBS/BSA/NaN$_3$, cells were subsequently incubated with 1:200 diluted PE-conjugated goat anti-mouse IgG (Fcγ specific) antibodies (Jackson ImmunoResearch) for 30 minutes at 4° C. After extensive washing in PBS/BSA/NaN$_3$, cells were fixed in 2% formaldehyde in PBS/BSA/NaN$_3$ for 30 minutes at 4° C. Binding of antibodies was measured using flow cytometry (FACSCalibur; BD Biosciences).

Figure 21:
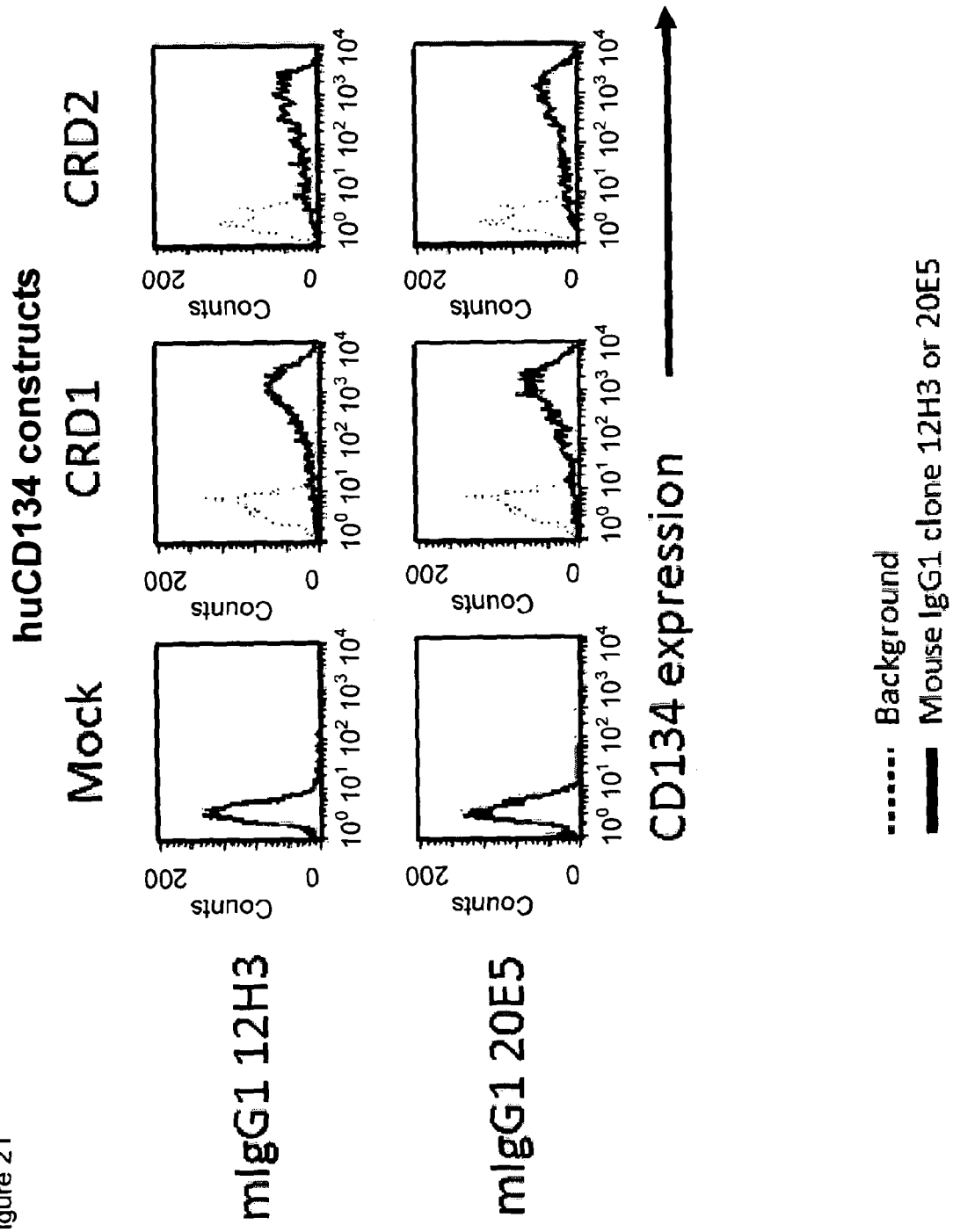
FIG. 21. Binding of mouse anti-human CD134 antibodies clones 12H3 and 20E5 on 293-F cell line transiently transfected with full-length human CD134 construct (denoted 'CRD1') or with various truncated human CD134 constructs (denoted 'CRD2', 'CRD3', 'CRD4', and 'truncated (tc) CRD4').
Figure 21:
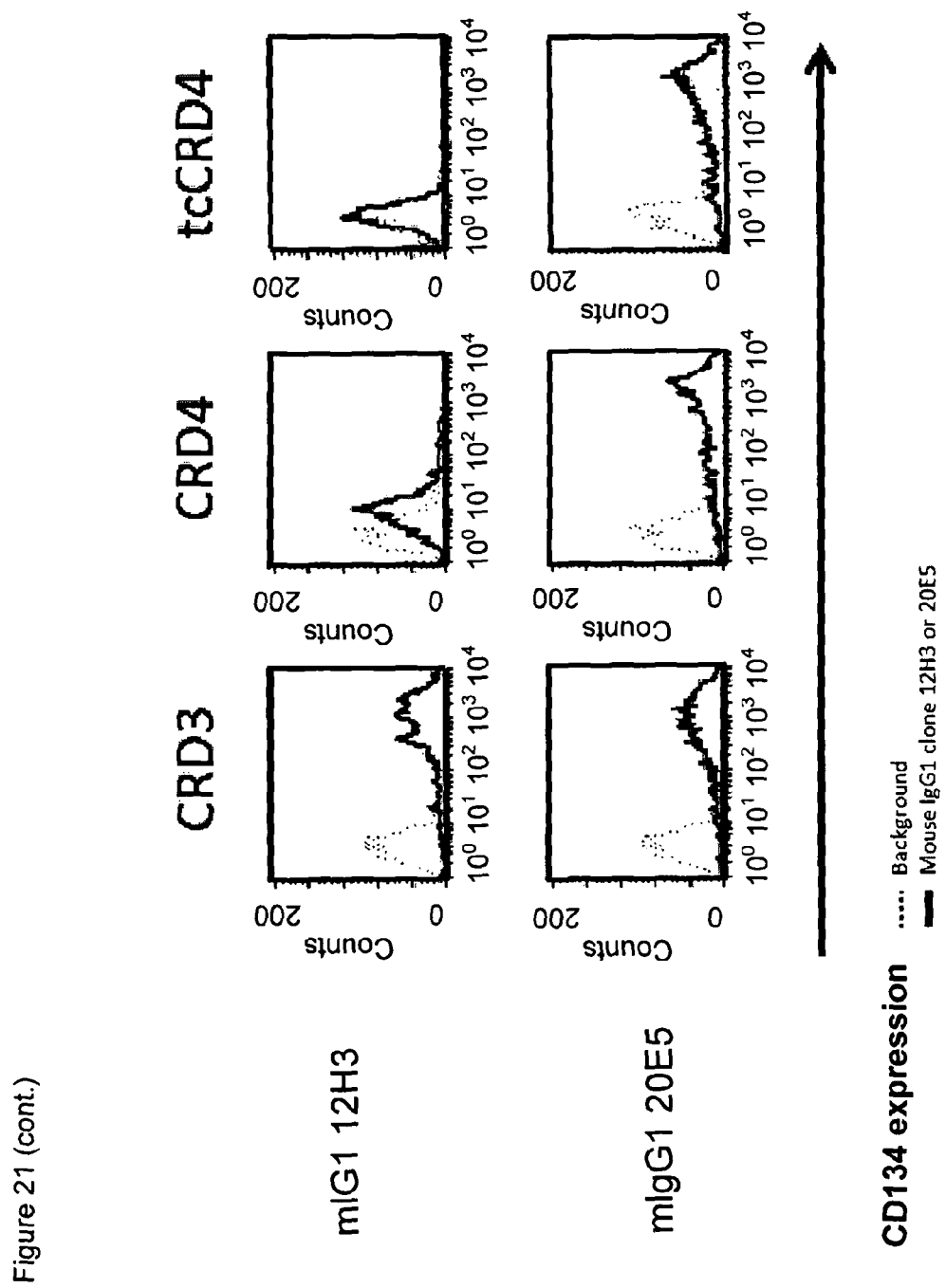

As shown in FIG. 21, both mouse anti-human CD134 antibodies clones 12H3 and 20E5 recognized full-length (denoted as 'CRD1' construct) human CD134 on transfected 293-F cells, whereas both mouse anti-human CD134 antibodies clones 12H3 and 20E5 showed no binding on mock-transfected 293-F cells. Moreover, mouse anti-human CD134 antibodies clones 12H3 and 20E5 recognized truncated human CD134 variants that lacked CRD1 and CRD1-CRD2 (denoted as 'CRD2' construct and 'CRD3' construct, respectively) on transfected 293-F cells. In contrast, binding of mouse anti-human CD134 antibody clone 12H3 against truncated human CD134 variant that lacked CRD1-CRD2-truncated CRD3 A1-module (denoted as 'CRD4' construct) was very weak, and binding of mouse anti-human CD134 antibody clone 12H3 against truncated human CD134 variant that lacked CRD1-CRD2-truncated CRD3 A1-module-CRD4 subdomain A1-module (according to definition of Latza et al. Eur J Immunol 1994; 24: 677-683) or alternatively CRD1-CRD2-CRD3 A1-B1-module (according to definition of Compaan et al. Structure 2006; 14: 1321-1330; denoted as 'tcCRD4' construct) was completely absent, whereas mouse anti-human CD134 antibody clone 20E5 showed a strong binding against truncated human CD134 variant that lacked CRD1-CRD2-truncated CRD3 A1-module (denoted as 'CRD4' construct) and against truncated human CD134 variant that lacked CRD1-CRD2-truncated CRD3 A1-module-CRD4 subdomain A1-module (according to definition of Latza et al. Eur J Immunol 1994; 24: 677-683) or alternatively CRD1-CRD2-CRD3 A1-B1-module (according to definition of Compaan et al. Structure 2006; 14: 1321-1330; denoted as 'tcCRD4' construct).

These results demonstrated that mouse anti-human CD134 antibodies clones 12H3 and 20E5 specifically recognized human CD134 (comparison of full-length human CD134 transfection vs mock transfection). Furthermore, these results demonstrated that mouse anti-human CD134 antibodies clones 12H3 and 20E5 seemed to recognize dissimilar human CD134 epitopes, which is evidenced by respective lack of binding (using clone 12H3) vs strong binding (using clone 20E5) with truncated human CD134 variant that lacked CRD1-CRD2-truncated CRD3 A1-module (denoted as 'CRD4' construct) and with truncated human CD134 variant that lacked CRD1-CRD2-truncated CRD3 A1-module-CRD4 subdomain A1-module (according to definition of Latza et al. Eur J Immunol 1994; 24: 677-683) or alternatively CRD1-CRD2-CRD3 A1-B1-module (according to definition of Compaan et al. Structure 2006; 14: 1321-1330; denoted as 'tcCRD4' construct). These results demonstrated that mouse anti-human CD134 antibody clone 12H3 did not seem to recognize a human CD134 epitope in CRD1 and CRD2, and mouse anti-human CD134 antibody clone 20E5 did not seem to recognize a human CD134 epitope in CRD1, CRD2, and truncated CRD3 A1-module-CRD4 subdomain A1-module (according to definition of Latza et al. Eur J Immunol 1994; 24: 677-683) or alternatively CRD1-CRD2-CRD3 A1-B1-module (according to definition of Compaan et al. Structure 2006; 14: 1321-1330). These results demonstrated that mouse anti-human CD134 antibody clone 12H3 seemed to recognize a linear or non-linear/conformational epitope in truncated CRD3 A1-module (according to definition of Latza et al. Eur J Immunol 1994; 24: 677-683) with amino acid sequence 108-126 (i.e., 19-meric peptide RCRAGTQPLDSYKPGVDCA; see SEQ ID NO. 34) on extracellular human CD134, or amino acid sequence 108-126 (i.e., 19-meric peptide RCRAGTQ-PLDSYKPGVDCA; see SEQ ID NO. 34) formed a crucial part for binding to a non-linear/conformational epitope in truncated CRD3 A1-module/CRD4 A1-B1-module (according to definition of Latza et al. Eur J Immunol 1994; 24: 677-683), and possibly in the hinge-like structure, with amino acid sequence 108-214 (see SEQ ID NO. 35) on extracellular human CD134. These results demonstrated that mouse anti-human CD134 antibody clone 20E5 seemed to recognize a linear or non-linear/conformational epitope in truncated CRD4 A1-module (according to definition of Compaan et al. Structure 2006; 14: 1321-1330), and possibly in the hinge-like structure, with amino acid sequence 147-214 (SEQ ID NO. 36) on extracellular human CD134.

Using a crystallography, Compaan et al. (Structure 2006; 14: 1321-1330) recently discovered critical involvement of CRD1, CRD2 (especially A1 loop and immediately following residues), and CRD3 (primarily A1 loop) on human CD134 during OX40Ligand (CD252)/CD134 (=OX40) interaction. This discovery is in good agreement with our findings that (1, see above) mouse anti-human CD134 antibody clone 20E5 did not seem to recognize a human CD134 epitope in CRD1, CRD2, and truncated CRD3 A1-module-CRD4 subdomain A1-module (according to definition of Latza et al. Eur J Immunol 1994; 24: 677-683) or alternatively CRD1-CRD2-CRD3 A1-B1-module (according to definition of Compaan et al. Structure 2006; 14: 1321-1330) on extracellular human CD134, and (2, see above) mouse anti-human CD134 antibody clone 20E5 bound simultaneously with human OX40L on PHA-stimulated human CD134 expressing T lymphocytes. This suggested that mouse anti-human CD134 antibody clone 20E5 recognized an epitope on human CD134, which was not critically involved in interaction of human CD134 with human OX40L. Moreover, our findings that (1, see above) mouse anti-human CD134 antibody clone 12H3 seemed to recognize a linear or non-linear/conformational epitope in truncated CRD3 A1-module (according to definition of Latza et al. Eur J Immunol 1994; 24: 677-683) with amino acid sequence 108-126 (i.e., 19-meric peptide RCRAGTQ-PLDSYKPGVDCA; see SEQ ID NO. 34) on extracellular human CD134, or amino acid sequence 108-126 (i.e., 19-meric peptide RCRAGTQPLDSYKPGVDCA; see SEQ ID NO. 34) formed a crucial part for binding to a non-linear/conformational epitope in truncated CRD3 A1-module/CRD4 A1-B1-module (according to definition of Latza et al. Eur J Immunol 1994; 24: 677-683), and possibly in the hinge-like structure, with amino acid sequence 108-214 (see SEQ ID NO. 35) on extracellular human CD134, and (2, see above) mouse anti-human CD134 antibody clone 12H3 bound simultaneously with human OX40L on PHA-stimulated human CD134 expressing T lymphocytes, substantiated the idea that the epitope (as described above) on human CD134 that was recognized by mouse anti-human CD134 antibody clone 12H3 was not critically involved in interaction of human CD134 with human OX40L.

(c). Epitope Mapping (1) of Mouse Anti-Human CD134 Monoclonal Antibody Clone 12H3 Using Human CD134-Derived Peptide ELISA In order to further analyze the fine specificity of mouse anti-human CD134 monoclonal antibody clone 12H3, the location of the epitope recognized by mouse anti-human CD134 monoclonal antibody clone 12H3 was determined by epitope mapping. The ability of mouse anti-human CD134 monoclonal antibody clone 12H3 to bind with a human CD134-derived peptide, which corresponded to amino acid sequence of truncated CRD3 A1-module-CRD4 subdomain A1-module (according to definition of Latza et al. Eur J Immunol 1994; 24: 677-683), was determined by ELISA.

Ninety six-wells flat-bottom ELISA plates (Corning) were coated with 10 ng/well human CD134-derived peptide (synthesized by Pepscan Presto, Lelystad, The Netherlands), which corresponded to amino acid sequence of truncated CRD3 A1-module-CRD4 subdomain A1-module (see SEQ ID NO. 38) or with 10 ng/well human fibronectin-derived control peptide (synthesized by Pepscan Presto, Lelystad, The Netherlands), which corresponded to amino acid sequence of extra type III structural domain (see SEQ ID NO. 37) in PBS o/n at 4° C. After extensive washing in PBS/0.05% Tween 20, plates were blocked in PBS/0.05% Tween 20/1% BSA fraction V (Roche) for 1 hour at RT. Subsequently, plates were incubated with 0, 0.00005-50.0 (10-fold dilution steps in block buffer) µg/mL mouse anti-human CD134 monoclonal antibody clone 12H3 or mouse IgG$_1$κ isotype control antibody (BD Biosciences) for 1 hour at RT. After extensive washing in PBS/0.05% Tween 20, binding of antibodies was determined with 1:5000 diluted horseradish peroxidase-conjugated goat anti-mouse IgG Fcγ-specific antibodies (Jackson ImmunoResearch) for 1 hour at RT, followed by a ready-to-use solution of TMB substrate (Invitrogen) for colorimetric detection. After adding 1 M H$_2$SO$_4$, optical densities was measured at a wavelength of 450 nm (reference wavelength of 655 nm) using a microplate reader (BioRad).

Figure 23:
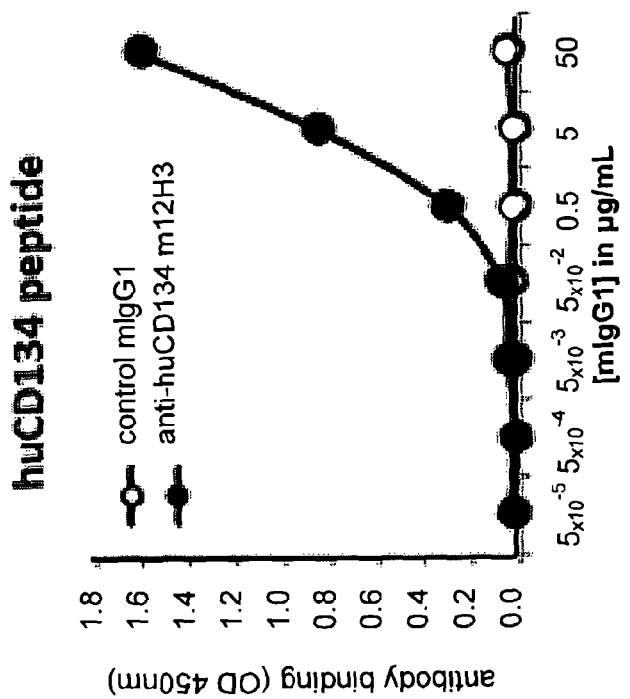
FIG. 23. Binding of mouse anti-human CD134 antibody clone 12H3 (A) and chimeric human IgG4κ anti-human CD134 antibody clone 12H3 (B) with human CD134-derived peptide, which corresponds to amino acid sequence of truncated CRD3 A1-module-CRD4 subdomain A1-module (according to definition of Latza et al. Eur J Immunol 1994; 24: 677-683).
Figure 23:
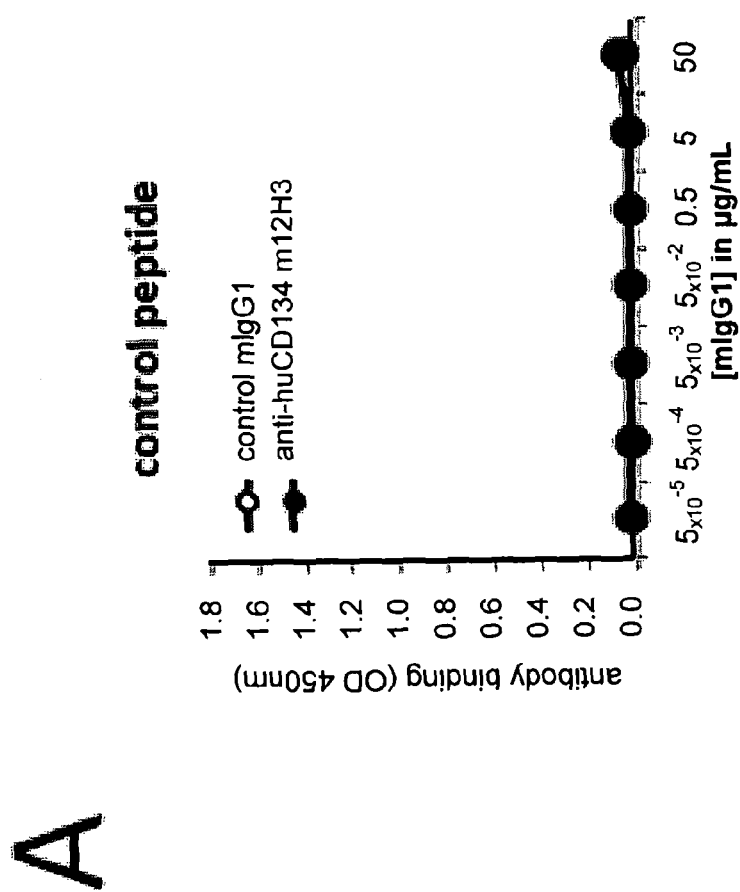
Figure 23:
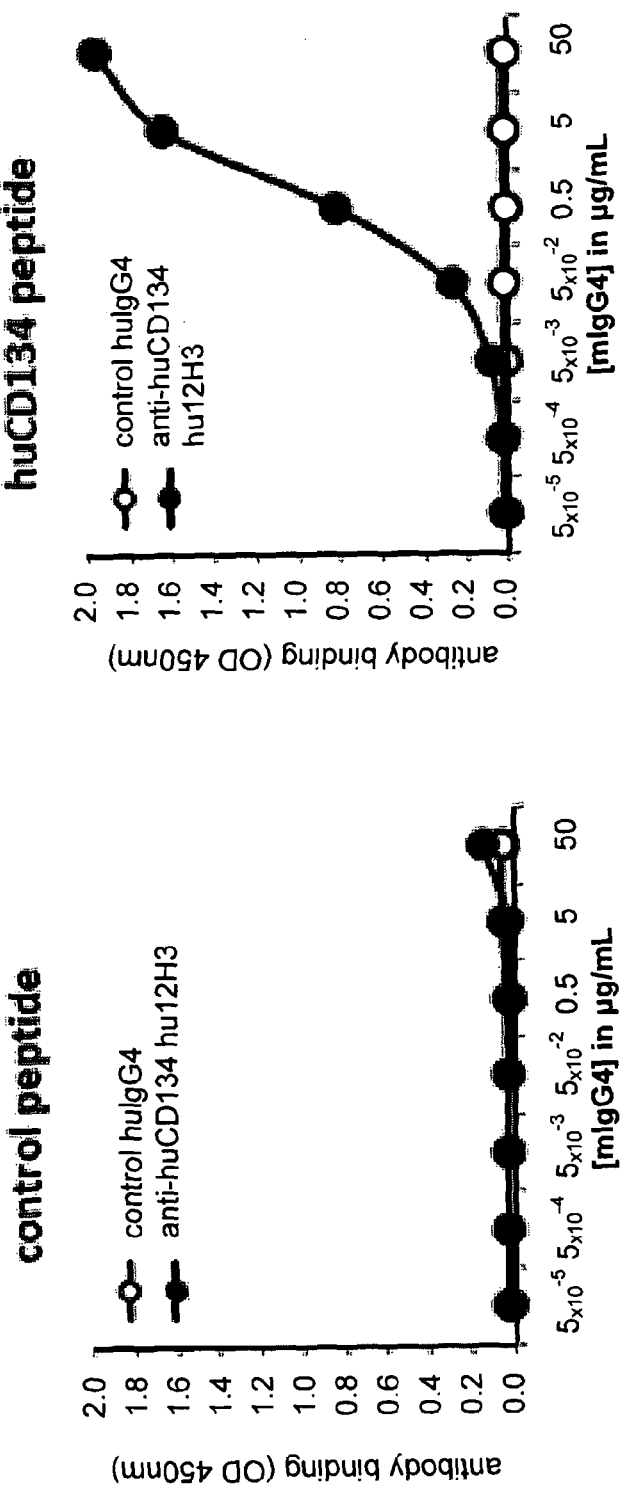

As shown in FIG. 23-A (n=1), mouse anti-human CD134 monoclonal antibody clone 12H3 dose-dependently and specifically bound human CD134-derived peptide, whereas mouse IgG$_1$κ isotype control antibody demonstrated no binding to human CD134-derived peptide. Both mouse anti-human CD134 monoclonal antibody clone 12H3 and IgG$_1$κ isotype control antibody demonstrated no binding to human fibronectin-derived control peptide.

These results demonstrated that mouse anti-human CD134 antibody clone 12H3 specifically recognized an epitope on human CD134 (comparison of human CD134-derived peptide vs. human fibronectin-derived control peptide). Furthermore, these results demonstrated that mouse anti-human CD134 antibody clone 12H3 seemed to recognize a linear or non-linear/conformational epitope in truncated CRD3 A1-module-CRD4 subdomain A1-module (according to definition of Latza et al. Eur J Immunol 1994; 24: 677-683) with amino acid sequence 108-146 (i.e., 39-meric peptide RCRAGTQPLDSYKPGVDCAPCPPGHFSPGDN-QACKPWTN; see SEQ ID NO. 38) on extracellular human CD134.

(d) Epitope Mapping (2) of Mouse Anti-Human CD134 Monoclonal Antibodies Clones 12H3 and 20E5 Using CLIPS Epitope Mapping Technology by Pepscan CLIPS Epitope Mapping Technology by Pepscan (Lelystad, The Netherlands) may be used to determine the epitopes recognized by mouse anti-human CD134 antibodies clones 12H3 and 20E5. This CLIPS technology enables the determination of linear, conformational, discontinuous, and complex epitopes involving dimeric or multimeric protein complexes. For this purpose, the linear amino acid sequence of human CD134=OX40 (SEQ ID NO. 1) is used as the target protein.

Example 9

Characterization of Human CD134 Domains and Epitopes Recognized by Chimeric Human IgG4/Kappa and/or IgG1/Kappa Anti-Human CD134 Monoclonal Antibodies Clones 12H3 and 20E5

(a). Binding Chimeric Human IgG4κ and/or IgG1κ Anti-Human CD134 Monoclonal Antibodies Clones 12H3 and 20E5 with Full-Length Human CD134 Construct and Various Truncated Human CD134 Constructs Expressed on 293-F Cell Line (Domain Mapping)

In order to analyze the fine specificity of chimeric human IgG4κ and/or IgG1κ anti-human CD134 monoclonal antibodies clones 12H3 and 20E5, the location of epitope(s) recognized by chimeric human IgG4κ and/or IgG1κ anti-human CD134 monoclonal antibodies clones 12H3 and 20E5 was determined by domain mapping. The ability of chimeric human IgG4κ and/or IgG1κ anti-human CD134 monoclonal antibodies clones 12H3 and 20E5 to bind to truncated human CD134 constructs (see Example 8 (b) above), expressed on the surface of (HEK-derived) 297-F cells, was determined by FACS analysis.

Using the FreeStyle™ 293 Expression System (Invitrogen), FreeStyle™ 293-F cells (Invitrogen) were transiently transfected with the 5 generated variants of human CD134 (see above). After 48-72 h, surface human CD134 expression on transfected cells was analyzed by FACS analysis. To this end, transfected cells were harvested and put at $1-2 \times 10^6$ cells/mL in ice-chilled PBS/BSA/NaN$_3$. Cells were incubated with or without 20.0 µg/mL chimeric human IgG4κ and/or IgG1κ anti-human CD134 monoclonal antibodies clones 12H3 and 20E5 for 30 minutes at 4° C. After extensive washing in PBS/BSA/NaN$_3$, cells were subsequently incubated with 1:200 diluted PE-conjugated goat anti-human IgG (Fcγ specific) antibodies (Jackson ImmunoResearch) for 30 minutes at 4° C. After extensive washing in PBS/BSA/NaN$_3$, cells were fixed in 2% formaldehyde in PBS/BSA/NaN$_3$ for 30 minutes at 4° C. Binding of antibodies was measured using flow cytometry (FACSCalibur; BD Biosciences).

Figure 22:
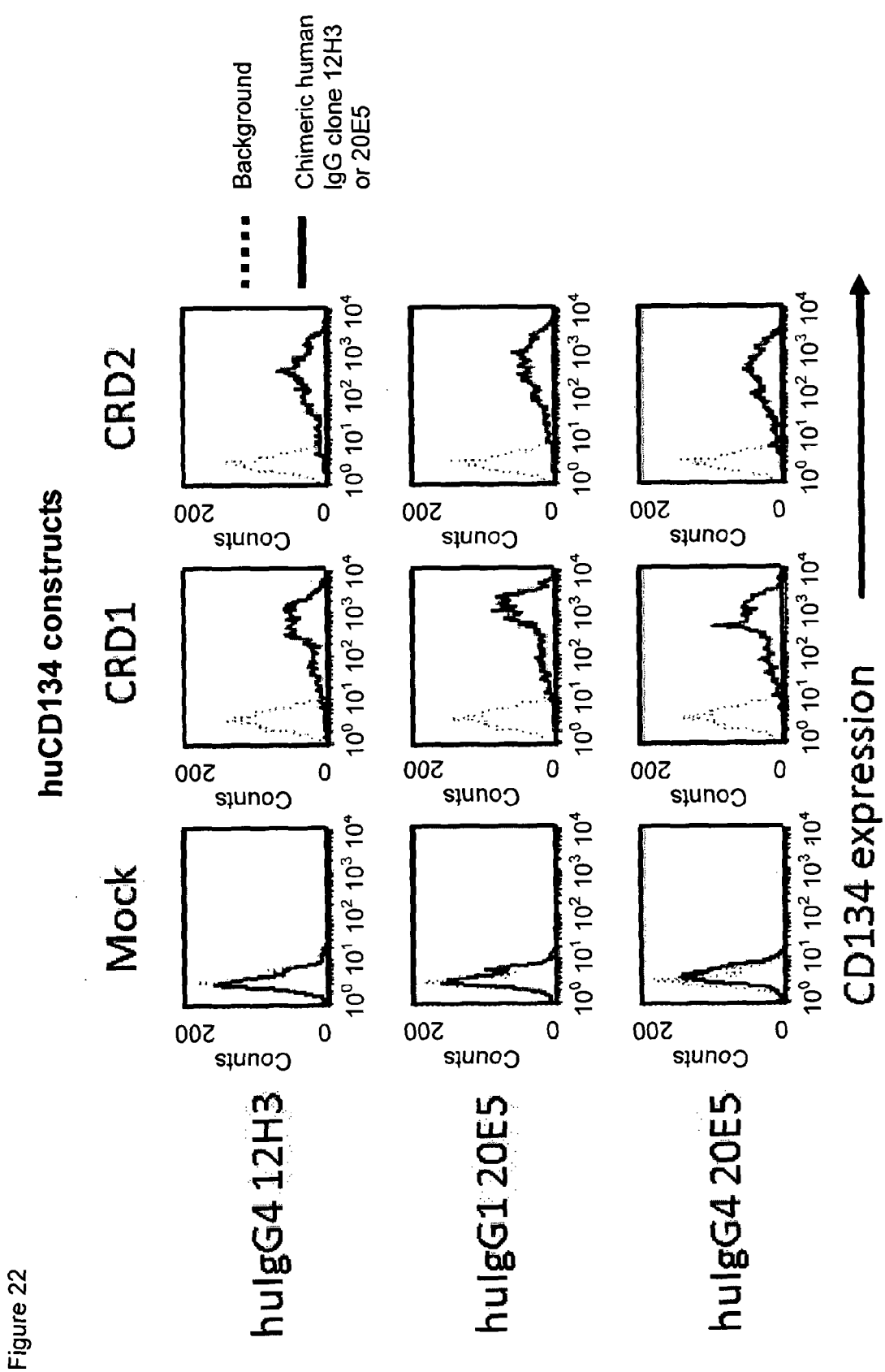
FIG. 22. Binding of chimeric human IgG4κ and/or IgG1κ anti-human CD134 antibodies clones 12H3 and 20E5 on 293-F cell line transiently transfected with full-length human CD134 construct (denoted 'CRD1') or with various truncated human CD134 constructs (denoted 'CRD2', 'CRD3', 'CRD4', and 'truncated (tc) CRD4').
Figure 22:
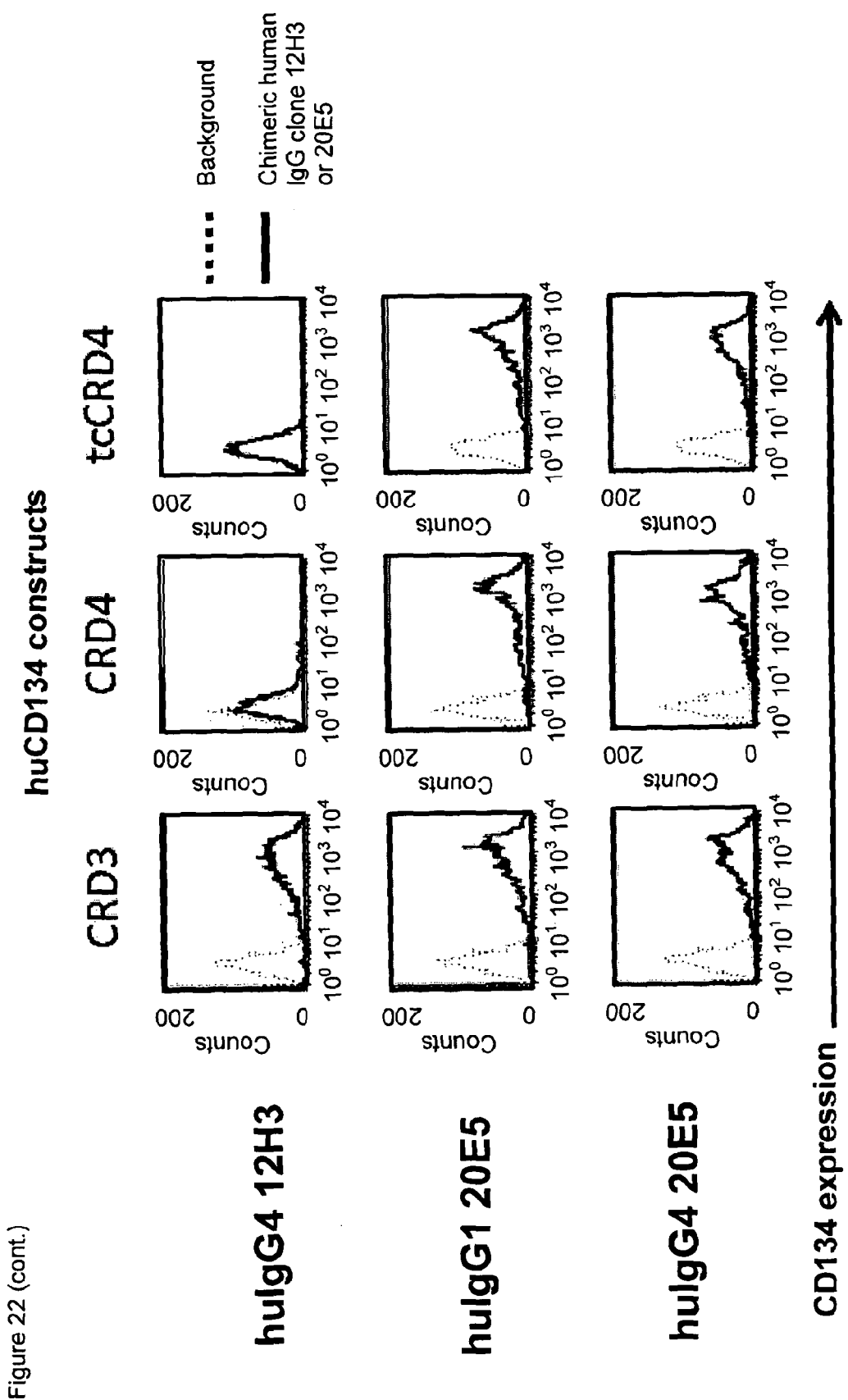

As shown in FIG. 22, both chimeric human IgG4κ and IgG1κ anti-human CD134 monoclonal antibody clone 12H3, and chimeric human IgG4κ anti-human CD134 monoclonal antibody clone 20E5 demonstrated binding characteristics against various truncated human CD134 constructs on transfected cells, which were identical to binding characteristics of their corresponding parental mouse anti-human CD134 antibodies clones 12H3 and 20E5 counterparts (see Example 8 (b) above; for comparison, see FIG. 22 vs FIG. 21).

(b). Epitope Mapping of Chimeric Human IgG4κ Anti-Human CD134 Monoclonal Antibody Clone 12H3 Using Human CD134-Derived Peptide ELISA In order to further analyze the fine specificity of chimeric human IgG4κ anti-human CD134 monoclonal antibody clone 12H3, the location of the epitope recognized by chimeric human IgG4κ anti-human CD134 monoclonal antibody clone 12H3 was determined by epitope mapping. The ability of chimeric human IgG4κ anti-human CD134 monoclonal antibody clone 12H3 to bind with a human CD134-derived peptide, which corresponded to amino acid sequence of truncated CRD3 A1-module-CRD4 subdomain A1-module (according to definition of Latza et al. Eur J Immunol 1994; 24: 677-683), was determined by ELISA.

Ninety six-wells flat-bottom ELISA plates (Corning) were coated with 10 ng/well human CD134-derived peptide (synthesized by Pepscan Presto, Lelystad, The Netherlands), which corresponded to amino acid sequence of truncated CRD3 A1-module-CRD4 subdomain A1-module (see SEQ ID NO. 38) or with 10 ng/well human fibronectin-derived control peptide (synthesized by Pepscan Presto, Lelystad, The Netherlands), which corresponded to amino acid sequence of extra type III structural domain (see SEQ ID NO. 37) in PBS o/n at 4° C. After extensive washing in PBS/0.05% Tween 20, plates were blocked in PBS/0.05% Tween 20/1% BSA fraction V (Roche) for 1 hour at RT. Subsequently, plates were incubated with 0, 0.00005-50.0 (10-fold dilution steps in block buffer) µg/mL chimeric human IgG4κ anti-human CD134 monoclonal antibody clone 12H3 or control human IgG4κ anti-human CD40 antibody (Biocult) for 1 hour at RT. After extensive washing in PBS/0.05% Tween 20, binding of antibodies was determined with 1:5000 diluted horseradish peroxidase-conjugated goat anti-human IgG Fcγ-specific antibodies (Jackson ImmunoResearch) for 1 hour at RT, followed by a ready-to-use solution of TMB substrate (Invitrogen) for colorimetric detection. After adding 1 M $H_2SO_4$, optical densities was measured at a wavelength of 450 nm (reference wavelength of 655 nm) using a microplate reader (BioRad).

As shown in FIG. 23-B (n=1), chimeric human IgG4κ anti-human CD134 monoclonal antibody clone 12H3 dose-dependently and specifically bound human CD134-derived peptide, whereas control human IgG4κ anti-human CD40 antibody demonstrated no binding to human CD134-derived peptide. Both chimeric human IgG4κ anti-human CD134 monoclonal antibody clone 12H3 and control human IgG4κ anti-human CD40 antibody demonstrated no binding to human fibronectin-derived control peptide.

These results demonstrated that chimeric human IgG4κ anti-human CD134 monoclonal antibody clone 12H3 specifically recognized an epitope on human CD134 (comparison of human CD134-derived peptide vs human fibronectin-derived control peptide). Furthermore, these results demonstrated that chimeric human IgG4κ anti-human CD134 monoclonal antibody clone 12H3 seemed to recognize a linear or non-linear/conformational epitope in truncated CRD3 A1-module-CRD4 subdomain A1-module (according to definition of Latza et al. Eur J Immunol 1994; 24: 677-683) with amino acid sequence 108-146 (i.e., 39-meric peptide RCRAGTQPLDSYKPGVDCAPCPPGHFSPGDNQACKPWTN; see SEQ ID NO. 38) on extracellular human CD134.

The attached sequence listing forms part of this specification.

In SEQ ID NO: 1, which is the amino acid sequence human CD134 (GenBank ref CAB96543.1; aa 1-277) a signal peptide is at amino acids (aa) 1-28) and a transmembrane region at aa 215-235.

SEQ ID NO: 61, which forms the 11 N-terminal amino acids of SEQ ID NO: 5, is also of interest. This the 20E5 light chain equivalent of SEQ ID NO: 3, which is the 11 N-terminal amino acids of the 20E5 heavy chain.

SEQ ID NO. 37 (TYSSPEDGIHELFPAPDGEEDTAELQGGC), amino acid sequence from human fibronectin-derived peptide, corresponds to amino acid sequence of extra type III structural domain (ED1; Peters et al. Am Rev Resp Dis 1988; 138: 167-71).

The invention claimed is:

1. An antibody that binds to human CD134, or an antigen-binding fragment thereof, wherein the antibody or antigen-binding fragment does not prevent human CD134 (OX40) receptor binding to OX40 ligand (OX40L), and wherein the antibody comprises a heavy chain variable region comprising:
   (a) a heavy chain CDR1 comprising the amino acid sequence of SEQ ID NO:6;
   (b) a heavy chain CDR2 comprising the amino acid sequence of SEQ ID NO:7; and
   (c) a heavy chain CDR3 comprising the amino acid sequence of SEQ ID NO:8; and
wherein the antibody comprises a light chain variable region comprising:
   (a) a light chain CDR1 comprising the amino acid sequence of SEQ ID NO: 9
   (b) a light chain CDR2 comprising the amino acid sequence of SEQ ID NO: 10; and
   (c) a light chain CDR3 comprising the amino acid sequence of SEQ ID NO: 11.

2. The antibody or antigen-binding fragment of claim 1 wherein at or above the saturation concentration of the antibody or antigen-binding fragment the effect on binding of OX40L to CD134 is reduced by not more than 50% on human CD134 expressing T-cells.

3. The antibody or antigen-binding fragment of claim 1 wherein at a concentration of 70 nM of the antibody or antigen-binding fragment, the effect on binding of OX40L to CD134 is reduced by not more than 70% on human CD134 expressing T-cells.

4. The antibody or antigen-binding fragment of claim 1, wherein the antibody comprises:
   (a) a heavy chain variable region comprising the amino acid sequence of SEQ ID NO:4; and
   (b) a light chain variable region comprising the amino acid sequence of SEQ ID NO:5.

5. The antibody or antigen-binding fragment of claim 1, wherein the antibody is a human antibody.

6. The antibody or antigen-binding fragment of claim 1, wherein the antibody is a chimeric or humanized antibody.

7. The antibody or antigen-binding fragment of claim 1, wherein the antibody is an IgA, IgD, IgE, IgG or IgM antibody.

8. The antibody or antigen-binding fragment of claim 1, wherein the antibody is an IgG1, IgG2, IgG3 or IgG4 antibody.

9. The antigen-binding fragment of claim 1 wherein the antigen-binding fragment is an scFv.

10. The antibody or antigen-binding fragment of claim 1 wherein the antibody or antigen-binding fragment is a recombinant antibody or antigen-binding fragment.

11. The antibody or antigen-binding fragment of claim 1 wherein the antibody or antigen-binding fragment is a monoclonal antibody or antigen-binding fragment.

12. The antibody or antigen-binding fragment of claim 1, wherein said antigen-binding fragment is a Fv fragment or a Fab-like fragment.

13. The antibody or antigen-binding fragment of claim 1 which is an agonist of CD134.

14. A pharmaceutical composition comprising an antibody or antigen-binding fragment of claim 1 together with one or more pharmaceutically acceptable diluents or excipients.

* * * * *

SEQUENCE LISTING

<160> NUMBER OF SEQ ID NOS: 63

<210> SEQ ID NO 1
<211> LENGTH: 277
<212> TYPE: PRT
<213> ORGANISM: Homo sapiens
<220> FEATURE:
<221> NAME/KEY: SIGNAL
<222> LOCATION: (1)..(28)
<220> FEATURE:
<221> NAME/KEY: TRANSMEM
<222> LOCATION: (215)..(235)

<400> SEQUENCE: 1

```
Met Cys Val Gly Ala Arg Arg Leu Gly Arg Gly Pro Cys Ala Ala Leu
1               5                   10                  15

Leu Leu Leu Gly Leu Gly Leu Ser Thr Val Thr Gly Leu His Cys Val
            20                  25                  30

Gly Asp Thr Tyr Pro Ser Asn Asp Arg Cys Cys His Glu Cys Arg Pro
        35                  40                  45

Gly Asn Gly Met Val Ser Arg Cys Ser Arg Ser Gln Asn Thr Val Cys
    50                  55                  60

Arg Pro Cys Gly Pro Gly Phe Tyr Asn Asp Val Val Ser Ser Lys Pro
65                  70                  75                  80

Cys Lys Pro Cys Thr Trp Cys Asn Leu Arg Ser Gly Ser Glu Arg Lys
                85                  90                  95

Gln Leu Cys Thr Ala Thr Gln Asp Thr Val Cys Arg Cys Arg Ala Gly
            100                 105                 110

Thr Gln Pro Leu Asp Ser Tyr Lys Pro Gly Val Asp Cys Ala Pro Cys
        115                 120                 125

Pro Pro Gly His Phe Ser Pro Gly Asp Asn Gln Ala Cys Lys Pro Trp
    130                 135                 140

Thr Asn Cys Thr Leu Ala Gly Lys His Thr Leu Gln Pro Ala Ser Asn
145                 150                 155                 160

Ser Ser Asp Ala Ile Cys Glu Asp Arg Asp Pro Pro Ala Thr Gln Pro
                165                 170                 175

Gln Glu Thr Gln Gly Pro Pro Ala Arg Pro Ile Thr Val Gln Pro Thr
            180                 185                 190

Glu Ala Trp Pro Arg Thr Ser Gln Gly Pro Ser Thr Arg Pro Val Glu
        195                 200                 205

Val Pro Gly Gly Arg Ala Val Ala Ala Ile Leu Gly Leu Gly Leu Val
    210                 215                 220

Leu Gly Leu Leu Gly Pro Leu Ala Ile Leu Leu Ala Leu Tyr Leu Leu
225                 230                 235                 240

Arg Arg Asp Gln Arg Leu Pro Pro Asp Ala His Lys Pro Pro Gly Gly
                245                 250                 255

Gly Ser Phe Arg Thr Pro Ile Gln Glu Glu Gln Ala Asp Ala His Ser
            260                 265                 270

Thr Leu Ala Lys Ile
        275
```

<210> SEQ ID NO 2
<211> LENGTH: 834
<212> TYPE: DNA
<213> ORGANISM: Artificial Sequence
<220> FEATURE:
<223> OTHER INFORMATION: Description of Artificial Sequence: Synthetic
      Sf9 insect cell-optimized cDNA sequence for human CD134

<400> SEQUENCE: 2

```
atgtgcgtgg gcgctcgtcg tctgggtcgt ggtccctgcg ctgctctgct gctgctgggt      60
ctgggcctgt ccactgtcac tggactccac tgcgtgggcg acacctaccc ctccaacgac     120
cgttgctgcc acgaatgcag gcctggcaac ggcatggtgt cccgttgctc ccgttcccag     180
aacaccgtgt gccgtccctg cggtcccggt ttctacaacg acgtggtgtc ctccaagccc     240
tgcaagcctt gcacttggtg taacctccgc tccggttccg agcgcaagca gctgtgcacc     300
gctacccagg acactgtctg taggtgcagg gctggcaccc agccctggac tcctacaag      360
cccggtgtcg actgcgctcc ctgccccct ggtcacttct ctcccggcga caaccaggct      420
tgcaaaccat ggaccaactg caccctggct ggcaagcaca ccctgcagcc cgcttccaac     480
tcctccgacg ctatctgcga ggaccgtgac cccctgcta tcaacctca ggagactcag       540
ggtcccccg ctcgtcccat caccgtgcag cccaccgagg cttggccccg tacctcccaa      600
ggacctagca ctaggcctgt ggaggtgccc ggtggtcgtg ctgtggctgc tatcctgggc     660
ctgggtctgg tgctgggcct gctgggtccc ctggctatcc tgctggctct gtacctcctg    720
cgtcgtgacc agcgtctgcc ccccgacgct cacaagcccc tggtggtgg ttccttccgt      780
accccatcc aggaggagca ggctgacgct cactccaccc tggccaagat ctaa            834
```

<210> SEQ ID NO 3
<211> LENGTH: 11
<212> TYPE: PRT
<213> ORGANISM: Artificial Sequence
<220> FEATURE:
<223> OTHER INFORMATION: Description of Artificial Sequence: Synthetic
      N-terminus amino acid sequence of clone 20E5 heavy chain

<400> SEQUENCE: 3

```
Glu Val Gln Leu Gln Gln Ser Gly Pro Glu Leu
1               5                   10
```

<210> SEQ ID NO 4
<211> LENGTH: 119
<212> TYPE: PRT
<213> ORGANISM: Artificial Sequence
<220> FEATURE:
<223> OTHER INFORMATION: Description of Artificial Sequence: Synthetic
      amino acid sequence of clone 20E5 heavy chain variable region

<400> SEQUENCE: 4

```
Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Val Met His Trp Val Lys Gln Lys Pro Gly Gln Gly Leu Glu Trp Ile
        35                  40                  45

Gly Tyr Ile Asn Pro Tyr Asn Asp Gly Thr Lys Tyr Asn Glu Lys Phe
    50                  55                  60

Lys Gly Lys Ala Thr Leu Thr Ser Asp Lys Ser Ser Thr Ala Tyr
65                  70                  75                  80

Met Glu Leu Ser Ser Leu Thr Ser Glu Asp Ser Ala Val Tyr Tyr Cys
                85                  90                  95

Ala Asn Tyr Tyr Gly Ser Ser Leu Ser Met Asp Tyr Trp Gly Gln Gly
            100                 105                 110

Thr Ser Val Thr Val Ser Ser
        115
```

<210> SEQ ID NO 5
<211> LENGTH: 108
<212> TYPE: PRT
<213> ORGANISM: Artificial Sequence
<220> FEATURE:
<223> OTHER INFORMATION: Description of Artificial Sequence: Synthetic
      amino acid sequence of clone 20E5 light chain variable region

<400> SEQUENCE: 5

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Trp
                85                  90                  95

Thr Phe Gly Gly Gly Thr Lys Leu Glu Ile Lys Arg
            100                 105

<210> SEQ ID NO 6
<211> LENGTH: 10
<212> TYPE: PRT
<213> ORGANISM: Artificial Sequence
<220> FEATURE:
<223> OTHER INFORMATION: Description of Artificial Sequence: Synthetic
      amino acid sequence of clone 20E5 heavy chain CDR1

<400> SEQUENCE: 6

Gly Tyr Thr Phe Thr Ser Tyr Val Met His
1               5                   10

<210> SEQ ID NO 7
<211> LENGTH: 17
<212> TYPE: PRT
<213> ORGANISM: Artificial Sequence
<220> FEATURE:
<223> OTHER INFORMATION: Description of Artificial Sequence: Synthetic
      amino acid sequence of clone 20E5 heavy chain CDR2

<400> SEQUENCE: 7

Tyr Ile Asn Pro Tyr Asn Asp Gly Thr Lys Tyr Asn Glu Lys Phe Lys
1               5                   10                  15

Gly

<210> SEQ ID NO 8
<211> LENGTH: 10
<212> TYPE: PRT
<213> ORGANISM: Artificial Sequence
<220> FEATURE:
<223> OTHER INFORMATION: Description of Artificial Sequence: Synthetic
      amino acid sequence of clone 20E5 heavy chain CDR3

<400> SEQUENCE: 8

Tyr Tyr Gly Ser Ser Leu Ser Met Asp Tyr
1               5                   10

<210> SEQ ID NO 9
<211> LENGTH: 11

```
<212> TYPE: PRT
<213> ORGANISM: Artificial Sequence
<220> FEATURE:
<223> OTHER INFORMATION: Description of Artificial Sequence: Synthetic
      amino acid sequence of clone 20E5 light chain CDR1

<400> SEQUENCE: 9

Arg Ala Ser Gln Asp Ile Ser Asn Tyr Leu Asn
1               5                   10

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: Synthetic
      amino acid sequence of clone 20E5 light chain CDR2

<400> SEQUENCE: 10

Tyr Thr Ser Arg Leu His Ser
1               5

<210> SEQ ID NO 11
<211> LENGTH: 9
<212> TYPE: PRT
<213> ORGANISM: Artificial Sequence
<220> FEATURE:
<223> OTHER INFORMATION: Description of Artificial Sequence: Synthetic
      amino acid sequence of clone 20E5 light chain CDR3

<400> SEQUENCE: 11

Gln Gln Gly Asn Thr Leu Pro Trp Thr
1               5

<210> SEQ ID NO 12
<211> LENGTH: 121
<212> TYPE: PRT
<213> ORGANISM: Artificial Sequence
<220> FEATURE:
<223> OTHER INFORMATION: Description of Artificial Sequence: Synthetic
      amino acid sequence of clone 12H3 heavy chain variable region

<400> SEQUENCE: 12

Glu Val Gln Leu Gln Gln Ser Gly Pro Glu Leu Val Lys Pro Gly Ala
1               5                   10                  15

Ser Val Lys Ile Ser Cys Lys Thr Ser Gly Tyr Thr Phe Lys Asp Tyr
            20                  25                  30

Thr Met His Trp Val Lys Gln Ser His Gly Lys Ser Leu Glu Trp Ile
        35                  40                  45

Gly Gly Ile Tyr Pro Asn Asn Gly Gly Ser Thr Tyr Asn Gln Asn Phe
    50                  55                  60

Lys Asp Lys Ala Thr Leu Thr Val Asp Lys Ser Ser Thr Ala Tyr
65                  70                  75                  80

Met Glu Phe Arg Ser Leu Thr Ser Glu Asp Ser Ala Val Tyr Tyr Cys
                85                  90                  95

Ala Arg Met Gly Tyr His Gly Pro His Leu Asp Phe Asp Val Trp Gly
            100                 105                 110

Ala Gly Thr Thr Val Thr Val Ser Pro
        115                 120

<210> SEQ ID NO 13
<211> LENGTH: 108
<212> TYPE: PRT
<213> ORGANISM: Artificial Sequence
```

```
<220> FEATURE:
<223> OTHER INFORMATION: Description of Artificial Sequence: Synthetic
      amino acid sequence of clone 12H3 light chain variable region

<400> SEQUENCE: 13

Asp Ile Val Met Thr Gln Ser His Lys Phe Met Ser Thr Ser Leu Gly
1               5                   10                  15

Asp Arg Val Ser Ile Thr Cys Lys Ala Ser Gln Asp Val Gly Ala Ala
            20                  25                  30

Val Ala Trp Tyr Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Gly
    50                  55                  60

Gly Gly Ser Gly Thr Asp Phe Thr Leu Thr Ile Ser Asn Val Gln Ser
65                  70                  75                  80

Glu Asp Leu Thr Asp Tyr Phe Cys Gln Gln Tyr Ile Asn Tyr Pro Leu
                85                  90                  95

Thr Phe Gly Gly Gly Thr Lys Leu Glu Ile Lys Arg
            100                 105

<210> SEQ ID NO 14
<211> LENGTH: 10
<212> TYPE: PRT
<213> ORGANISM: Artificial Sequence
<220> FEATURE:
<223> OTHER INFORMATION: Description of Artificial Sequence: Synthetic
      amino acid sequence of clone 12H3 heavy chain CDR1

<400> SEQUENCE: 14

Gly Tyr Thr Phe Lys Asp Tyr Thr Met His
1               5                   10

<210> SEQ ID NO 15
<211> LENGTH: 17
<212> TYPE: PRT
<213> ORGANISM: Artificial Sequence
<220> FEATURE:
<223> OTHER INFORMATION: Description of Artificial Sequence: Synthetic
      amino acid sequence of clone 12H3 heavy chain CDR2

<400> SEQUENCE: 15

Gly Ile Tyr Pro Asn Asn Gly Gly Ser Thr Tyr Asn Gln Asn Phe Lys
1               5                   10                  15

Asp

<210> SEQ ID NO 16
<211> LENGTH: 12
<212> TYPE: PRT
<213> ORGANISM: Artificial Sequence
<220> FEATURE:
<223> OTHER INFORMATION: Description of Artificial Sequence: Synthetic
      amino acid sequence of clone 12H3 heavy chain CDR2

<400> SEQUENCE: 16

Met Gly Tyr His Gly Pro His Leu Asp Phe Asp Val
1               5                   10

<210> SEQ ID NO 17
<211> LENGTH: 11
<212> TYPE: PRT
<213> ORGANISM: Artificial Sequence
<220> FEATURE:
<223> OTHER INFORMATION: Description of Artificial Sequence: Synthetic
      amino acid sequence of clone 12H3 light chain CDR1
```

<400> SEQUENCE: 17

Lys Ala Ser Gln Asp Val Gly Ala Ala Val Ala
1               5                   10

<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence: Synthetic
      amino acid sequence of clone 12H3 light chain CDR2

<400> SEQUENCE: 18

Trp Ala Ser Thr Arg His Thr
1               5

<210> SEQ ID NO 19
<211> LENGTH: 9
<212> TYPE: PRT
<213> ORGANISM: Artificial Sequence
<220> FEATURE:
<223> OTHER INFORMATION: Description of Artificial Sequence: Synthetic
      amino acid sequence of clone 12H3 light chain CDR3

<400> SEQUENCE: 19

Gln Gln Tyr Ile Asn Tyr Pro Leu Thr
1               5

<210> SEQ ID NO 20
<211> LENGTH: 1398
<212> TYPE: DNA
<213> ORGANISM: Artificial Sequence
<220> FEATURE:
<223> OTHER INFORMATION: Description of Artificial Sequence: Synthetic
      chimeric clone polynucleotide

<400> SEQUENCE: 20

```
atggagtgga gcggagtgtt tatgttcctg ctgagcgtga ccgctggcgt gcactcagag      60
gtgcagctgc agcagtcagg ccccgagctg gtcaagcctg cgctagcgt gaagatgagc      120 tgtaaagcta gcggctacac cttcactagc tacgtgatgc actgggtcaa gcagaagccc      180
ggccagggcc tggagtggat cggctatatt aaccectata cgacggcac taagtataac      240 gagaagttta agggcaaggc taccctgact agcgataagt ctagctctac cgcctatatg      300
gaactgtcta gtctgactag tgaagatagc gccgtctact actgcgctaa ctactacggc      360
tctagcctgt ctatggacta ctggggccag ggcactagcg tgaccgtgtc tagcgctagc      420
actaagggcc ctagcgtgtt cccccctggcc cctgctctca gatctactag cgagtctacc      480
gccgctctgg gctgcctggt caaggactac ttccccgagc ccgtgaccgt cagctggaat      540
agcggcgctc tgactagcgg cgtgcacacc ttccctgccg tgctgcagtc tagcggcctg      600
tatagtctgt ctagcgtggt caccgtgcct agttctagcc tgggcactaa gacctacacc      660
tgtaacgtgg accacaagcc ctctaacact aaggtggaca gcgggtgga atctaagtac      720 ggccctccct gcccccctg ccctgcccct gaatttctgg gcggacctag tgtgttcctg      780
ttcccaccta agcctaagga caccctgatg atctctagaa cccccgaagt gacctgcgtg      840
gtggtggacg tgtcacagga agatcccgag gtccagttta attggtacgt ggacggcgtg      900
gaagtgcaca acgctaagac taagcctaga gaggaacagt ttaactctac ctatagggtc      960
gtcagcgtgc tgaccgtgct gcaccaggac tggctgaacg gcaaagagta taagtgtaaa     1020
```

```
gtgtctaaca agggcctgcc tagctctatc gaaaagacta tctctaaggc taagggccag      1080
cctagagaac ctcaggtcta caccctgccc cctagtcagg aagagatgac taagaatcag      1140
gtgtcactga cctgtctggt caagggcttc taccctagcg atatcgccgt cgagtgggag      1200
tctaacggcc agcccgagaa caactataag actaccccc ctgtgctgga tagcgacggt       1260
agcttcttcc tgtactcacg gctgaccgtg ataagtcta ggtggcagga aggcaacgtc       1320
tttagctgta gcgtgatgca cgaggccctg cacaatcact acactcagaa gtcactgagc      1380
ctgagcctgg gcaagtga                                                    1398
```

<210> SEQ ID NO 21
<211> LENGTH: 702
<212> TYPE: DNA
<213> ORGANISM: Artificial Sequence
<220> FEATURE:
<223> OTHER INFORMATION: Description of Artificial Sequence: Synthetic
      chimeric clone polynucleotide

<400> SEQUENCE: 21

```
atggagtgga gcggagtgtt tatgttcctg ctgagcgtga ccgctggcgt gcactcagat      60
attcagatga ctcagactac ctctagcctg agcgctagcc tgggcgatag agtgactatt      120
agctgtagag ctagtcagga tatctctaac tacctgaact ggtatcagca gaaacccgac      180
ggcaccgtga agctgctgat ctactacacc tctagactgc actcaggcgt gccctctagg      240
tttagcggta gcggtagtgg caccgactat agcctgacta tctctaacct ggaacaggaa      300
gatatcgcta cctacttctg tcagcaggc aacaccctgc cctggacctt cggcggaggc       360
actaagctgg aaatcaagcg gaccgtggcc gctccctcag tgtttatctt cccacctagc      420
gacgagcagc tgaagtccgg caccgctagc gtcgtgtgcc tgctgaacaa cttctaccct      480
agagaagcta aggtgcagtg gaaagtggat aacgccctgc agtcaggcaa ctctcaggaa      540
tcagtcaccg agcaggactc taaggatagc acctatagcc tgtctagcac cctgaccctg      600
tctaaggccg actacgagaa gcacaaggtc tacgcctgcg aagtgactca ccagggactg      660
tctagccccg tgactaagtc ctttaataga ggcgagtgct ga                         702
```

<210> SEQ ID NO 22
<211> LENGTH: 1407
<212> TYPE: DNA
<213> ORGANISM: Artificial Sequence
<220> FEATURE:
<223> OTHER INFORMATION: Description of Artificial Sequence: Synthetic
      chimeric clone polynucleotide

<400> SEQUENCE: 22

```
atggagtggt caggcgtgtt catgttcctg ctgagcgtga ccgctggcgt gcactcagag      60
gtgcagctgc agcagtcagg ccccgagctg gtcaagcctg gcgctagcgt gaagatgagc      120
tgtaaagcta gcggctacac cttcactagc tacgtgatgc actgggtcaa gcagaagccc      180
ggtcagggcc tggagtggat cggctatatt aaccccctata cgacggcac taagtataac       240 gagaagttta aggtaaagc taccctgact agcgataagt ctagctctac cgcctatatg       300
gaactgtcta gtctgactag tgaagatagc gccgtctact actgcgctaa ctactacggc      360
tctagcctgt ctatggacta ctggggtcag ggcactagcg tgaccgtgtc tagcgctagc      420
actaagggcc ctagcgtgtt ccccctggcc cctagctcta gtctactag cggcggcacc       480 gccgctctgg gctgcctggt caaggactac ttccccgagc ccgtgaccgt cagctggaat      540
agcggcgctc tgactagcgg agtgcacacc ttccccgccg tgctgcagtc tagcggcctg      600
```

| | |
|---|---|
| tatagtctgt ctagcgtggt caccgtgcct agttctagcc tgggcactca gacctatatc | 660 |
| tgtaacgtga accacaagcc ctctaacact aaggtggaca agaaggtgga acctaagtcc | 720 |
| tgcgataaga ctcacacctg tccccctgc cctgccctg agctgctggg aggacctagt | 780 |
| gtgttcctgt tcccacctaa gcctaaggac accctgatga tctctagaac ccccgaagtg | 840 |
| acctgcgtgg tggtggacgt cagtcacgag gaccctgaag tgaagtttaa ttggtacgtg | 900 |
| gacggcgtgg aagtgcacaa cgctaagact aagcctagag aggaacagta taactctacc | 960 |
| tatagggtcg tcagcgtgct gaccgtgctg caccaggact ggctgaacgg taaagagtat | 1020 |
| aagtgtaaag tgtctaacaa ggccctgcca gccctatcg aaaagactat ctctaaggct | 1080 |
| aagggtcagc ctagggaacc tcaggtctac accctgcccc ctagtaggga cgagctgact | 1140 |
| aagaatcagg tcagcctgac ttgtctggtc aagggcttct accctagcga tatcgccgtc | 1200 |
| gagtgggagt ctaacggtca gcccgagaac aactataaga ctacccccc tgtgctggat | 1260 |
| agcgacggta gcttcttcct gtactctaaa ctgaccgtgg ataagtctag gtggcagcag | 1320 |
| ggtaacgtgt tcagctgtag cgtgatgcac gaggccctgc acaatcacta cactcagaag | 1380 |
| tcactgagcc tgagcccgg taagtga | 1407 |

<210> SEQ ID NO 23
<211> LENGTH: 1404
<212> TYPE: DNA
<213> ORGANISM: Artificial Sequence
<220> FEATURE:
<223> OTHER INFORMATION: Description of Artificial Sequence: Synthetic
      chimeric clone polynucleotide

<400> SEQUENCE: 23

| | |
|---|---|
| atggagtggt ctggtgtctt tatgttcctg ctgtccgtga ccgcgggtgt ccacagcgag | 60 |
| gtgcagctgc agcagtccgg ccctgagctg gtgaaacctg gcgcctccgt gaagatctcc | 120 |
| tgcaagacct ccggctacac cttcaaggac tacacaatgc actgggtgaa acagtcccac | 180 |
| ggcaagtcct ggagtggat cggcggaatc taccccaaca cggcggctc cacctacaac | 240 |
| cagaacttca aggacaaggc caccctgacc gtggacaagt cctcctccac cgcctatatg | 300 |
| gaatttcggt ccctgaccct cgaggactcc gccgtgtact actgcgcccg gatgggctac | 360 |
| cacggccccc acctggattt cgacgtgtgg ggcgctggca ccaccgtgac cgtgtctcca | 420 |
| gctagcacca agggcccctc cgtgttccct ctggccccctt gctccggtc cacctccgag | 480 |
| tctaccgccg ctctgggctg cctggtgaaa gactacttcc ccgagcccgt gacagtgtcc | 540 |
| tggaactctg gcgccctgac cagcggcgtg cacaccttcc ctgccgtgct gcagtcctcc | 600 |
| ggcctgtact ccctgtcctc cgtggtgaca gtgccctcct ccagcctggg caccaagacc | 660 |
| tacacctgta acgtggacca caagccctcc aacaccaagg tggacaagcg gtggaatct | 720 |
| aagtacggcc ctcccctgccc accttgccct gccctgaat tctgggcgg accttccgtg | 780 |
| ttcctgttcc ccccaaagcc caaggacacc ctgatgatct cccggacccc cgaagtgacc | 840 |
| tgcgtggtgg tggacgtgtc caagaagat cccgaggtcc agttcaattg gtacgtggac | 900 |
| ggcgtggaag tgcacaacgc caagaccaag cccagagagg aacagttcaa ctccacctac | 960 |
| cgggtggtgt ccgtgctgac cgtgctgcac caggactggc tgaacggcaa agagtacaag | 1020 |
| tgcaaggtct ccaacaaggg cctgccagc tctatcgaaa agacaatctc caaggccaag | 1080 |
| ggccagcccc gcgagcccca ggtgtacacc ctgcctccca gccaagaaga gatgaccaag | 1140 |
| aaccaggtgt ccctgacttg tctggtgaaa ggcttctacc cctccgatat cgccgtcgag | 1200 |

```
tgggagtcca acggccagcc cgagaacaac tacaagacca ccccccctgt gctggactcc    1260
gacggctcct tcttcctgta ctctcggctg acagtggata agtcccggtg gcaagaaggc    1320
aacgtcttct cctgctccgt gatgcacgag gccctgcaca accactacac ccagaagtcc    1380
ctgtccctga gcctgggcaa gtag                                           1404
```

<210> SEQ ID NO 24
<211> LENGTH: 702
<212> TYPE: DNA
<213> ORGANISM: Artificial Sequence
<220> FEATURE:
<223> OTHER INFORMATION: Description of Artificial Sequence: Synthetic
      chimeric clone polynucleotide

<400> SEQUENCE: 24

```
atggagtggt ccggtgtctt tatgttcctg ctgtccgtga ccgctggcgt gcactccgat     60
atcgtgatga cccagtccca caagtttatg tccacctccc tgggcgacag agtctctatt    120
acctgcaagg cctcccagga cgtgggcgct gccgtggcct ggtatcagca aaagcccggc    180
cagtccccca agctgctgat ctactgggcc tccaccagac acaccggcgt gcccgacaga    240
ttcaccggcg gaggctctgg caccgacttc accctgacaa tctccaacgt gcagtccgag    300
gacctgaccg actacttctg ccagcagtat atcaactacc ccctgacctt cggcggaggc    360
accaagctga aaatcaagcg gaccgtggcc gctccctccg tgtttatctt cccaccctcc    420
gacgagcagc tgaagtccgg caccgcctcc gtggtctgcc tgctgaacaa cttctacccc    480
cgcgaggcca aggtgcagtg gaaggtggac aacgccctgc agtccggcaa ctcccaagaa    540
tccgtgaccg agcaggactc caaggacagc acctactccc tgtcctccac cctgaccctg    600
tccaaggccg actacgagaa gcacaaggtg tacgcctgcg aagtgaccca ccagggcctg    660
tccagccccg tgaccaagtc cttcaaccgg ggcgagtgct aa                       702
```

<210> SEQ ID NO 25
<211> LENGTH: 465
<212> TYPE: PRT
<213> ORGANISM: Artificial Sequence
<220> FEATURE:
<223> OTHER INFORMATION: Description of Artificial Sequence: Synthetic
      amino acid sequence of chimeric clone 20E5 human IgG4 chain

<400> SEQUENCE: 25

```
Met Glu Trp Ser Gly Val Phe Met Phe Leu Leu Ser Val Thr Ala Gly
1               5                   10                  15

Val His Ser Glu Val Gln Leu Gln Gln Ser Gly Pro Glu Leu Val Lys
            20                  25                  30

Pro Gly Ala Ser Val Lys Met Ser Cys Lys Ala Ser Gly Tyr Thr Phe
        35                  40                  45

Thr Ser Tyr Val Met His Trp Val Lys Gln Lys Pro Gly Gln Gly Leu
    50                  55                  60

Glu Trp Ile Gly Tyr Ile Asn Pro Tyr Asn Asp Gly Thr Lys Tyr Asn
65                  70                  75                  80

Glu Lys Phe Lys Gly Lys Ala Thr Leu Thr Ser Asp Lys Ser Ser Ser
                85                  90                  95

Thr Ala Tyr Met Glu Leu Ser Ser Leu Thr Ser Glu Asp Ser Ala Val
            100                 105                 110

Tyr Tyr Cys Ala Asn Tyr Tyr Gly Ser Ser Leu Ser Met Asp Tyr Trp
        115                 120                 125
```

```
Gly Gln Gly Thr Ser Val Thr Val Ser Ser Ala Ser Thr Lys Gly Pro
    130                 135                 140
Ser Val Phe Pro Leu Ala Pro Cys Ser Arg Ser Thr Ser Glu Ser Thr
145                 150                 155                 160
Ala Ala Leu Gly Cys Leu Val Lys Asp Tyr Phe Pro Glu Pro Val Thr
                165                 170                 175
Val Ser Trp Asn Ser Gly Ala Leu Thr Ser Gly Val His Thr Phe Pro
            180                 185                 190
Ala Val Leu Gln Ser Ser Gly Leu Tyr Ser Leu Ser Ser Val Val Thr
        195                 200                 205
Val Pro Ser Ser Ser Leu Gly Thr Lys Thr Tyr Thr Cys Asn Val Asp
210                 215                 220
His Lys Pro Ser Asn Thr Lys Val Asp Lys Arg Val Glu Ser Lys Tyr
225                 230                 235                 240
Gly Pro Pro Cys Pro Cys Pro Ala Pro Glu Phe Leu Gly Gly Pro
                245                 250                 255
Ser Val Phe Leu Phe Pro Pro Lys Pro Lys Asp Thr Leu Met Ile Ser
            260                 265                 270
Arg Thr Pro Glu Val Thr Cys Val Val Val Asp Val Ser Gln Glu Asp
        275                 280                 285
Pro Glu Val Gln Phe Asn Trp Tyr Val Asp Gly Val Glu Val His Asn
290                 295                 300
Ala Lys Thr Lys Pro Arg Glu Glu Gln Phe Asn Ser Thr Tyr Arg Val
305                 310                 315                 320
Val Ser Val Leu Thr Val Leu His Gln Asp Trp Leu Asn Gly Lys Glu
                325                 330                 335
Tyr Lys Cys Lys Val Ser Asn Lys Gly Leu Pro Ser Ser Ile Glu Lys
            340                 345                 350
Thr Ile Ser Lys Ala Lys Gly Gln Pro Arg Glu Pro Gln Val Tyr Thr
        355                 360                 365
Leu Pro Pro Ser Gln Glu Glu Met Thr Lys Asn Gln Val Ser Leu Thr
370                 375                 380
Cys Leu Val Lys Gly Phe Tyr Pro Ser Asp Ile Ala Val Glu Trp Glu
385                 390                 395                 400
Ser Asn Gly Gln Pro Glu Asn Asn Tyr Lys Thr Thr Pro Pro Val Leu
                405                 410                 415
Asp Ser Asp Gly Ser Phe Phe Leu Tyr Ser Arg Leu Thr Val Asp Lys
            420                 425                 430
Ser Arg Trp Gln Glu Gly Asn Val Phe Ser Cys Ser Val Met His Glu
        435                 440                 445
Ala Leu His Asn His Tyr Thr Gln Lys Ser Leu Ser Leu Ser Leu Gly
    450                 455                 460
Lys
465

<210> SEQ ID NO 26
<211> LENGTH: 233
<212> TYPE: PRT
<213> ORGANISM: Artificial Sequence
<220> FEATURE:
<223> OTHER INFORMATION: Description of Artificial Sequence: Synthetic
      amino acid sequence of chimeric clone 20E5 human kappa chain

<400> SEQUENCE: 26

Met Glu Trp Ser Gly Val Phe Met Phe Leu Leu Ser Val Thr Ala Gly
1               5                   10                  15
```

Val His Ser Asp Ile Gln Met Thr Gln Thr Thr Ser Ser Leu Ser Ala
        20                  25                  30

Ser Leu Gly Asp Arg Val Thr Ile Ser Cys Arg Ala Ser Gln Asp Ile
        35                  40                  45

Ser Asn Tyr Leu Asn Trp Tyr Gln Gln Lys Pro Asp Gly Thr Val Lys
 50                  55                  60

Leu Leu Ile Tyr Tyr Thr Ser Arg Leu His Ser Gly Val Pro Ser Arg
 65                  70                  75                  80

Phe Ser Gly Ser Gly Ser Gly Thr Asp Tyr Ser Leu Thr Ile Ser Asn
                 85                  90                  95

Leu Glu Gln Glu Asp Ile Ala Thr Tyr Phe Cys Gln Gln Gly Asn Thr
            100                 105                 110

Leu Pro Trp Thr Phe Gly Gly Gly Thr Lys Leu Glu Ile Lys Arg Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu Cys
225                 230

<210> SEQ ID NO 27
<211> LENGTH: 468
<212> TYPE: PRT
<213> ORGANISM: Artificial Sequence
<220> FEATURE:
<223> OTHER INFORMATION: Description of Artificial Sequence: Synthetic
      amino acid sequence of chimeric clone 20E5 human IgG1 chain

<400> SEQUENCE: 27

Met Glu Trp Ser Gly Val Phe Met Phe Leu Leu Ser Val Thr Ala Gly
 1               5                  10                  15

Val His Ser Glu Val Gln Leu Gln Gln Ser Gly Pro Glu Leu Val Lys
        20                  25                  30

Pro Gly Ala Ser Val Lys Met Ser Cys Lys Ala Ser Gly Tyr Thr Phe
        35                  40                  45

Thr Ser Tyr Val Met His Trp Val Lys Gln Lys Pro Gly Gln Gly Leu
 50                  55                  60

Glu Trp Ile Gly Tyr Ile Asn Pro Tyr Asn Asp Gly Thr Lys Tyr Asn
 65                  70                  75                  80

Glu Lys Phe Lys Gly Lys Ala Thr Leu Thr Ser Asp Lys Ser Ser Ser
                 85                  90                  95

Thr Ala Tyr Met Glu Leu Ser Ser Leu Thr Ser Glu Asp Ser Ala Val
            100                 105                 110

Tyr Tyr Cys Ala Asn Tyr Tyr Gly Ser Ser Leu Ser Met Asp Tyr Trp
        115                 120                 125

Gly Gln Gly Thr Ser Val Thr Val Ser Ser Ala Ser Thr Lys Gly Pro

```
                130             135             140
Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Val Val Thr
            195                 200                 205

Val Pro Ser Ser Ser Leu Gly Thr Gln Thr Tyr Ile Cys Asn Val Asn
            210                 215                 220

His Lys Pro Ser Asn Thr Lys Val Asp Lys Val Glu Pro Lys Ser
225                 230                 235                 240

Cys Asp Lys Thr His Thr Cys Pro Pro Cys Pro Ala Pro Glu Leu Leu
                245                 250                 255

Gly Gly Pro Ser Val Phe Leu Phe Pro Pro Lys Pro Lys Asp Thr Leu
                260                 265                 270

Met Ile Ser Arg Thr Pro Glu Val Thr Cys Val Val Val Asp Val Ser
            275                 280                 285

His Glu Asp Pro Glu Val Lys Phe Asn Trp Tyr Val Asp Gly Val Glu
            290                 295                 300

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Ala Leu Pro Ala Pro
                340                 345                 350

Ile Glu Lys Thr Ile Ser Lys Ala Lys Gly Gln Pro Arg Glu Pro Gln
            355                 360                 365

Val Tyr Thr Leu Pro Pro Ser Arg Asp Glu Leu Thr Lys Asn Gln Val
            370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Lys Leu Thr
                420                 425                 430

Val Asp Lys Ser Arg Trp Gln Gln Gly Asn Val Phe Ser Cys Ser Val
            435                 440                 445

Met His Glu Ala Leu His Asn His Tyr Thr Gln Lys Ser Leu Ser Leu
450                 455                 460

Ser Pro Gly Lys
465

<210> SEQ ID NO 28
<211> LENGTH: 467
<212> TYPE: PRT
<213> ORGANISM: Artificial Sequence
<220> FEATURE:
<223> OTHER INFORMATION: Description of Artificial Sequence: Synthetic
      amino acid sequence of chimeric clone 12H3 human IgG4 chain

<400> SEQUENCE: 28

Met Glu Trp Ser Gly Val Phe Met Phe Leu Leu Ser Val Thr Ala Gly
1               5                   10                  15
```

```
Val His Ser Glu Val Gln Leu Gln Gln Ser Gly Pro Glu Leu Val Lys
             20                  25                  30

Pro Gly Ala Ser Val Lys Ile Ser Cys Lys Thr Ser Gly Tyr Thr Phe
         35                  40                  45

Lys Asp Tyr Thr Met His Trp Val Lys Gln Ser His Gly Lys Ser Leu
 50                  55                  60

Glu Trp Ile Gly Gly Ile Tyr Pro Asn Asn Gly Ser Thr Tyr Asn
 65                  70                  75                  80

Gln Asn Phe Lys Asp Lys Ala Thr Leu Thr Val Asp Lys Ser Ser Ser
             85                  90                  95

Thr Ala Tyr Met Glu Phe Arg Ser Leu Thr Ser Glu Asp Ser Ala Val
            100                 105                 110

Tyr Tyr Cys Ala Arg Met Gly Tyr His Gly Pro His Leu Asp Phe Asp
        115                 120                 125

Val Trp Gly Ala Gly Thr Thr Val Thr Val Ser Pro Ala Ser Thr Lys
130                 135                 140

Gly Pro Ser Val Phe Pro Leu Ala Pro Cys Ser Arg Ser Thr Ser Glu
145                 150                 155                 160

Ser Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Leu Gly Thr Lys Thr Tyr Thr Cys Asn
210                 215                 220

Val Asp His Lys Pro Ser Asn Thr Lys Val Asp Lys Arg Val Glu Ser
225                 230                 235                 240

Lys Tyr Gly Pro Pro Cys Pro Cys Pro Ala Pro Glu Phe Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser Gln
        275                 280                 285

Glu Asp Pro Glu Val Gln Phe Asn Trp Tyr Val Asp Gly Val Glu Val
290                 295                 300

His Asn Ala Lys Thr Lys Pro Arg Glu Glu Gln Phe Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Gly Leu Pro Ser Ser Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Gln Glu Glu Met Thr Lys Asn Gln Val Ser
370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Arg Leu Thr Val
            420                 425                 430

Asp Lys Ser Arg Trp Gln Glu Gly Asn Val Phe Ser Cys Ser Val Met
```

435                 440                 445
His Glu Ala Leu His Asn His Tyr Thr Gln Lys Ser Leu Ser Leu Ser
    450                 455                 460

Leu Gly Lys
465

<210> SEQ ID NO 29
<211> LENGTH: 233
<212> TYPE: PRT
<213> ORGANISM: Artificial Sequence
<220> FEATURE:
<223> OTHER INFORMATION: Description of Artificial Sequence: Synthetic
      amino acid sequence of chimeric clone 12H3 human kappa chain

<400> SEQUENCE: 29

Met Glu Trp Ser Gly Val Phe Met Phe Leu Leu Ser Val Thr Ala Gly
1               5                   10                  15

Val His Ser Asp Ile Val Met Thr Gln Ser His Lys Phe Met Ser Thr
            20                  25                  30

Ser Leu Gly Asp Arg Val Ser Ile Thr Cys Lys Ala Ser Gln Asp Val
        35                  40                  45

Gly Ala Ala Val Ala Trp Tyr Gln Gln Lys Pro Gly Gln Ser Pro Lys
    50                  55                  60

Leu Leu Ile Tyr Trp Ala Ser Thr Arg His Thr Gly Val Pro Asp Arg
65                  70                  75                  80

Phe Thr Gly Gly Gly Ser Gly Thr Asp Phe Thr Leu Thr Ile Ser Asn
                85                  90                  95

Val Gln Ser Glu Asp Leu Thr Asp Tyr Phe Cys Gln Gln Tyr Ile Asn
            100                 105                 110

Tyr Pro Leu Thr Phe Gly Gly Gly Thr Lys Leu Glu Ile Lys Arg Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu Cys
225                 230

<210> SEQ ID NO 30
<211> LENGTH: 240
<212> TYPE: PRT
<213> ORGANISM: Artificial Sequence
<220> FEATURE:
<223> OTHER INFORMATION: Description of Artificial Sequence: Synthetic
      amino acid sequence of human CD134_CRD2 (aa 1-28/66-277)
<220> FEATURE:
<221> NAME/KEY: SIGNAL
<222> LOCATION: (1)..(28)
<220> FEATURE:
<221> NAME/KEY: TRANSMEM
<222> LOCATION: (178)..(198)

-continued

<400> SEQUENCE: 30

Met Cys Val Gly Ala Arg Arg Leu Gly Arg Gly Pro Cys Ala Ala Leu
1               5                   10                  15

Leu Leu Leu Gly Leu Gly Leu Ser Thr Val Thr Gly Pro Cys Gly Pro
            20                  25                  30

Gly Phe Tyr Asn Asp Val Val Ser Lys Pro Cys Lys Pro Cys Thr
        35                  40                  45

Trp Cys Asn Leu Arg Ser Gly Ser Glu Arg Lys Gln Leu Cys Thr Ala
    50                  55                  60

Thr Gln Asp Thr Val Cys Arg Cys Arg Ala Gly Thr Gln Pro Leu Asp
65                  70                  75                  80

Ser Tyr Lys Pro Gly Val Asp Cys Ala Pro Cys Pro Pro Gly His Phe
                85                  90                  95

Ser Pro Gly Asp Asn Gln Ala Cys Lys Pro Trp Thr Asn Cys Thr Leu
            100                 105                 110

Ala Gly Lys His Thr Leu Gln Pro Ala Ser Asn Ser Ser Asp Ala Ile
        115                 120                 125

Cys Glu Asp Arg Asp Pro Pro Ala Thr Gln Pro Gln Glu Thr Gln Gly
130                 135                 140

Pro Pro Ala Arg Pro Ile Thr Val Gln Pro Thr Glu Ala Trp Pro Arg
145                 150                 155                 160

Thr Ser Gln Gly Pro Ser Thr Arg Pro Val Glu Val Pro Gly Gly Arg
                165                 170                 175

Ala Val Ala Ala Ile Leu Gly Leu Gly Leu Val Leu Gly Leu Leu Gly
            180                 185                 190

Pro Leu Ala Ile Leu Leu Ala Leu Tyr Leu Leu Arg Arg Asp Gln Arg
        195                 200                 205

Leu Pro Pro Asp Ala His Lys Pro Pro Gly Gly Gly Ser Phe Arg Thr
    210                 215                 220

Pro Ile Gln Glu Glu Gln Ala Asp Ala His Ser Thr Leu Ala Lys Ile
225                 230                 235                 240

<210> SEQ ID NO 31
<211> LENGTH: 198
<212> TYPE: PRT
<213> ORGANISM: Artificial Sequence
<220> FEATURE:
<223> OTHER INFORMATION: Description of Artificial Sequence: Synthetic
      amino acid sequence of human CD134_CRD3 (aa 1-28/108-277)
<220> FEATURE:
<221> NAME/KEY: SIGNAL
<222> LOCATION: (1)..(28)
<220> FEATURE:
<221> NAME/KEY: TRANSMEM
<222> LOCATION: (136)..(156)

<400> SEQUENCE: 31

Met Cys Val Gly Ala Arg Arg Leu Gly Arg Gly Pro Cys Ala Ala Leu
1               5                   10                  15

Leu Leu Leu Gly Leu Gly Leu Ser Thr Val Thr Gly Arg Cys Arg Ala
            20                  25                  30

Gly Thr Gln Pro Leu Asp Ser Tyr Lys Pro Gly Val Asp Cys Ala Pro
        35                  40                  45

Cys Pro Pro Gly His Phe Ser Pro Gly Asp Asn Gln Ala Cys Lys Pro
    50                  55                  60

Trp Thr Asn Cys Thr Leu Ala Gly Lys His Thr Leu Gln Pro Ala Ser
65                  70                  75                  80

```
Asn Ser Ser Asp Ala Ile Cys Glu Asp Arg Asp Pro Pro Ala Thr Gln
                85                  90                  95

Pro Gln Glu Thr Gln Gly Pro Pro Ala Arg Pro Ile Thr Val Gln Pro
            100                 105                 110

Thr Glu Ala Trp Pro Arg Thr Ser Gln Gly Pro Ser Thr Arg Pro Val
            115                 120                 125

Glu Val Pro Gly Gly Arg Ala Val Ala Ala Ile Leu Gly Leu Gly Leu
            130                 135                 140

Val Leu Gly Leu Leu Gly Pro Leu Ala Ile Leu Leu Ala Leu Tyr Leu
145                 150                 155                 160

Leu Arg Arg Asp Gln Arg Leu Pro Pro Asp Ala His Lys Pro Pro Gly
                165                 170                 175

Gly Gly Ser Phe Arg Thr Pro Ile Gln Glu Glu Gln Ala Asp Ala His
            180                 185                 190

Ser Thr Leu Ala Lys Ile
            195
```

<210> SEQ ID NO 32
<211> LENGTH: 179
<212> TYPE: PRT
<213> ORGANISM: Artificial Sequence
<220> FEATURE:
<223> OTHER INFORMATION: Description of Artificial Sequence: Synthetic
      Amino acid sequence of human CD134_CRD4 (aa 1-28/127-277)
<220> FEATURE:
<221> NAME/KEY: SIGNAL
<222> LOCATION: (1)..(28)
<220> FEATURE:
<221> NAME/KEY: TRANSMEM
<222> LOCATION: (117)..(137)

<400> SEQUENCE: 32

```
Met Cys Val Gly Ala Arg Arg Leu Gly Arg Gly Pro Cys Ala Ala Leu
1               5                   10                  15

Leu Leu Leu Gly Leu Gly Leu Ser Thr Val Thr Gly Pro Cys Pro Pro
                20                  25                  30

Gly His Phe Ser Pro Gly Asp Asn Gln Ala Cys Lys Pro Trp Thr Asn
            35                  40                  45

Cys Thr Leu Ala Gly Lys His Thr Leu Gln Pro Ala Ser Asn Ser Ser
50                  55                  60

Asp Ala Ile Cys Glu Asp Arg Asp Pro Pro Ala Thr Gln Pro Gln Glu
65                  70                  75                  80

Thr Gln Gly Pro Pro Ala Arg Pro Ile Thr Val Gln Pro Thr Glu Ala
                85                  90                  95

Trp Pro Arg Thr Ser Gln Gly Pro Ser Thr Arg Pro Val Glu Val Pro
            100                 105                 110

Gly Gly Arg Ala Val Ala Ala Ile Leu Gly Leu Gly Leu Val Leu Gly
            115                 120                 125

Leu Leu Gly Pro Leu Ala Ile Leu Leu Ala Leu Tyr Leu Leu Arg Arg
            130                 135                 140

Asp Gln Arg Leu Pro Pro Asp Ala His Lys Pro Pro Gly Gly Gly Ser
145                 150                 155                 160

Phe Arg Thr Pro Ile Gln Glu Glu Gln Ala Asp Ala His Ser Thr Leu
                165                 170                 175

Ala Lys Ile
```

<210> SEQ ID NO 33
<211> LENGTH: 159

```
<212> TYPE: PRT
<213> ORGANISM: Artificial Sequence
<220> FEATURE:
<223> OTHER INFORMATION: Description of Artificial Sequence: Synthetic
      amino acid sequence of human CD134_CRD4 truncated
      (aa 1-28/147-277)
<220> FEATURE:
<221> NAME/KEY: SIGNAL
<222> LOCATION: (1)..(28)
<220> FEATURE:
<221> NAME/KEY: TRANSMEM
<222> LOCATION: (97)..(117)

<400> SEQUENCE: 33

Met Cys Val Gly Ala Arg Arg Leu Gly Arg Gly Pro Cys Ala Ala Leu
1               5                   10                  15

Leu Leu Leu Gly Leu Gly Leu Ser Thr Val Thr Gly Cys Thr Leu Ala
                20                  25                  30

Gly Lys His Thr Leu Gln Pro Ala Ser Asn Ser Ser Asp Ala Ile Cys
            35                  40                  45

Glu Asp Arg Asp Pro Pro Ala Thr Gln Pro Gln Glu Thr Gln Gly Pro
        50                  55                  60

Pro Ala Arg Pro Ile Thr Val Gln Pro Thr Glu Ala Trp Pro Arg Thr
65                  70                  75                  80

Ser Gln Gly Pro Ser Thr Arg Pro Val Glu Val Pro Gly Gly Arg Ala
                85                  90                  95

Val Ala Ala Ile Leu Gly Leu Gly Leu Val Leu Gly Leu Leu Gly Pro
                100                 105                 110

Leu Ala Ile Leu Leu Ala Leu Tyr Leu Leu Arg Arg Asp Gln Arg Leu
            115                 120                 125

Pro Pro Asp Ala His Lys Pro Pro Gly Gly Gly Ser Phe Arg Thr Pro
        130                 135                 140

Ile Gln Glu Glu Gln Ala Asp Ala His Ser Thr Leu Ala Lys Ile
145                 150                 155

<210> SEQ ID NO 34
<211> LENGTH: 19
<212> TYPE: PRT
<213> ORGANISM: Homo sapiens

<400> SEQUENCE: 34

Arg Cys Arg Ala Gly Thr Gln Pro Leu Asp Ser Tyr Lys Pro Gly Val
1               5                   10                  15

Asp Cys Ala

<210> SEQ ID NO 35
<211> LENGTH: 107
<212> TYPE: PRT
<213> ORGANISM: Homo sapiens

<400> SEQUENCE: 35

Arg Cys Arg Ala Gly Thr Gln Pro Leu Asp Ser Tyr Lys Pro Gly Val
1               5                   10                  15

Asp Cys Ala Pro Cys Pro Pro Gly His Phe Ser Pro Gly Asp Asn Gln
                20                  25                  30

Ala Cys Lys Pro Trp Thr Asn Cys Thr Leu Ala Gly Lys His Thr Leu
            35                  40                  45

Gln Pro Ala Ser Asn Ser Ser Asp Ala Ile Cys Glu Asp Arg Asp Pro
        50                  55                  60

Pro Ala Thr Gln Pro Gln Glu Thr Gln Gly Pro Pro Ala Arg Pro Ile
```

```
                65                  70                  75                  80
Thr Val Gln Pro Thr Glu Ala Trp Pro Arg Thr Ser Gln Gly Pro Ser
                    85                  90                  95
Thr Arg Pro Val Glu Val Pro Gly Gly Arg Ala
            100                 105

<210> SEQ ID NO 36
<211> LENGTH: 68
<212> TYPE: PRT
<213> ORGANISM: Homo sapiens

<400> SEQUENCE: 36

Cys Thr Leu Ala Gly Lys His Thr Leu Gln Pro Ala Ser Asn Ser Ser
1               5                   10                  15
Asp Ala Ile Cys Glu Asp Arg Asp Pro Pro Ala Thr Gln Pro Gln Glu
                20                  25                  30
Thr Gln Gly Pro Pro Ala Arg Pro Ile Thr Val Gln Pro Thr Glu Ala
            35                  40                  45
Trp Pro Arg Thr Ser Gln Gly Pro Ser Thr Arg Pro Val Glu Val Pro
        50                  55                  60
Gly Gly Arg Ala
65

<210> SEQ ID NO 37
<211> LENGTH: 29
<212> TYPE: PRT
<213> ORGANISM: Homo sapiens

<400> SEQUENCE: 37

Thr Tyr Ser Ser Pro Glu Asp Gly Ile His Glu Leu Phe Pro Ala Pro
1               5                   10                  15
Asp Gly Glu Glu Asp Thr Ala Glu Leu Gln Gly Gly Cys
                20                  25

<210> SEQ ID NO 38
<211> LENGTH: 39
<212> TYPE: PRT
<213> ORGANISM: Homo sapiens

<400> SEQUENCE: 38

Arg Cys Arg Ala Gly Thr Gln Pro Leu Asp Ser Tyr Lys Pro Gly Val
1               5                   10                  15
Asp Cys Ala Pro Cys Pro Pro Gly His Phe Ser Pro Gly Asp Asn Gln
                20                  25                  30
Ala Cys Lys Pro Trp Thr Asn
            35

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Synthetic
      mkappa antisense primer (primer no: 201)

<400> SEQUENCE: 39
gacagttggt gcagcatcag                                               20

<210> SEQ ID NO 40
<211> LENGTH: 20
<212> TYPE: DNA
```

```
<213> ORGANISM: Artificial Sequence
<220> FEATURE:
<223> OTHER INFORMATION: Description of Artificial Sequence: Synthetic
      mkappa antisense primer (primer no: 266)

<400> SEQUENCE: 40
cactggatgg tgggaagatg                                                    20

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: Synthetic
      mIgG1 antisense primer (primer no: 203)

<400> SEQUENCE: 41
ggccagtgga tagacagatg                                                    20

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Synthetic
      mIgG1 antisense primer (primer no: 204)

<400> SEQUENCE: 42
tggacaggga tccagagttc                                                    20

<210> SEQ ID NO 43
<211> LENGTH: 25
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (14)..(14)
<223> OTHER INFORMATION: a, c, t or g
<220> FEATURE:
<221> NAME/KEY: modified_base
<222> LOCATION: (23)..(23)
<223> OTHER INFORMATION: a, c, t or g

<400> SEQUENCE: 43
gcgaagtaca aytncarcar wsngg                                              25

<210> SEQ ID NO 44
<211> LENGTH: 25
<212> TYPE: DNA
<213> ORGANISM: Artificial Sequence
<220> FEATURE:
<223> OTHER INFORMATION: Description of Artificial Sequence: Synthetic
      20E5HC sense primer (primer no: 260)
<220> FEATURE:
<221> NAME/KEY: modified_base
<222> LOCATION: (20)..(20)
<223> OTHER INFORMATION: a, c, t or g
<220> FEATURE:
<221> NAME/KEY: modified_base
<222> LOCATION: (23)..(23)
<223> OTHER INFORMATION: a, c, t or g

<400> SEQUENCE: 44
gcgtacaatt acarcarwsn ggncc                                              25

<210> SEQ ID NO 45
```

```
<211> LENGTH: 22
<212> TYPE: DNA
<213> ORGANISM: Artificial Sequence
<220> FEATURE:
<223> OTHER INFORMATION: Description of Artificial Sequence: Synthetic
      20E5LC sense primer (primer no: 265)
<220> FEATURE:
<221> NAME/KEY: modified_base
<222> LOCATION: (17)..(17)
<223> OTHER INFORMATION: a, c, t or g

<400> SEQUENCE: 45
gcgatataca ratgacncar ac                                             22

<210> SEQ ID NO 46
<211> LENGTH: 21
<212> TYPE: DNA
<213> ORGANISM: Artificial Sequence
<220> FEATURE:
<223> OTHER INFORMATION: Description of Artificial Sequence: Synthetic
      mIgG1 antisense primer (primer no: 416)

<400> SEQUENCE: 46
cagtggatag acagatgggg g                                              21

<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence: Synthetic
      mkappa antisense primer (primer no: 394)

<400> SEQUENCE: 47
actggatggt gggaagatgg                                                20

<210> SEQ ID NO 48
<211> LENGTH: 26
<212> TYPE: DNA
<213> ORGANISM: Artificial Sequence
<220> FEATURE:
<223> OTHER INFORMATION: Description of Artificial Sequence: Synthetic
      signal peptide sense primer (primer no: 405)

<400> SEQUENCE: 48
atgggatgga gctrtatcat sytctt                                         26

<210> SEQ ID NO 49
<211> LENGTH: 26
<212> TYPE: DNA
<213> ORGANISM: Artificial Sequence
<220> FEATURE:
<223> OTHER INFORMATION: Description of Artificial Sequence: Synthetic
      signal peptide sense primer (primer no: 410)

<400> SEQUENCE: 49
atggratgga gckggtctt tmtctt                                          26

<210> SEQ ID NO 50
<211> LENGTH: 24
<212> TYPE: DNA
<213> ORGANISM: Artificial Sequence
<220> FEATURE:
<223> OTHER INFORMATION: Description of Artificial Sequence: Synthetic
      signal peptide sense primer (primer no: 389)

<400> SEQUENCE: 50
atgggcwtca aagatggagt caca                                           24
```

<210> SEQ ID NO 51
<211> LENGTH: 24
<212> TYPE: DNA
<213> ORGANISM: Artificial Sequence
<220> FEATURE:
<223> OTHER INFORMATION: Description of Artificial Sequence: Synthetic
      CD134 leader sense primer (primer no: 362)

<400> SEQUENCE: 51
ctcggatccg ccaccatgtg cgtg                                          24

<210> SEQ ID NO 52
<211> LENGTH: 24
<212> TYPE: DNA
<213> ORGANISM: Artificial Sequence
<220> FEATURE:
<223> OTHER INFORMATION: Description of Artificial Sequence: Synthetic
      CRD2 sense primer (primer no: 364)

<400> SEQUENCE: 52
actgtcactg gaccctgcgg tccc                                          24

<210> SEQ ID NO 53
<211> LENGTH: 24
<212> TYPE: DNA
<213> ORGANISM: Artificial Sequence
<220> FEATURE:
<223> OTHER INFORMATION: Description of Artificial Sequence: Synthetic
      CRD2 antisense primer (primer no: 365)

<400> SEQUENCE: 53
gggaccgcag ggtccagtga cagt                                          24

<210> SEQ ID NO 54
<211> LENGTH: 24
<212> TYPE: DNA
<213> ORGANISM: Artificial Sequence
<220> FEATURE:
<223> OTHER INFORMATION: Description of Artificial Sequence: Synthetic
      CRD3 sense primer (primer no: 366)

<400> SEQUENCE: 54
actgtcactg gaaggtgcag ggct                                          24

<210> SEQ ID NO 55
<211> LENGTH: 24
<212> TYPE: DNA
<213> ORGANISM: Artificial Sequence
<220> FEATURE:
<223> OTHER INFORMATION: Description of Artificial Sequence: Synthetic
      CD134 end primer (primer no: 363)

<400> SEQUENCE: 55
agaattctta ttagatcttg gcca                                          24

<210> SEQ ID NO 56
<211> LENGTH: 24
<212> TYPE: DNA
<213> ORGANISM: Artificial Sequence
<220> FEATURE:
<223> OTHER INFORMATION: Description of Artificial Sequence: Synthetic
      CRD3 antisense primer (primer no: 367)

<400> SEQUENCE: 56
agccctgcac cttccagtga cagt                                          24

```
<210> SEQ ID NO 57
<211> LENGTH: 24
<212> TYPE: DNA
<213> ORGANISM: Artificial Sequence
<220> FEATURE:
<223> OTHER INFORMATION: Description of Artificial Sequence: Synthetic
      CRD4 sense primer (primer no: 368)

<400> SEQUENCE: 57
actgtcactg gaccctgccc ccct                                          24

<210> SEQ ID NO 58
<211> LENGTH: 24
<212> TYPE: DNA
<213> ORGANISM: Artificial Sequence
<220> FEATURE:
<223> OTHER INFORMATION: Description of Artificial Sequence: Synthetic
      CRD4 antisense primer (primer no: 369)

<400> SEQUENCE: 58 agggggggcag ggtccagtga cagt                                         24

<210> SEQ ID NO 59
<211> LENGTH: 24
<212> TYPE: DNA
<213> ORGANISM: Artificial Sequence
<220> FEATURE:
<223> OTHER INFORMATION: Description of Artificial Sequence: Synthetic
      CRD4 truncated sense primer (primer no: 370)

<400> SEQUENCE: 59
actgtcactg gatgcaccct ggct                                          24

<210> SEQ ID NO 60
<211> LENGTH: 24
<212> TYPE: DNA
<213> ORGANISM: Artificial Sequence
<220> FEATURE:
<223> OTHER INFORMATION: Description of Artificial Sequence: Synthetic
      CRD4 truncated antisense primer (primer no: 371)

<400> SEQUENCE: 60
agccagggtg catccagtga cagt                                          24

<210> SEQ ID NO 61
<211> LENGTH: 11
<212> TYPE: PRT
<213> ORGANISM: Artificial Sequence
<220> FEATURE:
<223> OTHER INFORMATION: Description of Artificial Sequence: Synthetic
      N-terminal amino acid sequence of clone 20E5 light chain

<400> SEQUENCE: 61

Asp Ile Gln Met Thr Gln Thr Thr Ser Ser Leu
1               5                   10

<210> SEQ ID NO 62
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Gly Gly Gly Gly Cys
1               5
```

```
<210> SEQ ID NO 63
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

His His His His His His Gly Gly Gly Gly Cys
1               5                   10
```